(12) United States Patent
Ternansky et al.

(10) Patent No.: US 10,022,418 B2
(45) Date of Patent: Jul. 17, 2018

(54) COMPOSITIONS AND METHODS FOR TREATING BETA-AMYLOID RELATED DISEASES

(71) Applicant: American Life Science Pharmaceuticals, Inc., San Diego, CA (US)

(72) Inventors: Robert J. Ternansky, San Diego, CA (US); Amy Allan, San Diego, CA (US); Gregory Hook, San Diego, CA (US)

(73) Assignee: AMERICAN LIFE SCIENCE PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 14/734,999

(22) Filed: Jun. 9, 2015

(65) Prior Publication Data
US 2016/0058824 A1    Mar. 3, 2016

Related U.S. Application Data

(63) Continuation of application No. 12/910,747, filed on Oct. 22, 2010, now abandoned, which is a continuation of application No. PCT/US2010/044683, filed on Aug. 6, 2010.

(60) Provisional application No. 61/293,783, filed on Jan. 11, 2010, provisional application No. 61/232,383, filed on Aug. 7, 2009, provisional application No. 61/232,388, filed on Aug. 7, 2009.

(51) Int. Cl.
| | |
|---|---|
| *A61K 38/05* | (2006.01) |
| *A61K 31/336* | (2006.01) |
| *A61J 1/03* | (2006.01) |
| *A61K 45/06* | (2006.01) |
| *C07K 5/078* | (2006.01) |

(52) U.S. Cl.
CPC .............. *A61K 38/05* (2013.01); *A61J 1/035* (2013.01); *A61K 31/336* (2013.01); *A61K 45/06* (2013.01); *C07K 5/06139* (2013.01)

(58) Field of Classification Search
CPC ...... A61K 45/06; A61K 38/05; A61K 31/336; C07K 5/06139; A61J 1/035
See application file for complete search history.

(56) References Cited

U.S. PATENT DOCUMENTS

| | | | | |
|---|---|---|---|---|
| 5,151,449 A | * | 9/1992 | Milgram | A61K 31/135 514/646 |
| 5,846,514 A | * | 12/1998 | Foster | C07B 59/002 424/1.81 |
| 6,726,924 B2 | * | 4/2004 | Keller | A61K 9/4858 424/450 |
| 2005/0211597 A1 | * | 9/2005 | Penfold | A61J 1/035 206/531 |

FOREIGN PATENT DOCUMENTS

| | | |
|---|---|---|
| WO | 2004084830 A2 | 10/2004 |
| WO | WO 2007/038772 A1 * | 4/2007 |

OTHER PUBLICATIONS

Fukishima, K., et al., "Metabolic fate loxistatin in rat", Xenobiotica, vol. 20, No. 10, (1990), pp. 1043-1051.
Wantanabe, Terukuni, "Pharmacokinetics of EST (Report 5): Pharmacokinetics of EST in Humans", Kiso to Rinsho, vol. 20, No. 4, (Mar. 1986), pp. 362-366.
Yamamoto et al., "Crystal structure and molecular conformation of E-64, cystein protease inhibitor" Chemical and Pharmaceutical Bulletin, Oct. 1989, v 37, n, 10, p. 2577-2581.
"Precision deuterium chemistry backgrounder" Concert Pharmaceuticals, 2007, p. 1-6.
Schmid, Extended European Search Report for EP 17182879 dated Jan. 22, 2018.

* cited by examiner

*Primary Examiner* — Kara Renita McMillian
(74) *Attorney, Agent, or Firm* — Greer, Burns & Crain; Gregory P. Einhorn; Greg Hook

(57) ABSTRACT

In alternative embodiments the invention provides compositions and methods for ameliorating diseases and conditions having a beta-amyloid component, including Alzheimer's disease (AD), Vascular Dementia (VD), dementia, pre-dementia, Cognitive Dysfunction Syndrome (CDS) and loss of cognition in humans and in non-human animal. In alternative embodiment the invention provides analogs of AB-007 and its acid form E64c (loxistatin), their preparation, and pharmaceutical compositions thereof and methods of making and using same. In alternative embodiments compositions of the invention are deuterated analogs of AB-007 (or E64d) and E64c (or loxistatin). In alternative embodiments compositions of the invention are metabolically blocked forms as compared to AB-007 and loxistatin. In alternative embodiments compositions of the invention are used to ameliorate (including treat, slow, reverse or prevent) a disease or condition which can be ameliorated by partial or complete inhibition of a cysteine protease, e.g., AD, VD, CDS. The invention also provides alternative dosage forms and formulations for AB-007 and loxistatin, and for compounds of this invention, which can be used e.g., to treat AD, VD and CDS, in humans and in non-human animals.

23 Claims, 15 Drawing Sheets

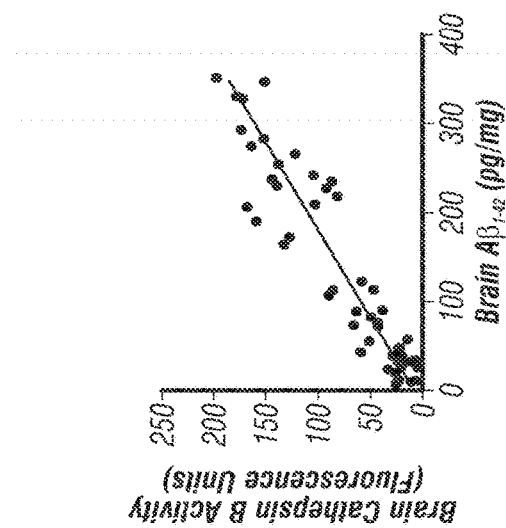
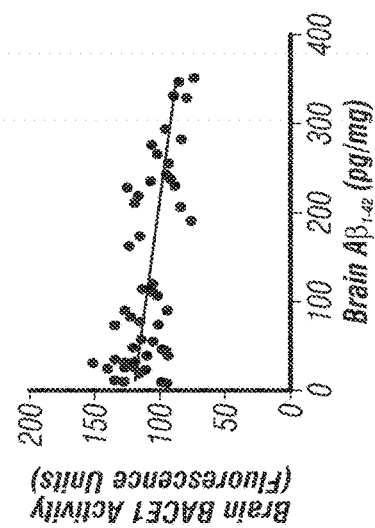
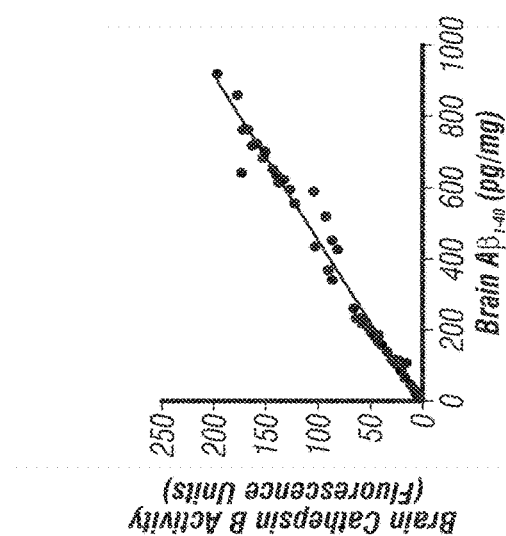
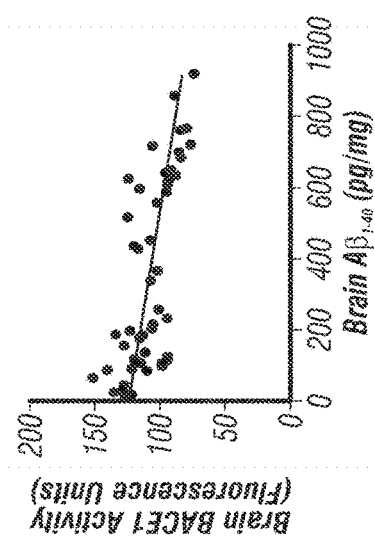
FIG. 8A
FIG. 8B
FIG. 8C
FIG. 8D

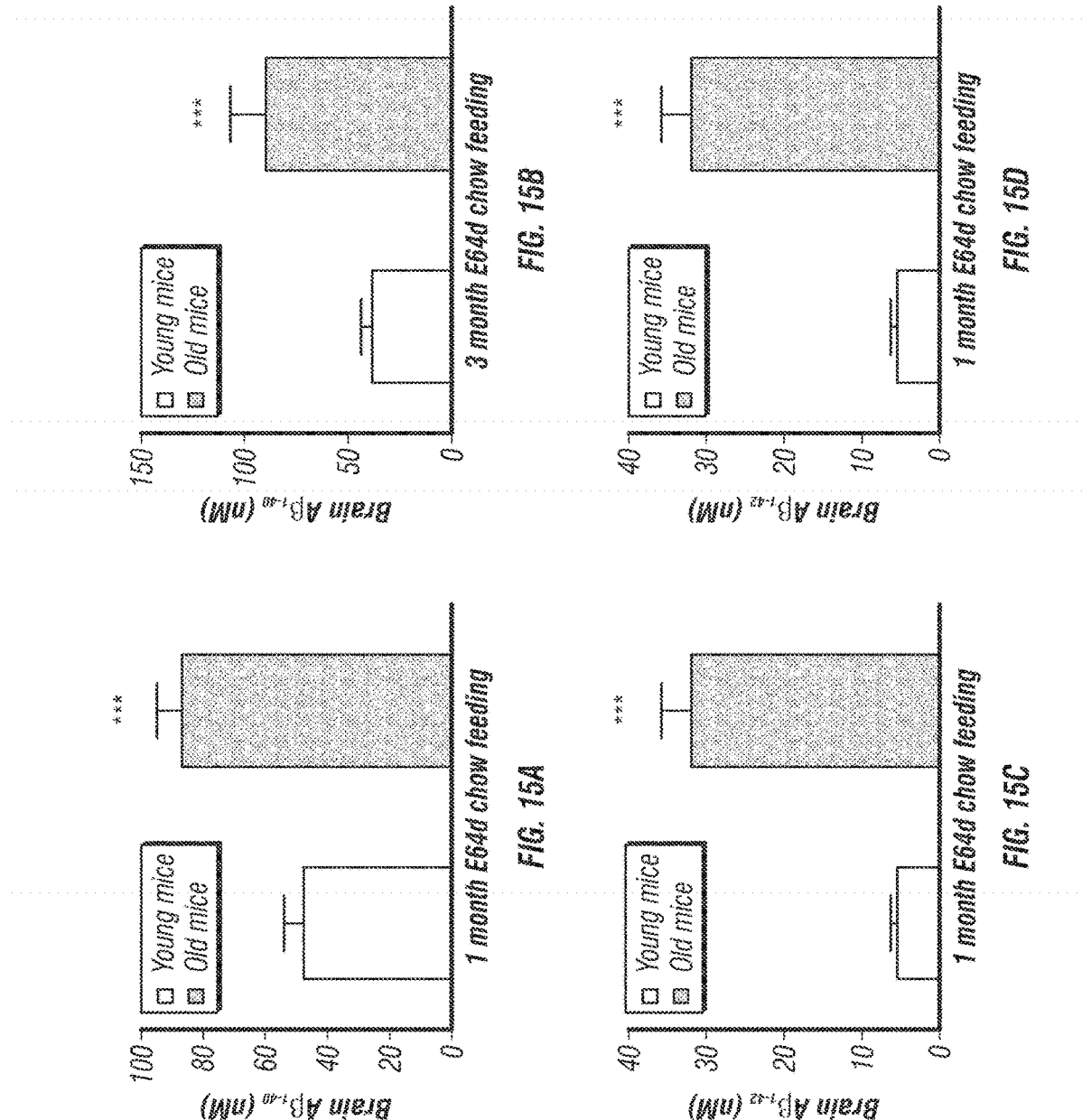

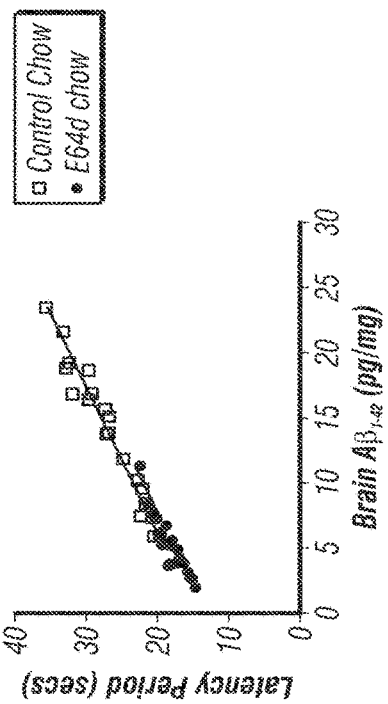
FIG. 17B
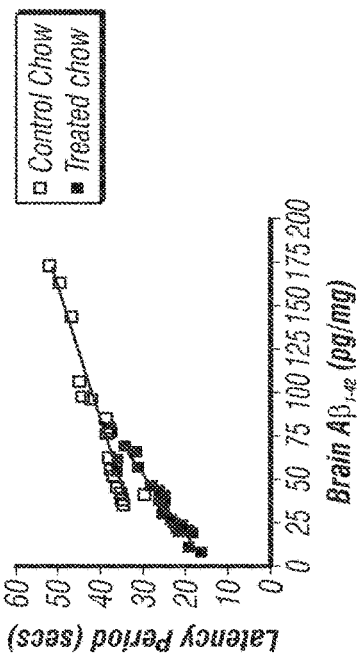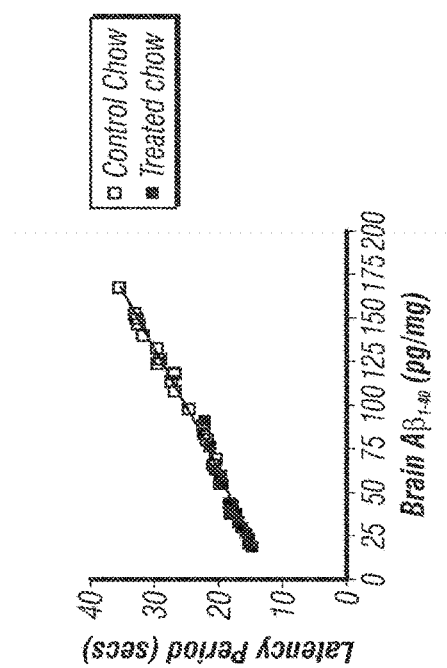
FIG. 17A
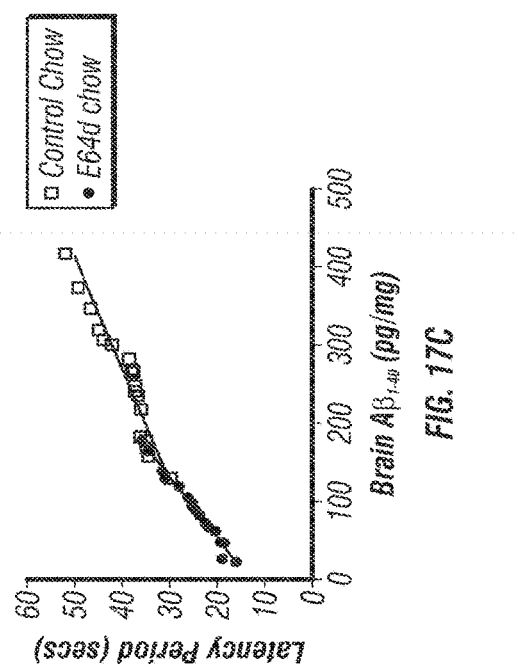
FIG. 17C
FIG. 17D

COMPOSITIONS AND METHODS FOR TREATING BETA-AMYLOID RELATED DISEASES

RELATED APPLICATIONS

This application is a continuation of U.S. utility patent application Ser. No. 12/910,747, filed Oct. 22, 2010 (now pending), which is a continuation of International Patent Application Serial No. PCT/US2010/044683, filed Aug. 6, 2010, which claims the benefit of priority under 35 U.S.C. § 119(e) of U.S. Provisional Patent Application Ser. No. 61/293,783, filed Jan. 11, 2010; U.S. Ser. No. 61/232,383, filed Aug. 7, 2009; and U.S. Ser. No. 61/232,388, filed Aug. 7, 2009. Each of the aforementioned applications are expressly incorporated herein by reference in their entirety and for all purposes.

GOVERNMENT RIGHTS

This invention was made with government support under grant number 4R44AG032784 awarded by the National Institutes of Health (NIH). The government has certain rights in the invention.

FIELD OF THE TECHNOLOGY

The invention generally relates to medicinal chemistry, veterinary medicine and cell biology. In alternative embodiments the invention provides compositions and methods for ameliorating diseases and conditions having a beta-amyloid component, including Alzheimer's disease (AD), Vascular Dementia (VD), dementia, pre-dementia, Cognitive Dysfunction Syndrome (CDS) and loss of cognition, in humans and in non-human animals. In alternative embodiments the invention provides analogs of AB-007 (E64d, or loxistatin) and its acid form E64c (loxistatin acid), their preparation, and pharmaceutical compositions thereof and methods of making and using same. In alternative embodiments compositions of the invention are deuterated analogs of AB-007 (or E64d or loxistatin) and E64c (or loxistatin acid). In alternative embodiments compositions of the invention are metabolically blocked forms as compared to AB-007 and loxistatin. In alternative embodiments compositions of the invention are used to ameliorate (including treat, slow, reverse or prevent) a disease or condition which can be ameliorated by partial or complete inhibition of a cysteine protease, e.g., Alzheimer's disease (AD), Vascular Dementia (VD), dementia, pre-dementia, Cognitive Dysfunction Syndrome (CDS) and loss of cognition in humans and in non-human animal. The invention also provides alternative dosage forms and formulations for AB-007 (E64d, loxistatin) and loxistatin acid (E64c), and for compounds of this invention.

BACKGROUND

AB-007 (also called loxistatin, E64d, EST or ((2S,3S)-trans-epoxysuccinyl-L-leucyl-amido-3-methylbutane ethyl ester) is an ethyl ester prodrug, 342.4 mol wt (MW), which is completely converted in vivo to its acid form E64c (also called loxistatin acid or Ep 475, 314.4 mol wt, which irreversibly inhibits proteases belonging to the cysteine protease class by covalently binding to sulfhydryl groups in the proteases' active sites.

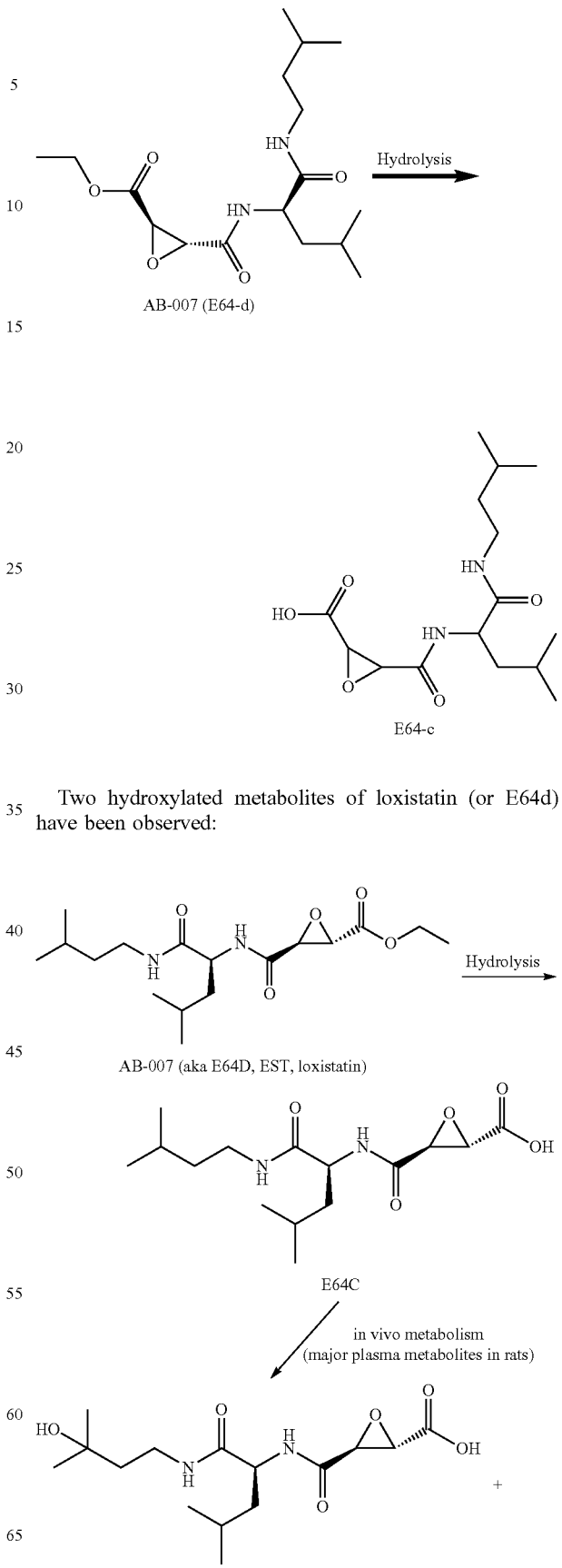

Two hydroxylated metabolites of loxistatin (or E64d) have been observed:

-continued

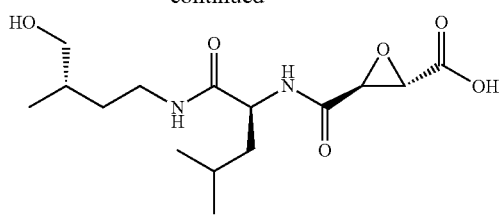

Reference: Fukushima, K. et al. "Metabolic fate of loxistatin in rat", *Xenobiotica*, 1990, 20, 1043-1051.

This metabolism, or in vivo hydroxylation, can result in lowering the effective concentration of the drug and shortens its half life in vivo.

Cathepsin B is co-localized with beta amyloid (Aβ) in plaques of AD brains and is elevated in cerebrospinal fluid (CSF) of Alzheimer Disease (AD) patients. Also, age-related changes in cathepsin B expression are consistent with the late age of onset of Alzheimer's. These findings, among others, indicate a role for cathepsin B in AD.

SUMMARY

In alternative embodiments the invention provides compositions and methods for treating, preventing, reversing, slowing the progression of and/or ameliorating diseases and conditions having a beta-amyloid (β-amyloid, or Aβ) component, including Alzheimer's disease (AD), Vascular Dementia (VD), dementia, pre-dementia, Cognitive Dysfunction Syndrome (CDS) and loss of cognition.

In alternative embodiments, the invention provides a compound of Formula I:

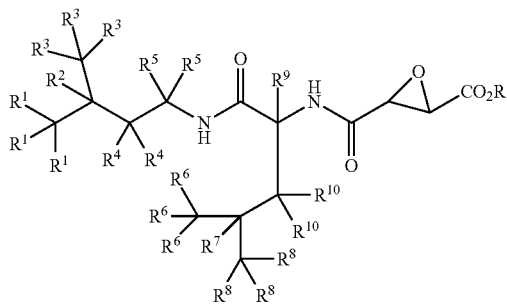

wherein

R is —H or alkyl;

each of $R^1$, $R^2$, $R^3$, $R^4$, $R^5$, $R^6$, $R^7$, $R^8$, $R^9$, and $R^{10}$ is independently selected from the group consisting of —H, -D, —F, —OH, and —CH$_3$;

or a pharmaceutically acceptable salt or solvate thereof; with the proviso that at least one of $R^1$, $R^2$, $R^3$, $R^4$, $R^5$, $R^6$, $R^7$, $R^8$, $R^9$, and $R^{10}$ is not —H.

In alternative embodiments, the compounds have the stereochemistry of Formula I':

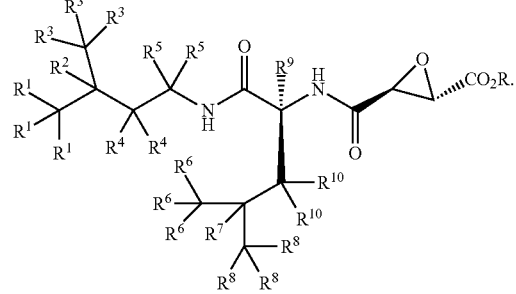

In alternative embodiments, each of $R^1$, $R^2$, $R^3$, $R^4$, $R^5$, $R^6$, $R^7$, $R^8$, $R^9$, and $R^{10}$ is independently selected from the group consisting of —H and -D. In alternative embodiments, each of $R^1$, $R^2$, $R^3$, $R^4$, and $R^5$, is —H and each of $R^6$, $R^7$, $R^8$, $R^9$, and $R^{10}$ is independently selected from the group consisting of —H and -D. In alternative embodiments, each of $R^1$, $R^2$, $R^3$, $R^4$, $R^5$, and $R^{10}$ is —H and each of $R^6$, $R^7$, $R^8$, and $R^9$ is independently selected from the group consisting of —H and -D. In alternative embodiments, each of $R^1$, $R^2$, $R^3$, $R^4$, $R^5$, $R^6$, $R^7$, $R^8$, $R^9$, and $R^{10}$ is independently selected from the group consisting of —H and —F. In alernative embodiments, each of $R^1$, $R^2$, $R^3$, $R^4$, $R^5$, and $R^{10}$ is —H and each of $R^6$, $R^7$, $R^8$, and $R^9$ is independently selected from the group consisting of —H and —F. In alternative embodiments, each of $R^1$, $R^2$, $R^3$, $R^4$, $R^5$, $R^6$, $R^7$, $R^8$, $R^9$, and $R^{10}$ is independently selected from the group consisting of —H and —OH. In alternative embodiments, each of $R^1$, $R^2$, $R^3$, $R^4$, $R^5$, and $R^{10}$ is —H and each of $R^6$, $R^7$, $R^8$, and $R^9$ is independently selected from the group consisting of —H and —OH. In alternative embodiments, each of $R^1$, $R^2$, $R^3$, $R^4$, $R^5$, $R^6$, $R^7$, $R^8$, $R^9$, and $R^{10}$ is independently selected from the group consisting of —H and —CH$_3$. In alternative embodiments, each of $R^1$, $R^2$, $R^3$, $R^4$, $R^5$, and $R^{10}$ is —H and each of $R^6$, $R^7$, $R^8$, and $R^9$ is independently selected from the group consisting of —H and —CH$_3$.

In alternative embodiments, the invention provides a compound selected from the group consisting of:

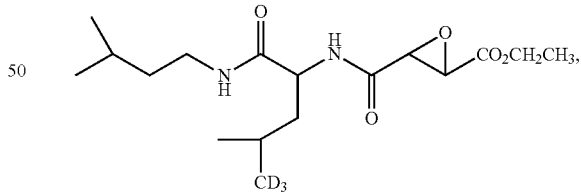

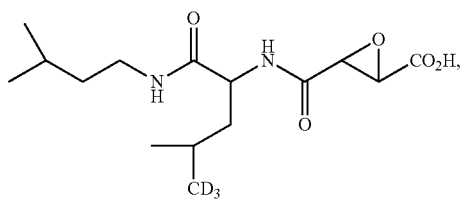

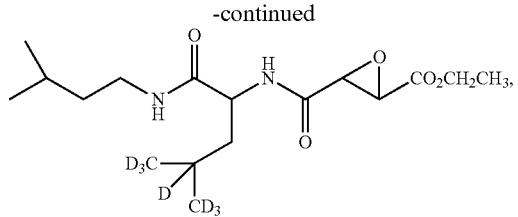
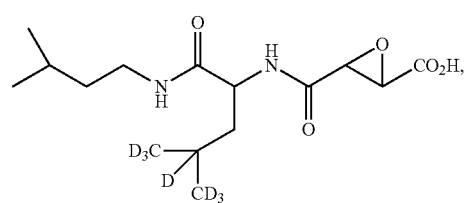
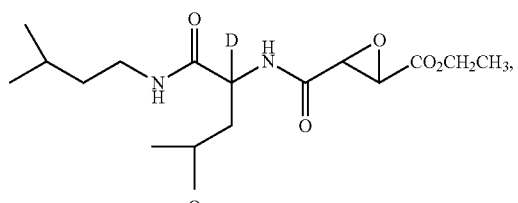
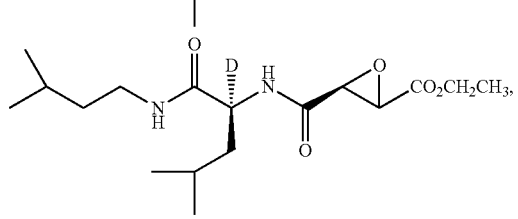
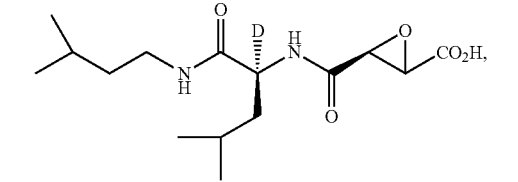
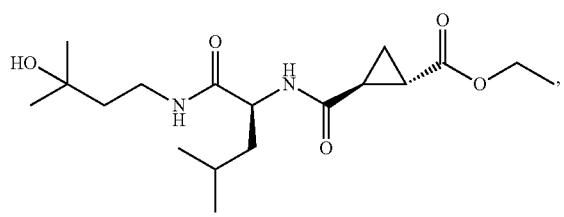
(ALP-###.###.01;
HLI-014-063)
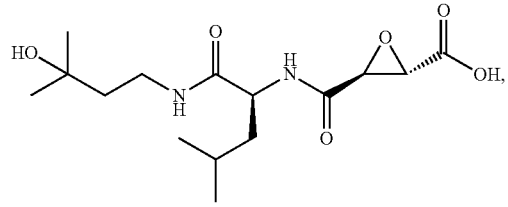
(ALP-485.000.01;
HLI-014-067)
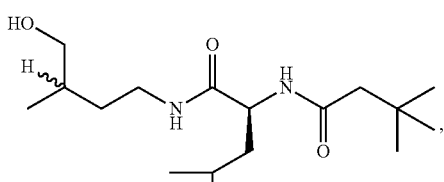
(AKA-016-141)
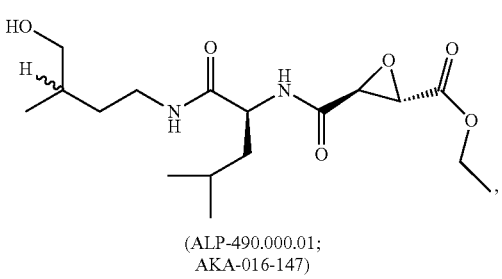
(ALP-490.000.01;
AKA-016-147)
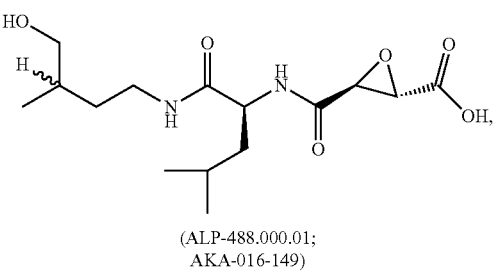
(ALP-488.000.01;
AKA-016-149)
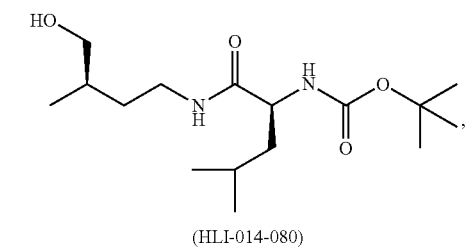
(HLI-014-080)
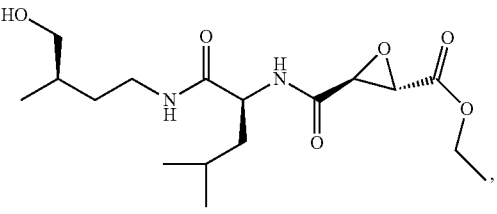
(ALP-493.000.01;
HLI-014-087)
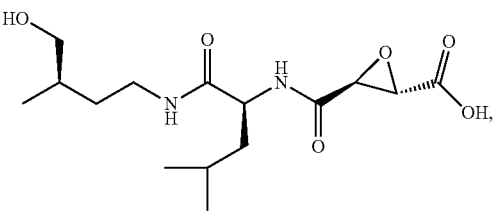
(ALP-494.000.01;
AKA-016-173)

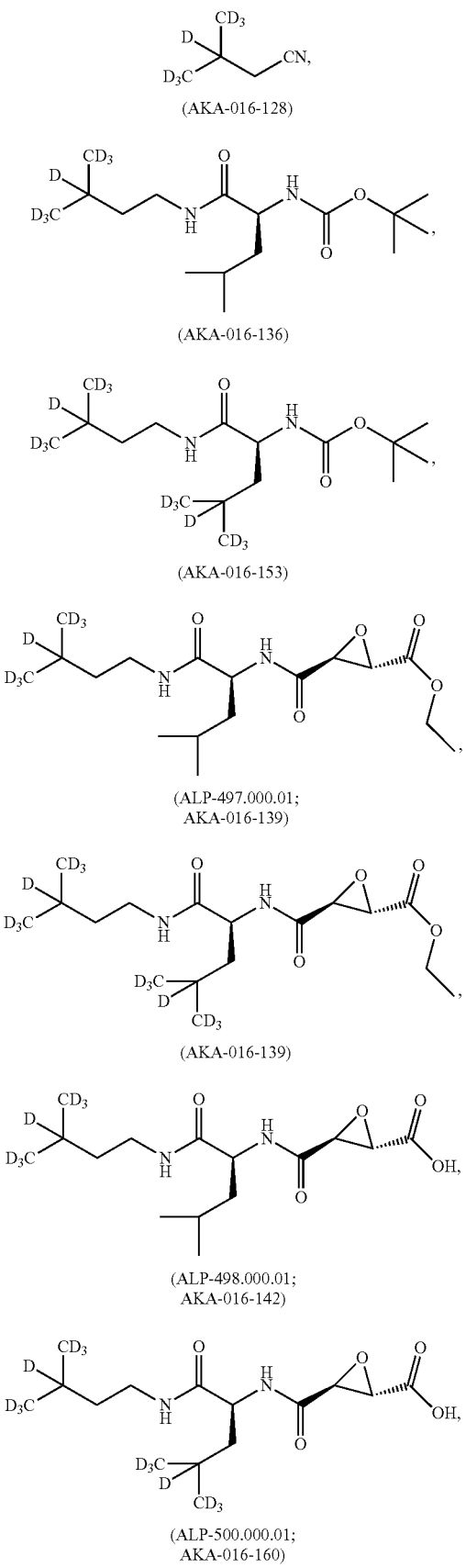
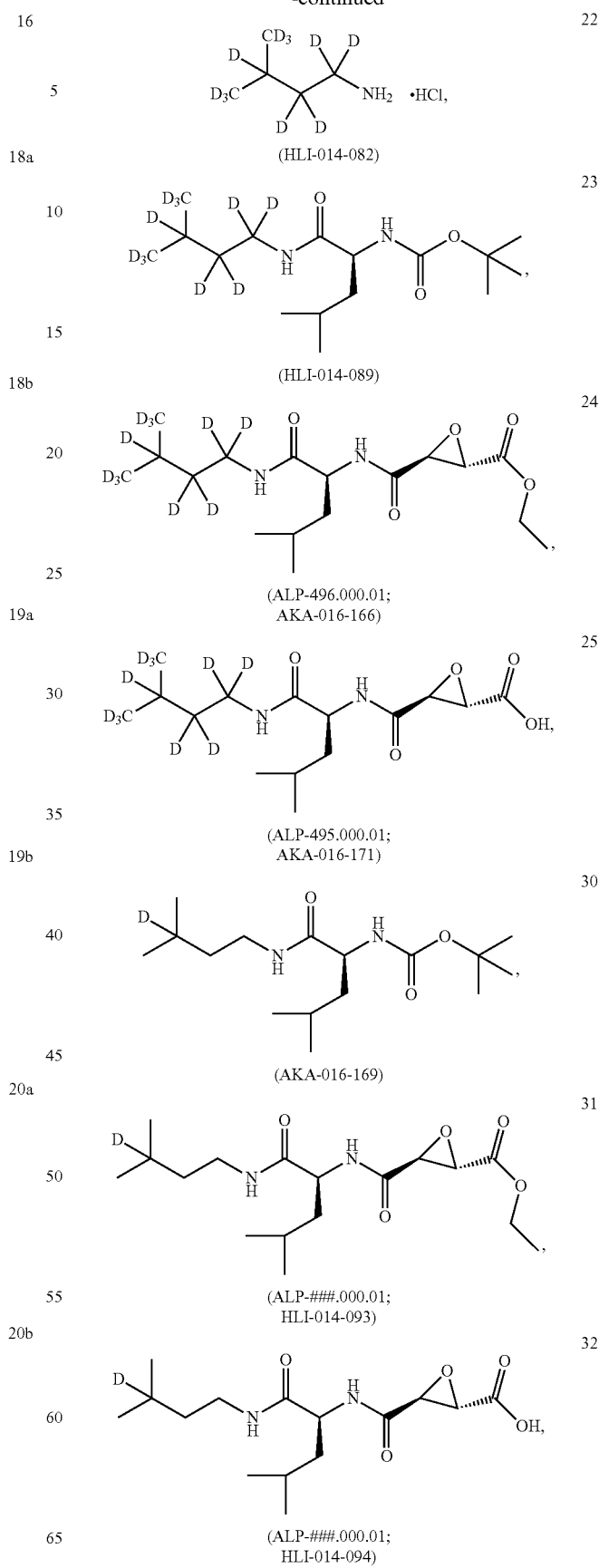

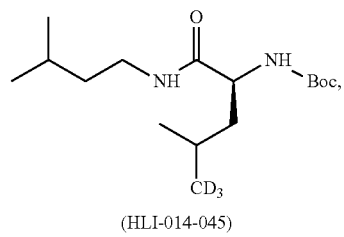
(HLI-014-045)
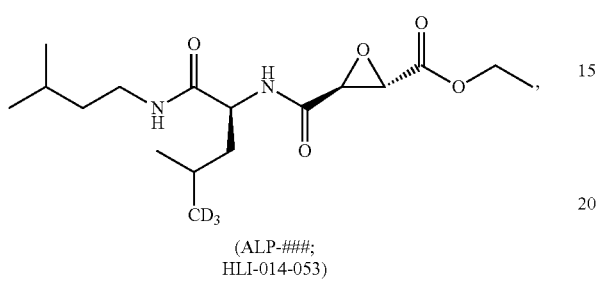
(ALP-###;
HLI-014-053)
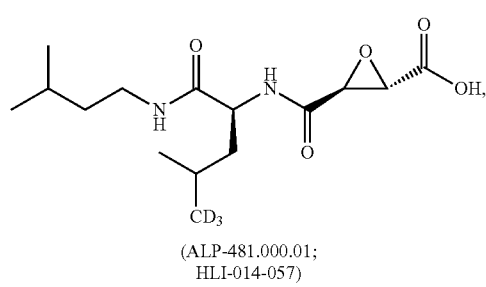
(ALP-481.000.01;
HLI-014-057)
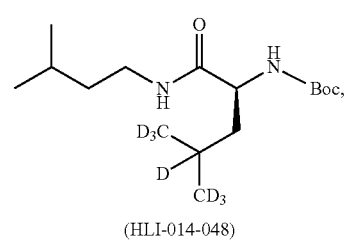
(HLI-014-048)
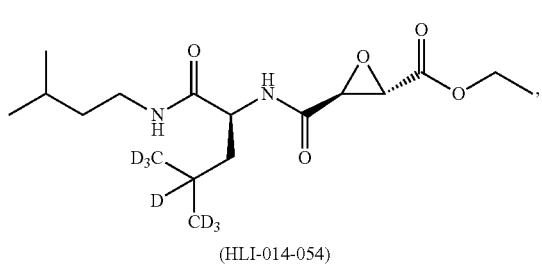
(HLI-014-054)
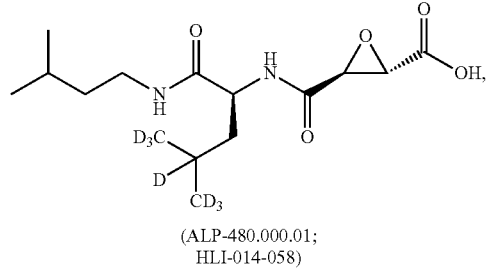
(ALP-480.000.01;
HLI-014-058)
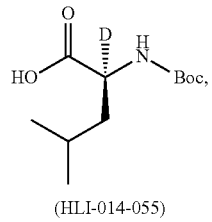
(HLI-014-055)
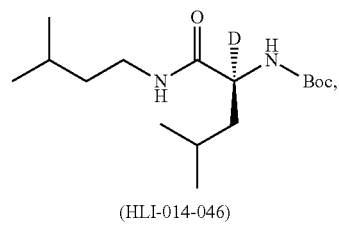
(HLI-014-046)
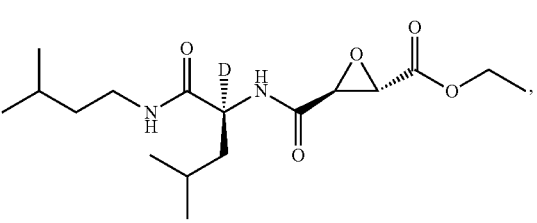
(HLI-014-059)
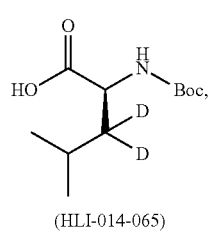
(ALP-479.000.01;
HLI-014-060)
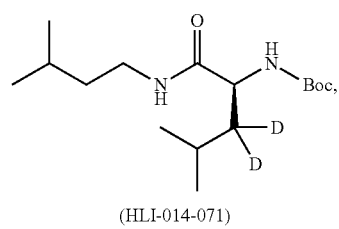
(HLI-014-065)
(HLI-014-071)

-continued

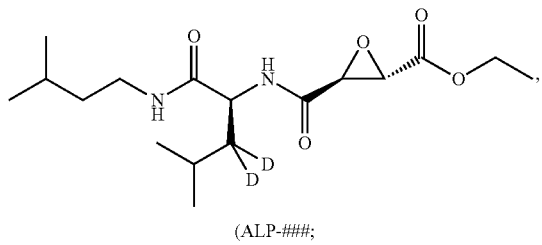

(ALP-###;
HLI-014-075)

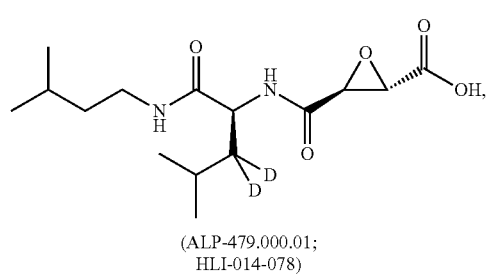

(ALP-479.000.01;
HLI-014-078)

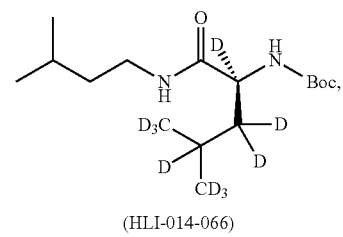

(HLI-014-066)

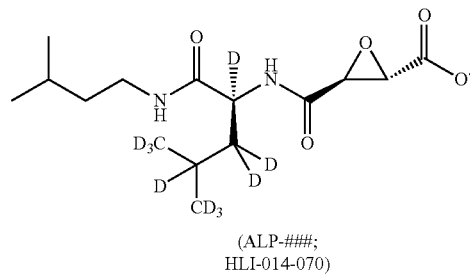

(ALP-###;
HLI-014-070)

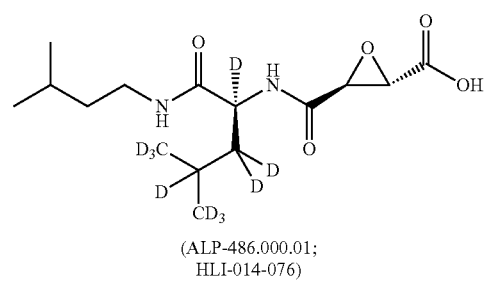

(ALP-486.000.01;
HLI-014-076)

or a pharmaceutically acceptable salts, hydrates, stereoisomers or solvates thereof.

In alternative embodiments, the invention provides a compound selected from the group consisting of:

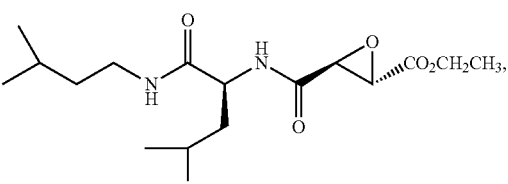

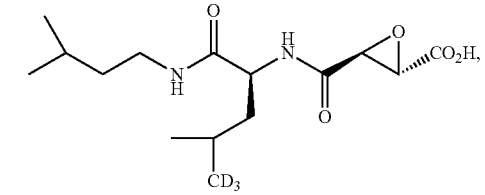

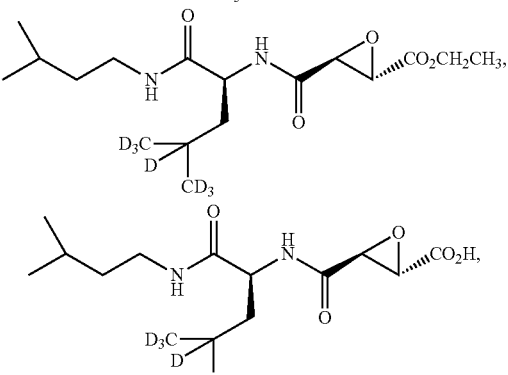

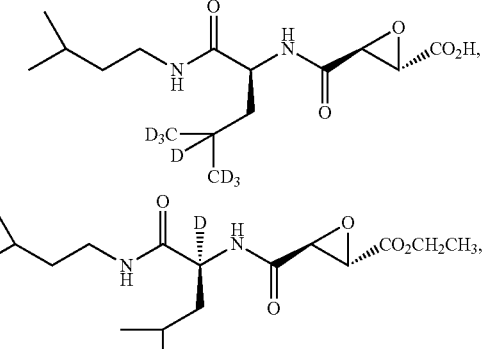

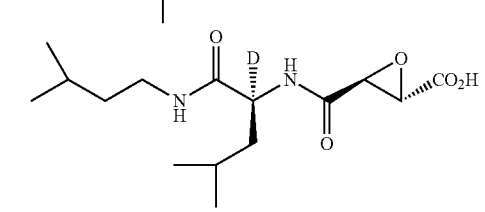

or a pharmaceutically acceptable salt, hydrate, stereoisomer or solvate thereof.

In alternative embodiments, the invention provides pharmaceutical compositions, dosage form or formulation comprising a therapeutically effective amount of a compound of the invention, or a pharmaceutically acceptable salt, hydrate, stereoisomer or solvate thereof, with a pharmaceutically acceptable carrier or excipient, and optionally the pharmaceutical composition, dosage form or formulation further comprises at least one other pharmaceutical composition, dosage form or formulation used to treat or ameliorate, or treat the symptoms of, or be palliative for, a cognitive dysfunction or a loss of cognition, a dementia or a pre-dementia, Alzheimer's disease (AD), Vascular Dementia (VD), and/or a Cognitive Dysfunction Syndrome (CDS) in humans or in a non-human animal, wherein optionally the at least one other pharmaceutical composition, dosage form or formulation comprises a selegiline (e.g., selegiline hydrochloride) or deprenyl, or ANIPRYL™; a donepezil (ARICEPT™); a carbamate; edrophonium or comparable reversible acetylcholinesterase inhibitor (e.g., TENSILON™, ENLON™, REVERSOL™); a neostigmine (e.g., PROSTIGMIN™, VAGOSTIGMIN™); a galantamine (e.g., NIVALIN™ RAZADYNE™, RAZADYNE ER™, REMINYL™); a rivastigmine (e.g., EXELON); a tarenflurbil or R-flurbiprofen (e.g., FLURIZAN™); and, any combination or equivalent thereof.

In alternative embodiments, of the pharmaceutical compositions, dosage forms or formulations, the composition is suitable for (or formulated for) topical, oral, parenteral, intrathecal or intravenous infusion administration, wherein optionally said composition is suitable for (or formulated for) administration as a (or in the form of a) patch, adhesive tape, gel, liquid or suspension, powder, spray, aerosol, lyophilate, lozenge, pill, geltab, tablet, capsule and/or implant. The pharmaceutical composition, dosage form or formulation can be suitable for (or formulated for) human or veterinary administration, wherein optionally said composition is suitable for (or formulated for) administration to a domestic, zoo, laboratory or farm animal, and optionally the animal is a dog or a cat.

In alternative embodiments, the invention provides methods of inhibiting a cysteine protease, or a cathepsin, a caspase or a calpain, or a cathepsin L or a cathepsin B, or a cathepsin F, H, K, L1, L2, O, S, W, X or Z, in an individual, a tissue, an organ or a cell, comprising contacting said cell, tissue, organ or individual with a compound of the invention, or a pharmaceutical composition, dosage form or formulation of the invention, or a compound of Formula I, wherein optionally the contacting is in vitro, ex vivo or in vivo, and optionally the individual is a human or a non-human animal, and optionally the individual or non-human animal is a domestic, zoo, laboratory or farm animal, and optionally the animal is a dog or a cat, and optionally the tissue, organ or cell comprises a muscle cell, a nerve cell, muscle tissue, peripheral nervous system (PNS) and/or central nervous system (CNS) or brain, and optionally by administering the compound or pharmaceutical composition, dosage form or formulation to the individual, a tissue, an organ or a cell a dementia or pre-dementia, a vascular dementia (VD) and/or an Alzheimer's disease (AD), is prevented, treated or ameliorated, and optionally the compound or pharmaceutical composition, dosage form or formulation is administered to prevent, treat or ameliorate pre-clinical Alzheimer's, a mild cognitive impairment and/or Alzheimer's dementia or pre-dementia.

In alternative embodiments, the invention provides methods of inhibiting a cysteine protease, or a cathepsin, a caspase or a calpain, or a cathepsin L or a cathepsin B, or a cathepsin F, H, K, L1, L2, O, S, W, X or Z, in an individual or a patient, comprising administering to said individual or patient in need thereof an effective amount of a compound of the invention, or a pharmaceutical composition, dosage form or formulation of the invention, or a compound of Formula I, wherein optionally the administering is ex vivo or in vivo, and optionally the individual is a human or a non-human animal, and optionally the individual or non-human animal is a domestic, zoo, laboratory or farm animal, and optionally the animal is a dog or a cat, and optionally the compound or pharmaceutical composition, dosage form or formulation is targeted to, or directly administered to (or into) a tissue, organ or cell, wherein optionally the tissue, organ or cell comprises a muscle cell, a nerve cell, muscle tissue, peripheral nervous system (PNS) and/or central nervous system (CNS) or brain, and optionally by administering the compound or pharmaceutical composition, dosage form or formulation the individual or patient is treated for (as a therapeutic or prophylactic treatment) a dementia or pre-dementia, a vascular dementia (VD) and/or an Alzheimer's disease (AD), and optionally the compound or pharmaceutical composition, dosage form or formulation is administered to prevent, treat or ameliorate pre-clinical Alzheimer's, a mild cognitive impairment and/or Alzheimer's dementia or pre-dementia.

In alternative embodiments, the invention provides methods for preventing, slowing the progression of, treating or ameliorating a cognitive impairment, a dementia or pre-dementia, a vascular dementia (VD) or an Alzheimer's disease (AD), comprising administering to an individual or a patient, comprising administering to said individual or patient in need thereof an effective amount of a compound of the invention, or a pharmaceutical composition, dosage form or formulation of the invention, or a compound of Formula I, wherein optionally the administering is ex vivo or in vivo, and optionally the individual is a human or a non-human animal, and optionally the individual or non-human animal is a domestic, zoo, laboratory or farm animal, and optionally the animal is a dog or a cat), and optionally the compound or pharmaceutical composition, dosage form or formulation is administered to prevent, treat or ameliorate pre-clinical Alzheimer's, a mild cognitive impairment and/or Alzheimer's dementia or pre-dementia.

In alternative embodiments, the invention provides methods of reversing, slowing, reducing or preventing the effects of β-amyloid in an individual or patient comprising administering to the individual or patient in need thereof an effective amount of a compound of the invention, or a pharmaceutical composition, dosage form or formulation of the invention, or a compound of Formula I, and optionally by reversing, slowing, reducing or preventing the effects of β-amyloid in the individual or patient, a dementia or pre-dementia, a vascular dementia (VD) and/or an Alzheimer's disease (AD), is treated or ameliorated, wherein optionally the administering is ex vivo or in vivo, and optionally the individual is a human or a non-human animal, and optionally the individual or non-human animal is a domestic, zoo, laboratory or farm animal, and optionally the animal is a dog or a cat, and optionally the compound or pharmaceutical composition, dosage form or formulation is administered to prevent, treat or ameliorate pre-clinical Alzheimer's, a mild cognitive impairment and/or Alzheimer's dementia or pre-dementia.

In alternative embodiments, the invention provides methods of reversing, slowing, reducing or preventing neuronal cell death or apoptosis in a cell, an organ, a tissue, an individual or a patient comprising administering to the cell or tissue, or the individual or patient in need thereof, an effective amount of a compound of the invention, or a pharmaceutical composition, dosage form or formulation of the invention, or a compound of Formula I, and optionally by reversing, slowing, reducing or preventing neuronal cell death or apoptosis in the cell, organ, tissue, individual or patient, a dementia or pre-dementia, a vascular dementia (VD) and/or an Alzheimer's disease (AD) is treated or ameliorated, wherein optionally the administering is ex vivo or in vivo, and optionally the individual is a human or a non-human animal, and optionally the individual or non-human animal is a domestic, zoo, laboratory or farm animal, and optionally the animal is a dog or a cat, and optionally the compound or pharmaceutical composition, dosage form or formulation is administered to prevent, treat or ameliorate pre-clinical Alzheimer's, a mild cognitive impairment and/or Alzheimer's dementia or pre-dementia.

In alternative embodiments, the invention provides methods of slowing, reversing, reducing or preventing neuronal cell death in an individual, subject or patient comprising (a) administering to said individual, subject or patient an effective amount of a compound comprising:

(i) a compound of the invention, or a pharmaceutical composition, dosage form or formulation of the invention, or a compound of Formula I; or (ii) a loxistatin (also called E64d or AB-007) (also called (2S,3S)-trans-epoxysuccinyl-L-leucyl-amido-3-methylbutane ethyl ester), or loxistatin acid (also called E64c) conjugated to (or comprising) a chemical delivery system (CDS); or a composition as described in U.S. Patent Application Nos. 20080227806, 20080176841 and/or 20100048717;

such that neuronal cell death is slowed, reversed, reduced and/or prevented, wherein said effective amount is between about 1 mg and about 400 mg; or is between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg;

(b) the method of (a), wherein the compound is formulated in a gel, spray, aerosol, powder, liquid or solid dosage form, or is formulated for administration as a (or in the form of a) patch, adhesive tape, gel, liquid or suspension, powder, spray, aerosol, lyophilate, lozenge, pill, geltab, tablet, capsule and/or implant;

(c) the method of (b), wherein the solid dosage form comprises an implant, a pill, a capsule, a geltab, a tablet or a lozenge; or (d) the method of (a), (b) or (c), wherein the compound is administered as a once a day, or twice a day (bid), or three times a day (tid) formulation, optionally as an oral dosage, and optionally the compound or pharmaceutical composition, dosage form or formulation is administered to prevent, treat or ameliorate a cognitive impairment, a dementia or pre-dementia, a vascular dementia (VD), an Alzheimer's disease (AD), or a pre-clinical Alzheimer's disease (AD), an Alzheimer's dementia or pre-dementia and/or a mild cognitive impairment;

and optionally the individual is a human or a non-human animal, and optionally the individual or non-human animal is a domestic, zoo, laboratory or farm animal, and optionally the animal is a dog or a cat.

In alternative embodiments, the invention provides methods of slowing, reversing, reducing or preventing the effects or formation of β-amyloid, or β-amyloid accumulation, or β-amyloid plaque formation in an individual, subject or patient comprising (a) administering to said individual, subject or patient an effective amount of a compound comprising:

(i) a compound of the invention, or a pharmaceutical composition, dosage form or formulation of the invention, or a compound of Formula I; or (ii) a loxistatin (also called E64d or AB-007) (also called (2S,3S)-trans-epoxysuccinyl-L-leucyl-amido-3-methylbutane ethyl ester), or loxistatin acid (also called E64c) conjugated to (or comprising) a chemical delivery system (CDS); or a composition as described in U.S. Patent Application Nos. 20080227806, 20080176841 and/or 20100048717;

such that the effects or formation of β-amyloid, or β-amyloid accumulation, or β-amyloid plaque formation is slowed, reversed, reduced and/or prevented, wherein said effective amount is between about 1 mg and about 400 mg; or is between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg;

(b) the method of (a), wherein the compound is formulated in a gel, spray, aerosol, powder, liquid or solid dosage form, or is formulated for administration as a (or in the form of a) patch, adhesive tape, gel, liquid or suspension, powder, spray, aerosol, lyophilate, lozenge, pill, geltab, tablet, capsule and/or implant;

(c) the method of (b), wherein the solid dosage form comprises an implant, a pill, a capsule, a geltab, a tablet or a lozenge; or (d) the method of (a), (b) or (c), wherein the compound is administered as a once a day, or a twice a day (bid), or a three times a day (tid) formulation, optionally as an oral dosage, and optionally the compound or pharmaceutical composition, dosage form or formulation is administered to prevent, treat or ameliorate a cognitive impairment, a dementia or pre-dementia, a vascular dementia (VD), an Alzheimer's disease (AD) or a pre-clinical Alzheimer's disease (AD), a mild cognitive impairment and/or Alzheimer's dementia or pre-dementia, and optionally the individual is a human or a non-human animal, and optionally the individual or non-human animal is a domestic, zoo, laboratory or farm animal, and optionally the animal is a dog or a cat.

In alternative embodiments, the invention provides methods of slowing, reversing, reducing or preventing a cognitive impairment, a dementia, an Alzheimer's Disease (AD), a vascular dementia (VD) and/or an Alzheimer's dementia or pre-dementia, in an individual, subject or patient comprising (a) administering to said individual, subject or patient an effective amount of a compound comprising:

(i) a compound of the invention, or a pharmaceutical composition, dosage form or formulation of the invention, or a compound of Formula I; or (ii) a loxistatin (also called E64d or AB-007) (also called (2S,3S)-trans-epoxysuccinyl-L-leucyl-amido-3-methylbutane ethyl ester), or loxistatin acid (also called E64c) conjugated to (or comprising) a chemical delivery system (CDS); or a composition as described in U.S. Patent Application Nos. 20080227806, 20080176841 and/or 20100048717;

such that the cognitive impairment, AD, VD, dementia or pre-dementia, is slowed, reversed, reduced and/or prevented, wherein said effective amount is between about 1 mg and about 400 mg; or is between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg;

(b) the method of (a), wherein the compound is formulated in a gel, spray, aerosol, powder, liquid or solid dosage form, or is formulated for administration as a (or in the form of a) patch, adhesive tape, gel, liquid or suspension, powder, spray, aerosol, lyophilate, lozenge, pill, geltab, tablet, capsule and/or implant;

(c) the method of (b), wherein the solid dosage form comprises an implant, a pill, a capsule, a geltab, a tablet or a lozenge; or (d) the method of (a), (b) or (c), wherein the compound is administered as a once a day, or a twice a day (bid), or a three times a day (tid) formulation, optionally as an oral dosage, and optionally the compound or pharmaceutical composition, dosage form or formulation is administered to prevent, treat or ameliorate a cognitive impairment, a dementia or pre-dementia, a vascular dementia (VD), Alzheimer's disease (AD), or a pre-clinical Alzheimer's, a mild cognitive impairment and/or Alzheimer's dementia or pre-dementia, and optionally the individual is a human or a non-human animal, and optionally the individual or non-human animal is a domestic, zoo, laboratory or farm animal, and optionally the animal is a dog or a cat.

In alternative embodiments, the invention provides methods of slowing, reversing, reducing or preventing a Cognitive Dysfunction Syndrome (CDS) in a non-human animal, e.g., dogs and cats, including Canine Cognitive Dysfunction (CCD), comprising (a) administering to said individual, subject or patient an effective amount of a compound comprising an inhibitor of a cysteine protease, or a cathepsin, a caspase or a calpain, or a cathepsin L or a cathepsin B, or a cathepsin F, H, K, L1, L2, O, S, W, X or Z, in an individual, a tissue, an organ or a cell, wherein optionally the inhibitor comprises:

(i) a compound of the invention, or a pharmaceutical composition, dosage form or formulation of the invention, or a compound of Formula I;

(ii) a loxistatin (also called E64d or AB-007) (also called (2S,3S)-trans-epoxysuccinyl-L-leucyl-amido-3-methylbutane ethyl ester), or loxistatin acid (also called E64c) conjugated to (or comprising) a chemical delivery system (CDS); or a composition as described in U.S. Patent Application Nos. 20080227806, 20080176841 and/or 20100048717;

(iii) an odanacatib or MK-0674, or equivalents thereof;

(iv) a diazomethyl ketone, a fluoromethyl ketone, an acyloxymethyl ketone, an O-acylhydroxylamine or a vinyl sulfone, or equivalents thereof; and/or (v) a reversible hydrazide inhibitor of cathepsin B comprising a ZLIII115A and ZLIII43A, or equivalents thereof;

(vi) a cystatin, or a cystatin A, cystatin B, cystatin C (or cystatin 3) or cystatin D, or a type 1 cystatin (a stefin), a type 2 cystatin or a kininogen;

wherein optionally the Cognitive Dysfunction Syndrome (CDS) is slowed, reversed, reduced and/or prevented, wherein said effective amount is between about 1 mg and about 400 mg; or is between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg;

(b) the method of (a), wherein the compound is formulated in a gel, spray, aerosol, powder, liquid or solid dosage form, or is formulated for administration as a (or in the form of a) patch, adhesive tape, gel, liquid or suspension, powder, spray, aerosol, lyophilate, lozenge, pill, geltab, tablet, capsule and/or implant;

(c) the method of (b), wherein the solid dosage form comprises an implant, a pill, a capsule, a geltab, a tablet or a lozenge; or (d) the method of (a), (b) or (c), wherein the compound is administered as a once a day, or a twice a day (bid), or a three times a day (tid) formulation, optionally as an oral dosage, and optionally the individual is a human or a non-human animal, and optionally the individual or non-human animal is a domestic, zoo, laboratory or farm animal, and optionally the animal is a dog or a cat, and optionally CDS encompasses a Canine Cognitive Dysfunction (CCD).

In alternative embodiments, the invention provides products of manufacture, e.g., provides a blister pack or a plurality of blister packettes, a blister package, a lidded blister or a blister card or packet, a clamshell, a tray or a shrink wrap, or a paper, plastic or cellophane package or a plurality of packettes, comprising:

(a) a compound of the invention, or a pharmaceutical composition, dosage form or formulation of the invention, and/or a compound of Formula I; and (b) at least one other (e.g., at least one additional, different) compound, pharmaceutical composition, dosage form or formulation of (a), wherein the at least one other (e.g., at least one additional, different) compound, pharmaceutical composition, dosage form or formulation is used to treat or ameliorate, or treat the symptoms of, or be palliative for: a cognitive dysfunction or a loss of cognition, a dementia or a pre-dementia, Alzheimer's disease (AD), Vascular Dementia (VD), and/or a Cognitive Dysfunction Syndrome (CDS), in humans or in a non-human animal, wherein optionally the at least one other pharmaceutical composition, dosage form or formulation comprises a selegiline (e.g., selegiline hydrochloride) or deprenyl, or ANIPRYL™; a donepezil (ARICEPT™); a carbamate; edrophonium or comparable reversible acetylcholinesterase inhibitor (e.g., TENSILON™, ENLON™, REVERSOL™); a neostigmine (e.g., PROSTIGMIN™, VAGOSTIGMIN™); a galantamine (e.g., NIVALIN™ RAZADYNE™, RAZADYNE ER™, REMINYL™); a rivastigmine (e.g., EXELON); a tarenflurbil or R-flurbiprofen (e.g., FLURIZAN™); and, any combination or equivalent thereof, or a nutritional supplement or a vitamin, e.g., vitamin E, vitamin B12 or a folic acid supplement, or any equivalent or combination thereof, or a pain treatment or pain palliative or an anti-inflammatory drug, e.g., an ibuprofen (e.g., ADVIL™, MOTRIN™), naproxen sodium (ALEVE™), indomethacin (INDOCIN™), or any equivalent or combination thereof, or a non-steroidal anti-inflammatory drug (a NSAID), e.g., a cyclooxygenase (COX) (or prostaglandin synthase) inhibitor, e.g., an etodolac (e.g., LODINE™, LODINE SR™ or ECCOXOLAC™), naproxen, celecoxib, rofecoxib, etoricoxib, valdecoxib, parecoxib, nabumetone, diclofenac, lumiracoxib, or equivalent, or a neuropathic pain analgesic such as gabapentin or pregabalin.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 6(A) brain Aβ(40), FIG. 6(B) brain Aβ(42), FIG. 6(C) CSF ΔP, FIG. 6(D) CSF Aβ(42), FIG. 6(E) plasma Aβ(40) and FIG. 6(F) plasma Aβ(42), as discussed in detail in Example 9, below.

FIG. 7A that once-a-day for one week oral administration of AB-007 (E64d, loxistatin) to guinea pigs results in a dose response reduction brain cathepsin B activity; FIG. 7(B) (lower graph) illustrates that the same treatment results in an increase in brain BACE1 activity, as discussed in detail in Example 9, below.

FIG. 8A, FIG. 8B, FIG. 8C and FIG. 8D graphically illustrate data showing paired guinea pig data for brain Aβ(40) or Aβ(42) versus (vs) brain cathepsin B or BACE1 activity, respectively for the combined AB-007 (E64d, loxistatin) dose groups: FIG. 8(A) Brain Aβ(40) vs brain cathepsin B activity shows a significant positive correlation, showing that brain cathepsin B inhibition reduces brain Aβ(40); FIG. 8(B) Brain Aβ(42) vs brain cathepsin B activity also has a significant positive correlation, showing brain cathepsin B inhibition reduces brain Aβ(42); FIG. 8(C): Brain Aβ(40) vs brain BACE1 activity demonstrates a small negative correlation; and, FIG. 8(D) Brain Aβ(42) vs brain BACE1 activity has a negative correlation, as discussed in detail in Example 9, below.

FIG. 9(A) Brain Aβ(40) vs Aβ(42) shows a significant positive correlation; and, FIG. 9(B) Brain cathepsin B vs BACE1 activity shows a slight negative correlation, as discussed in detail in Example 9, below.

FIG. 11A (upper graph) graphically illustrate data showing that once-a-day oral administration of E64d7 to guinea pigs results in a dose response reduction of brain cathepsin B activity, which is similar to the biphasic lowering of Aβ; FIG. 11B (lower graph) graphically illustrates data showing that same treatment results in an increase in brain BACE1 activity, as discussed in detail in Example 9, below.

FIG. 12(A) Brain Aβ(40) vs brain cathepsin B activity shows a significant positive correlation; FIG. 12(B) Brain Aβ(42) vs brain cathepsin B activity also has a significant positive correlation; FIG. 12(C) Brain Aβ(40) vs brain BACE1 activity demonstrates a small negative correlation; FIG. 12(D) Brain Aβ(42) vs brain BACE1 activity has a negative correlation, as discussed in detail in Example 9, below.

FIG. 13(A) (upper graph) Brain Aβ(40) vs Aβ(42) shows a significant positive correlation; FIG. 13(B) Brain cathepsin B vs BACE1 activity shows a slight negative correlation, as discussed in detail in Example 9, below.

FIG. 14(A) Feeding the E64d doped chow for 1 or 3 months caused a significant reduction in brain Aβ(40) in both the young and old mice relative to age-matched controls; FIG. 14(B) the E64d doped chow fed for 1 or 3 months also caused a significant reduction in brain Aβ(42) in both the young and old mice relative age-matched controls, as discussed in detail in Example 9, below.

FIG. 15A, FIG. 15B, FIG. 15C and FIG. 15D graphically compares the data shown in FIG. 14, for brain Aβ(40) and Aβ(42) levels in young and old animals feed E64d doped chow for 1 or 3 months: FIG. 15(A) The brain Aβ(40) data from 1 month feeding; FIG. 15(B) the brain Aβ(40) data from 3 month feeding; FIG. 15(C) the brain Aβ(42) data from 1 month feeding; FIG. 15(D) the brain Aβ(42) data from 3 month feeding are shown, as discussed in detail in Example 9, below.

FIG. 17A, FIG. 17B, FIG. 17C, and FIG. 17D graphically illustrate data showing a paired data analysis from the mouse experiments between brain Aβ(40) or Aβ(42) peptides and latency period for young and old mice either treated or not with AB-007 (E64d, loxistatin): FIG. 17(A) graphically illustrates the effect of feeding young mice either the control or E64d-doped chow for 1 month on brain Aβ(40) peptide and latency period is shown; FIG. 17(B) graphically illustrates the effect of the E64d-doped chow feeding on young animals on brain Aβ(42) peptide vs. latency period is shown; FIG. 17(C) graphically illustrates the effect of the E64d-doped chow feeding on old animals on brain Aβ(40) peptide and latency period is shown; FIG. 17(D) graphically illustrates the effect of the E64d-doped chow feeding on old animals on brain Aβ(42) and latency period is shown; as discussed in detail in Example 9, below.

Like reference symbols in the various drawings indicate like elements.

DETAILED DESCRIPTION

Figure 1:
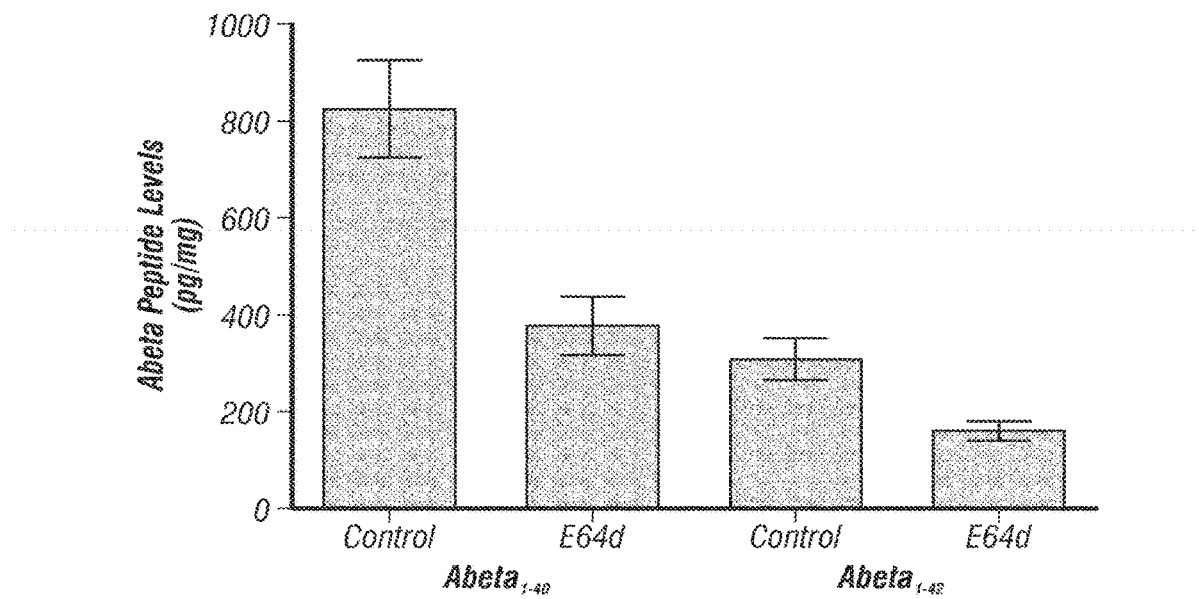
FIG. 1 graphically illustrates data showing the measurement of brain $A\beta_{40}$ and $A\beta_{42}$ for 10 mg/kg/day dosing after 7 days compared to vehicle treated controls, as discussed in detail in Example 8, below.

In alternative embodiments the invention provides compositions and methods for preventing, treating, slowing the progress of, reversing or ameliorating diseases and conditions having a beta-amyloid component, including cognitive dysfunctions and loss of cognition, dementias and pre-dementias, Alzheimer's disease (AD), Vascular Dementia (VD), and Cognitive Dysfunction Syndrome (CDS) in humans or in a non-human animal.

In alternative embodiments the invention provides analogs of AB-007 (also called loxistatin or E64d) and its acid form E64c (also called loxistatin acid), their preparation, and pharmaceutical compositions thereof and methods of making and using same. In alternative embodiments, AB-007 (loxistatin) and/or E64c (loxistatin acid) are derivatized, e.g. deuterated, in one or more sites, e.g., a site relevant to a metabolic site, e.g., a site on the molecule involved and/or altered (e.g., hydroxylated) in its metabolism or breakdown in vivo. In alternative embodiments, the derivatization, e.g., a deuteration, results in altered metabolism, e.g., slowed or blocked metabolism, of a composition of the invention. Thus, in alternative embodiment compositions of the invention have "better" pharmacokinetic properties than the "parent" AB-007 (loxistatin, E64d) or E64c (loxistatin acid), e.g., because (noting the invention is not limited by any particular mechanism of action) the derivatization slows or inhibits the hydroxylation of AB-007 or E64c, a lower dosage is effective and/or more potent and an individual can be given a lower dosage to produce the same effect from a comparative dosage and/or formulation of the "parent" AB-007 or E64c.

In one embodiment, to block or slow the drug's (a composition of the invention) metabolism, e.g., hydroxylation, one or more hydrogen atoms extracted in the in vivo metabolic process and/or otherwise involved in the metabolic process is substituted by a moiety which is more difficult to (e.g., enzymatically) remove, e.g., deuterium. In alternative embodiments, one or more selected hydrogens are substituted (replaced) with a hydroxyl, deuterium, fluorine or a methyl group or a combination thereof.

For example, in alternative embodiments, compositions of the invention comprise a hepta-deuterated (or 7-position deuterated) AB-007 (loxistatin, E64d) and a hepta-deuterated (or 7-position deuterated) loxistatin acid (E64c):

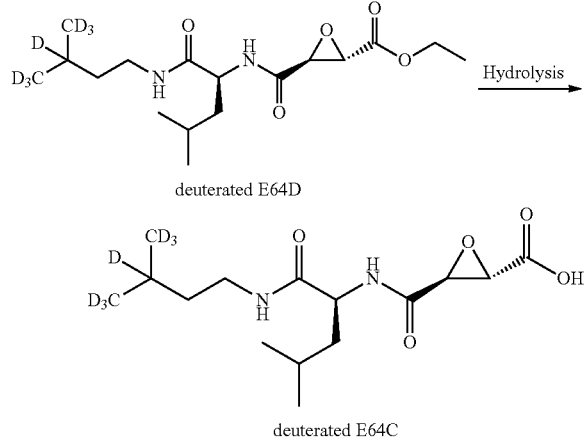

(the above illustrated isoform of hepta-deuterated (or 7-position deuterated) AB-007 (loxistatin, E64d) is designated "E64d7" (see, e.g., Example 9, below), and the above illustrated isoform of hepta-deuterated (or 7-position deuterated) E64c (or loxistatin acid) is designated "E64c7").

In alternative embodiments, compositions of the invention also comprise a 1-, 2-, 3-, 4-, 5-, 6- and/or 7-position substitutions with e.g., a deuterium and/or a fluorine, as alternative embodiments to the hepta-deuterated (or 7-position deuterated) species of the invention. While the invention is not limited by any particular mechanism of action, these alternative embodiments are based on the observed two hydroxylated metabolites of AB-007 (loxistatin, E64d), as illustrated above e.g., in the hepta-deuterated isoform designated "E64d7" and "E64c7".

In alternative embodiments the invention provides compositions comprising Formula I, which illustrates compounds of the invention resulting from these described substitutions:

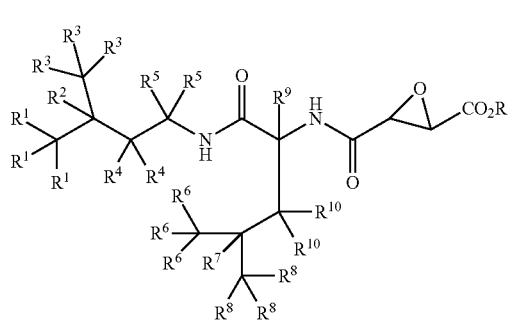

wherein
R is —H or alkyl;
each of $R^1$, $R^2$, $R^3$, $R^4$, $R^5$, $R^6$, $R^7$, $R^8$, $R^9$, and $R^{10}$ is independently selected from the group consisting of —H, -D, —F, —OH, —CH$_3$ and/or a pharmaceutically acceptable salt, hydrate, stereoisomer, or solvate thereof; with the proviso that at least one of $R^1$, $R^2$, $R^3$, $R^4$, $R^5$, $R^6$, $R^7$, $R^8$, $R^9$, and $R^{10}$ is not hydrogen (—H).

For example, alternative embodiments of the invention comprise both ester and acid forms (e.g., E64c and E64c (loxistatin acid) forms, respectively) comprising or consisting of, in addition to the illustrated deuterated embodiments, including the hepta-deuterated embodiments (where e.g. all $R^1$, $R^2$, $R^3$ positions can be deuterated or otherwise substituted), alternative exemplary species can have only $R^1$ and $R^3$ positions completely or partially deuterated or otherwise substituted, or only $R^1$ positions completely or partially deuterated or otherwise substituted, or only $R^3$ positions completely or partially deuterated or otherwise substituted, or only the $R^2$ position deuterated or otherwise substituted, or a combination of the $R^1$ and $R^2$ or $R^2$ and $R^3$ positions completely or partially deuterated or otherwise substituted, and the like.

Alternative embodiments of the invention comprise derivatized analogs, e.g., metabolically blocked or otherwise altered derivatives, of AB-007 (loxistatin, E64d) and loxistatin acid (E64c), including deuterated, hydroxylated, fluorinated or methylated analogs or derivatives, or any combination thereof.

With regard to deuterated compounds of the invention, including those of Formula I, it will be recognized that some variation of natural isotopic abundance occurs in a synthesized compound depending upon the origin of chemical materials used in the synthesis. Thus, a preparation of AB-007 (loxistatin, E64d) or loxistatin acid (E64c) will inherently contain small amounts of deuterated isotopologues. The concentration of naturally abundant stable hydrogen and carbon isotopes, notwithstanding this variation, is small and immaterial as compared to the degree of stable isotopic substitution of compounds of this disclosure.

See, for instance, Wada E et al., *Seikagaku* 1994, 66:15; Ganes L Z et al., *Comp Biochem Physiol Mol Integr Physiol* 1998, 119:725. Accordingly, for compounds and compositions of this invention, which include pharmaceutical preparations and formulations, when a particular position is designated as having deuterium ("-D"), it is understood that the abundance of deuterium at that position is greater than, or substantially greater than, the natural abundance of deuterium, which is 0.015%. For example, alternative embodiments of the invention comprise analogs of AB-007 (loxistatin, E64d) and/or loxistatin acid (E64c) having greater than 0.02%, or greater than about 0.1% deuterium. In one embodiment, the deuterium substitution, or "enrichment", occurs at a specific position or positions. In one embodiment, the deuterium enrichment is no less than about 1%. In a further embodiment, the deuterium enrichment is no less than about 10%. In a further embodiment, the deuterium enrichment is no less than about 20%. In a further embodiment, the deuterium enrichment is no less than about 50%. In a further embodiment, the deuterium enrichment is no less than about 70%. In a further embodiment, the deuterium enrichment is no less than about 80%. In a further embodiment, the deuterium enrichment is no less than about 90%. In a further embodiment, the deuterium enrichment is no less than about 95%. In one embodiment, the deuterated (or otherwise substituted) compound of the invention has a slower rate of metabolism, e.g., slower rate of hydroxylation, than a corresponding protonated (non-deuterated, non-substituted) compound.

Unless defined otherwise, all technical and scientific terms used herein have the same meaning as commonly understood by those of ordinary skill in the art to which this application pertains. The following definitions are provided to assist the reader in the practice of the application.

Unless defined otherwise, all technical and scientific terms used herein have the same meaning as commonly understood by one of ordinary skill in the art to which the application pertains. Although any methods and materials similar or equivalent to those described herein can be used in the practice for testing of the disclosure of the present application, materials and methods typically employed are described herein.

In alternative embodiments, the terms "alkyl" and "substituted alkyl" are interchangeable and include substituted, optionally substituted and unsubstituted $C_1$ to $C_{12}$, or longer, straight chain (a linear $C_1$, $C_2$, $C_3$, $C_4$, $C_5$, $C_6$, $C_7$, $C_8$, $C_9$, $C_{10}$, $C_{11}$ or $C_{1-12}$ or longer carbon chain), or branched saturated aliphatic hydrocarbon groups, substituted, optionally substituted and unsubstituted $C_1$ to $C_{12}$ straight chain (or longer) or branched unsaturated aliphatic hydrocarbon groups. The invention also comprises compound comprising substituted, optionally substituted and unsubstituted $C_3$ to $C_8$, or $C_4$ to $C_8$ or $C_5$ to $C_8$ cyclic saturated aliphatic hydrocarbon groups, substituted, optionally substituted and unsubstituted $C_3$ to $C_8$, or $C_4$ to $C_8$ or $C_5$ to $C_8$ cyclic unsaturated aliphatic hydrocarbon groups having the specified number of carbon atoms. In alternative embodiments, the definition of "alkyl" includes but is not limited to: methyl (Me), trideuteromethyl (—CD3), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl or hydrogen substituents can be independently selected from the group consisting of deuterium, halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C1-10alkylthio, arylC$_{0-10}$alkylthio, C$_{1-10}$alkylamino, arylC$_{0-10}$alkylamino, N-aryl-N—C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOORA and —C$_{0-10}$alkylCONR$^B$R$^C$ wherein R$^A$, R$^B$ and R$^C$ are independently selected from the group consisting of hydrogen, deuterium, alkyl, aryl.

In alternative embodiments, a composition of the invention, including a pharmaceutical composition of the invention, can be administered to any patient, individual or "subject", including any mammal, such as human patients and non-human primates, as well as experimental animals such as rabbits, rats, and mice, and other animals. Animals include all vertebrates, e.g., mammals and non-mammals, such as dogs, cats, sheep, cows, pigs, rabbits, chickens, including any domestic, farm or zoo animals, and etc. Subjects for practicing the therapeutic methods of this invention can be human patients. In alternative embodiments compositions of the invention are administered to individuals or subjects, e.g., patients, to ameliorate (including treat, slow, reverse or prevent) a disease or condition which can be ameliorated by partial or complete inhibition of a cysteine protease, e.g., a dementia or pre-dementia, a cognitive loss, Alzheimer's disease (AD) or a vascular dementia (VD) or Cognitive Dysfunction Syndrome (CDS) in a non-human animal.

In alternative embodiments, patients, individuals or subjects treated using compositions and methods of the invention include those already suffering from a dementia or pre-dementia, or suspected from suffering from a dementia or pre-dementia, or a partial loss of cognition, as well as those prone to developing a dementia or pre-dementia, e.g., Alzheimer's disease (AD), a vascular dementia (VD) or Cognitive Dysfunction Syndrome (CDS) in a non-human animal. For example, in one embodiment, patients, individuals or subjects (including humans and animals, e.g., dogs and cats) treated using compositions and methods of the invention are asymptomatic but have been diagnosed as pre-conditional or predisposed to AD or a dementia or pre-dementia because of a genetic test, family history and/or brain or body scan (e.g., PET or CAT) detection of central nervous system (CNS, e.g., brain) plaques, e.g., plaques comprising beta amyloid.

In alternative embodiments, "treating" or "ameliorating" includes e.g. one or more of (i) preventing any cognitive loss or dementia or pre-dementia (e.g., AD or pre-dementia or vascular dementia, or VD) from occurring (e.g. prophylaxis); (ii) inhibiting any cognitive loss or dementia or pre-dementia or arresting or slowing or reversing its development or progress; and (iii) relieving one or more symptoms, e.g., loss of cognition or memory, associated with a dementia or pre-dementia or AD. In alternative embodiments, "treatment" includes the administration of the compositions or dosage forms of this invention, and practicing the methods of this invention, to prevent or delay the onset of the symptoms, complications, or biochemical indicia of a dementia or pre-dementia, such as AD, VD and Cognitive Dysfunction Syndrome (CDS) in a non-human animal, alleviating or ameliorating the symptoms of a dementia or pre-dementia, AD, VD and/or CDS, or reversing or arresting or inhibiting further development of the disease. In alternative embodiments, "treatment" further refers to any indicia of success in the treatment or amelioration or prevention or reversal of a dementia or pre-dementia, AD, VD and/or CDS, or a related pathological process (e.g., neuronal or muscle death), including any objective or subjective parameter such as abatement; remission; diminishing of symptoms or making the disease condition more tolerable to the patient; slowing in the rate of degeneration or decline; or making the final point of degeneration less debilitating. Detailed procedures for the treatment or amelioration of a dementia or pre-dementia, AD, VD and/or CDS, or symptoms thereof can be based on objective or subjective parameters, including the results of an examination by a physician, a cognitive or psychological test, a biopsy, a radiograph, a CAT or PET scan and/or an MRI and the like.

In alternative embodiments, compounds of the invention can also comprise crystal forms, salts, solvates and hydrates. Thus, these compounds may crystallize with, for example, waters of hydration, or one, a number of, or any fraction thereof of molecules of the mother liquor solvent. The solvates and hydrates of such compounds are included within the scope of this disclosure.

In alternative embodiments, compounds of the invention (e.g., compounds of Formula I), comprise asymmetric carbon atoms. For example, compounds of Formula I can have the stereochemistry denoted in Formula I':

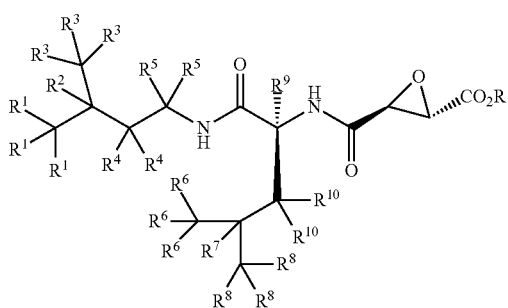

wherein in alternative embodiment: R is —H or alkyl; each of $R^1$, $R^2$, $R^3$, $R^4$, $R^5$, $R^6$, $R^7$, $R^8$, $R^9$, and $R^{10}$ is independently selected from the group consisting of —H, -D, —F, —OH, —CH$_3$, or a pharmaceutically acceptable salt or solvate thereof; with the proviso that at least one of $R^1$, $R^2$, $R^3$, $R^4$, $R^5$, $R^6$, $R^7$, $R^8$, $R^9$, and $R^{10}$ is not —H.

In alternative embodiments, compounds of the invention exist as (comprise) individual respective stereoisomers that are substantially free from another possible stereoisomer. In alternative embodiments, the term "substantially free of other stereoisomers" as used herein means less than about 15%, 20%, 25%, 30%, 35%, 40%, 50% or 55% of other stereoisomers, or less than about 10% of other stereoisomers, or less than about 5% of other stereoisomers, or less than about 2% of other stereoisomers, or less than about 1% or less of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

In alternative embodiments, compounds of the invention comprise or are formulated as pharmaceutically acceptable salts. Pharmaceutically acceptable salts of the compounds disclosed herein include suitable acid addition or base salts thereof. In alternative embodiments, compounds of the invention are formulated as described in Berge et al, *J Pharm Sci*, 66, 1-19 (1977).

In alternative embodiments, compounds of the invention formulated as salts that are formed, for example, with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid. Compounds of the invention also encompass salts which are not pharmaceutically acceptable, for example, a salt may still be valuable as an intermediate in a synthetic or analytical process or protocol.

In alternative embodiments, compounds of the invention comprise any acceptable salt for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Pharmaceutical compositions as disclosed herein can be prepared in accordance with methods well known and routinely practiced in the art. See, e.g., Remington: *The Science and Practice of Pharmacy*, Mack Publishing Co., 20th ed., 2000; and *Sustained and Controlled Release Drug Delivery Systems*, J. R. Robinson, ed., Marcel Dekker, Inc., New York, 1978.

In some embodiments, the compounds of the invention are provided in the form of pharmaceutically acceptable salts comprising an amine that is basic in nature and can react with an inorganic or organic acid to form a pharmaceutically acceptable acid addition salt; e.g., such salts comprise inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids; or optionally such pharmaceutically acceptable salts comprise sulfate, pyrosulfate, bisulfate, sulfite, bisulfate, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts.

In alternative embodiments, compounds of the invention, including pharmaceutical compositions and formulations of the invention, and compounds used to practice the methods of this invention, comprise compositions manufactured under "Good manufacturing practice" or GMP, or "current good manufacturing practices" (cGMP), conditions.

In alternative embodiments, formulations and pharmaceutical compositions of the invention comprise a therapeutically effective dose or efficacious dose of the active ingredient, e.g., one or more compounds of this invention, e.g., comprising a derivatized form, e.g., a deuterated form, e.g., which can be a metabolically blocked derivative, of AB-007 (loxistatin, E64d) and/or loxistatin acid (E64c), or a stereoisomer, salt, hydrate and/or solvate thereof, which in alternative embodiments is mixed with a pharmaceutically acceptable solvent, carrier or excipient. In alternative embodiments, formulations and pharmaceutical compositions of the invention comprise a therapeutically effective dose or efficacious dose of an active ingredient (e.g., an inhibitor of a cysteine protease, or a cathepsin, a caspase or a calpain, or a cathepsin L or a cathepsin B, or a cathepsin F, H, K, L1, L2, O, S, W, X or Z) for the amelioration, prevention or treatment of Alzheimer's disease (AD).

Conjugates of Compositions of the Invention

In alternative embodiments a composition of this invention, or a composition used to practice the methods of this invention (e.g., an inhibitor of a cysteine protease, or a cathepsin, a caspase or a calpain, or a cathepsin L or a cathepsin B, or a cathepsin F, H, K, L1, L2, O, S, W, X or Z), is linked to (e.g., conjugated or otherwise joined to) a chemical delivery system (CDS); e.g., a CDS such that the ratio of brain to periphery drug (a composition of this invention) levels can be increased. This embodiment can offer significant advantages in the treatments because the drug (e.g., a composition of this invention) because of the CDS linkage is concentrated in the brain, thereby reducing the dose and toxicity. For example, CDS prodrugs of the invention (e.g., comprising a composition of this invention) can be made using blood-brain barrier (BBB) penetrating moieties as described in U.S. Patent Application No. 20080227806.

In alternative embodiments, a composition of this invention, or a composition used to practice the methods of this invention (e.g., an inhibitor of a cysteine protease, or a cathepsin, a caspase or a calpain, or a cathepsin L or a cathepsin B, or a cathepsin F, H, K, L1, L2, O, S, W, X or Z), is linked to a CDS prodrug which exploits the bidirectional properties of the blood-brain barrier to lock-in the active compound (e.g., a composition of this invention) in the brain and allow sustained release of active compound, e.g., a cysteine protease inhibitor composition of this invention. In alternative embodiments, CDS moieties that can be linked to a composition of this invention, or a composition used to practice the methods of this invention (e.g., an inhibitor of a cysteine protease, or a cathepsin, a caspase or a calpain, or a cathepsin L or a cathepsin B, or a cathepsin F, H, K, L1, L2, O, S, W, X or Z), comprise pyridinium and pyridinium derivatives (e.g., 3-methyl-1-propylpyridinium, 1-butyl-3-methylpyridinium, and 1-butyl-4-methylpyridinium), 1,4-dihydrotrigonelline esters and/or amides, including dihydroquinoline- and dihydroisoquinoline-based target or moieties for brain-specific chemical delivery. In alternative embodiments a 1,4-dihydrotrigonelline esters or amides are used; they are hydrophobic and allow the CDS prodrug (comprising a composition of this invention) to readily cross the blood-brain barrier. A hydrophobic 1,4-dihydrotrigonelline can be converted in vivo to a hydrophilic quaternary form. This conversion takes place throughout the body via oxidation but without generating active or reactive radical intermediates. In the periphery the charged quaternary form is rapidly eliminated from the body but in the brain the charged form (e.g., of a composition of this invention) is locked behind the blood-brain barrier. This results in the brain being the only site containing the CDS prodrug and drug (e.g., a composition of this invention) after a relatively short period of time. There, the CDS prodrug continues to be metabolized and release the cysteine protease inhibitor composition of this invention. As a result, there is a sustained release of the drug composition in the brain. Thus, the CDS prodrug not only delivers the cysteine protease inhibitor moiety composition to the brain, it also provides preferential delivery there, thus targeting the brain.

Compositions of this invention, or a composition used to practice the methods of this invention (e.g., an inhibitor of a cysteine protease, or a cathepsin, a caspase or a calpain, or a cathepsin L or a cathepsin B, or a cathepsin F, H, K, L1, L2, O, S, W, X or Z), also can be linked or conjugated to a polypeptide, peptide or liposome to target the composition to the brain vasculature or otherwise expedite penetration of the BBB. For example, in one embodiment, a composition of this invention is linked or conjugated to a short peptide motif to create a penetration composition for specific transport across a biological barrier sealed by a tight junction, e.g., the BBB, e.g., as described in U.S. pat. App. Pub. no. 20060251713.

Formulations and Pharmaceutical Compositions

In alternative embodiments a composition of this invention (which include a derivatized form, e.g., a deuterated form, e.g., which can be a metabolically blocked derivative, of AB-007 (loxistatin, E64d) and/or loxistatin acid (E64c), or a stereoisomer, salt, hydrate and/or solvate thereof), or a composition used to practice the methods of this invention (e.g., an inhibitor of a cysteine protease, or a cathepsin, a caspase or a calpain, or a cathepsin L or a cathepsin B, or a cathepsin F, H, K, L1, L2, O, S, W, X or Z), is formulated for administration by any or a variety of means including orally, parenterally, by inhalation spray, nasally, topically, intrathecally, intrathecally, intracerebrally, epidurally, intracranially or rectally. Formulations of the invention can comprise pharmaceutically acceptable carriers, adjuvants and vehicles. In alternative embodiments, composition of this invention, or a composition used to practice the methods of this invention, are formulated for parenteral administration, including administration intrathecally, intracerebrally or epidurally (into a intrathecal, intracerebral, epidural space), subcutaneously, intravenously, intramuscularly and/or intraarterially; e.g., by injection routes but also including a variety of infusion techniques. Intraarterial, intrathecal, intracranial, epidural, intravenous and other injections as used in some embodiments can include administration through catheters or pumps, e.g., an intrathecal pump, or an implantable medical device (which can be an intrathecal pump or catheter).

In alternative embodiments a compound of the invention, or a composition used to practice the methods of this invention, can be formulated in accordance with a routine procedure(s) adapted for a desired administration route. Accordingly, in alternative embodiments compounds used to practice the invention are formulated or manufactured as lyophilates, powders, lozenges, liposomes, suspensions, solutions or emulsions in oily or aqueous vehicles, and can contain formulatory agents such as suspending, stabilizing and/or dispersing agents.

In alternative embodiments a compound of the invention, or a composition used to practice the methods of this invention, can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient (e.g., a composition of the invention) can be in powder form for constitution with a suitable vehicle, e.g., sterile pyrogen-free water, before use. Suitable alternative and exemplary formulations for each of these methods of administration can be found, for example, in Remington: *The Science and Practice of Pharmacy*, A. Gennaro, ed., 20th edition, Lippincott, Williams & Wilkins, Philadelphia, Pa.

In alternative embodiments a compound of the invention, or a composition used to practice the methods of this invention, can be formulations for parenteral administration comprising any common excipient, e.g., sterile water or saline, a polyalkylene glycol such as a polyethylene glycol, an oil of synthetic or vegetable origin, a hydrogenated naphthalene and the like. In alternative embodiments, a compound used to practice the invention can be a biocompatible, biodegradable lactide polymer, a lactide/glycolide copolymer, or polyoxyethylene-polyoxypropylene copolymers can be useful excipients to control the release of active compounds.

In alternative embodiments, a composition of the invention, or a composition used to practice the methods of this invention, is administered using parenteral delivery systems such as ethylene-vinyl acetate copolymer particles, osmotic pumps, implantable infusion systems, intrathecal catheters, pumps and implants, and/or use of liposomes. Formulations for parenteral administration can also include glycocholate for buccal administration, methoxysalicylate for rectal administration, or citric acid for vaginal administration. Formulations for inhalation administration can contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally.

In alternative embodiments, formulations of the invention, or a composition used to practice the methods of this invention, are administered intranasally. When given by this route, examples of appropriate dosage forms are a nasal spray or dry powder, as is known to those skilled in the art. For example, a nasal formulation can comprise a conventional surfactant, generally a non-ionic surfactant. When a surfactant is employed in a nasal formulation, the amount present will vary depending on the particular surfactant chosen, the particular mode of administration (e.g. drop or spray) and the effect desired.

In alternative embodiments, a pharmaceutical composition of the invention, or a composition used to practice the methods of this invention, is in the form of a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In alternative embodiments, sterile fixed oils are conventionally be employed as a solvent or suspending medium. For this purpose any bland fixed oil may be employed including synthetic mono- or diglycerides. In alternative embodiments, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule (ampoule) or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

In alternative embodiments, formulations of the invention, or a composition used to practice the methods of this invention, further comprise aqueous and non-aqueous sterile injection solutions that can contain (comprise) antioxidants, buffers, bacteriostats, bactericidal antibiotics and solutes that render the formulation isotonic with the bodily fluids of the intended recipient; and/or aqueous and non-aqueous sterile suspensions, which can include suspending agents and thickening agents.

In alternative embodiments, compounds of the invention, or a composition used to practice the methods of this invention, are formulated for topical administration, e.g., in the form of a liquid, lotion, cream or gel. Topical administration can be accomplished by application directly on the treatment area. For example, such application can be accomplished by rubbing the formulation (such as a lotion or gel) onto the skin of the treatment area, or by a spray application of a liquid formulation onto the application or treatment area.

In alternative embodiments, formulations of the invention, or a composition used to practice the methods of this invention, comprise a bioimplant or a bioimplant material, and also can be coated with a compound of the invention or another compounds so as to improve interaction between cells and the implant.

In alternative embodiments, formulations of the invention, or a composition used to practice the methods of this invention, comprise minor amounts of wetting or emulsifying agents, or pH buffering agents.

In alternative embodiments, formulations of the invention, or a composition used to practice the methods of this invention, are formulated as a suppository, with traditional binders and carriers such as triglycerides.

In alternative embodiments, formulations of the invention, or a composition used to practice the methods of this invention, comprise oral formulations such as tablets, pills, troches, lozenges (see, e.g., as described in U.S. Pat. No. 5,780,055), aqueous or oil suspensions, dispersible powders or granules, emulsions, hard or soft capsules or geltabs, gels, jellies, syrups and/or elixirs. Compositions intended for oral use may be prepared according to any method known to the art for the manufacture of pharmaceutical compositions and such compositions may contain one or more agents including sweetening agents, taste-masking agents, flavoring agents, coloring agents and preserving agents, in order to provide a palatable preparation. Oral formulations can include standard carriers such as pharmaceutical grades of mannitol, lactose, starch, magnesium stearate, polyvinyl pyrrolidone, sodium saccharine, cellulose, magnesium carbonate, etc. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In alternative embodiments, formulations for oral use are hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

In alternative embodiments, formulations of the invention, or a composition used to practice the methods of this invention, comprise aqueous suspensions comprising the active material (e.g., a compound of this invention) in admixture with excipients suitable for the manufacture of aqueous suspensions. Exemplary excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

In alternative embodiments, formulations of the invention, or a composition used to practice the methods of this invention, comprise oil suspensions that can be formulated by suspending the active ingredient (e.g., a compound of this invention) in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

In alternative embodiments, pharmaceutical formulations comprising the compounds of the invention, or a composition used to practice the methods of this invention, include an agent which controls release of the compound, thereby providing a timed or sustained release compound.

Carriers

In alternative embodiments, pharmaceutically acceptable carriers for manufacturing or formulating compounds of this invention, or a composition used to practice the methods of this invention, comprise aqueous or non-aqueous solutions, suspensions, emulsions and solids. Examples of non-aqueous solvents suitable for use as disclosed herein include, but are not limited to, propylene glycol, polyethylene glycol, vegetable oils such as olive oil, and injectable organic esters such as ethyl oleate. In alternative embodiments, aqueous carriers can comprise water, ethanol, alcoholic/aqueous solutions, glycerol, emulsions and/or suspensions, including saline and buffered media. Oral carriers can be elixirs, syrups, capsules, tablets and the like.

In alternative embodiments, liquid carriers are used to manufacture or formulate compounds of this invention, or a composition used to practice the methods of this invention, including carriers for preparing solutions, suspensions, emulsions, syrups, elixirs and pressurized compounds. The active ingredient (e.g., a composition of this invention) can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmoregulators.

In alternative embodiments, liquid carriers used to manufacture or formulate compounds of this invention comprise water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

In alternative embodiments, solid carriers are used to manufacture or formulate compounds of this invention, or a composition used to practice the methods of this invention, including solid carriers comprising substances such as lactose, starch, glucose, methylcellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, parenteral carriers are used to manufacture or formulate compounds of this invention, or a composition used to practice the methods of this invention, including parenteral carriers suitable for use as disclosed herein include, but are not limited to, sodium chloride solution, Ringer's dextrose, dextrose and sodium chloride, lactated Ringer's and fixed oils. Intravenous carriers can comprise fluid and nutrient replenishers, electrolyte replenishers such as those based on Ringer's dextrose and the like. Preservatives and other additives can also comprise, for example, antimicrobials, antioxidants, chelating agents, inert gases and the like.

In alternative embodiments, carriers used to manufacture or formulate compounds of this invention, or a composition used to practice the methods of this invention, can be mixed as needed with disintegrants, diluents, granulating agents, lubricants, binders and the like using conventional techniques known in the art. The carriers can also be sterilized using methods that do not deleteriously react with the compounds, as is generally known in the art.

The invention also provides articles of manufacture and kits containing (comprising) compounds of this invention, or a composition used to practice the methods of this invention, including pharmaceutical compositions and formulations. By way of example only a kit or article of manufacture can include a container (such as a bottle) with a desired amount of a compound (or pharmaceutical composition of a compound) described herein. Such a kit or article of manufacture can further include instructions for using the compound (or pharmaceutical composition of a compound) described herein. The instructions can be attached to the container, or can be included in a package (such as a box or a plastic or foil bag) holding the container.

The compounds of the invention, or a composition used to practice the methods of this invention, can be delivered to the body or targeted to a specific tissue or organ (e.g., a muscle or a brain) by any method or protocol, e.g., including ex vivo "loading of cells" with a composition of the invention; where the "loaded cell" is the administered intramuscularly, or intrathecally, intracerebrally, or epidurally into the central nervous system (CNS), e.g., as described in U.S. Pat. App. Pub. No. 20050048002.

In alternative embodiments, compounds of the invention, or a composition used to practice the methods of this invention, are first lyophilized and then suspended in a hydrophobic medium, e.g., comprising aliphatic, cyclic or aromatic molecules, e.g., as described in U.S. Pat. App. Pub. No. 20080159984.

Methods of Use

In alternative embodiments, a composition of this invention, which includes a derivatized form, e.g., a deuterated form, e.g., which can be a metabolically blocked derivative, of AB-007 (loxistatin, E64d) and/or loxistatin acid (E64c), or a stereoisomer, salt, hydrate or solvate thereof, or a composition used to practice the methods of this invention, is used as a cysteine protease inhibitor. In alternative embodiments compositions of the invention, or a composition used to practice the methods of this invention, are used to ameliorate (including treat, slow, reverse or prevent) a disease or condition which can be ameliorated by partial or complete inhibition of a cysteine protease, e.g., Alzheimer's disease (AD) or vascular dementia (VD), or Cognitive Dysfunction Syndrome (CDS) in a non-human animal.

While the invention is not limited by any particular mechanism of action, because cysteine proteases, including cathepsins (e.g., cathepsin B, or a cathepsin F, H, K, L1, L2, O, S, W, X or Z), caspases and calpains, are involved in a dementia or pre-dementia and/or a neurological pathology, and as these enzymes can be important in the development of cognitive loss or a dementia or pre-dementia, including cognitive loss or a dementia or pre-dementia due to AD or vascular dementia (VD), in alternative embodiments the compositions of the invention are used to ameliorate dementia or pre-dementia, neurological pathology, Alzheimer's disease (AD), Cognitive Dysfunction Syndrome (CDS) in a non-human animal, and/or vascular dementia (VD). The invention provides compositions (e.g., pharmaceutical compositions or formulations) and methods for preventing, slowing the progression of, reversing or ameliorating a cognitive loss, a dementia or pre-dementia, a neurological pathology, AD, VD and/or Cognitive Dysfunction Syndrome (CDS) in a non-human animal, and/or any disease of condition that can be ameliorated by complete or partial inhibition of a cysteine protease such as a cathepsin (e.g., a cathepsin B, or a cathepsin F, H, K, L1, L2, O, S, W, X or Z), a caspase and/or a calpain.

While the invention is not limited by any particular mechanism of action, in alternative embodiments, a composition of this invention is used to ameliorate a neurological disease, a dementia or pre-dementia and/or AD, by slowing the accumulation of, reversing or preventing β-amyloid (Aβ) and plaque formation, abnormal phosphorylation and/or aggregation of the microtubule-associated protein tau, and/or massive neuronal loss. In alternative embodiments, a composition of this invention is used to ameliorate hereditary forms of AD (e.g., familial AD, or FAD); and while the invention is not limited by any particular mechanism of action, mutations identified in hereditary forms of AD as well as abundant animal models and in vitro data strongly implicate Aβ and the polypeptide from which it is derived, the amyloid precursor protein (APP), as the principal factor driving the development of AD.

In alternative embodiments, the present application provides a method for inhibiting or slowing the activity of a cysteine protease enzyme, e.g., a cathepsin (e.g., a cathepsin B, or a cathepsin F, H, K, L1, L2, O, S, W, X or Z), a caspase and/or a calpain, comprising contacting cells containing the cysteine protease enzyme (e.g., the cathepsin B, etc.) with an effective amount of a compound of this invention, e.g. a compound of Formula I, which can be a metabolically blocked analog (e.g., deuterated analog) of AB-007 (loxistatin, E64d) and/or loxistatin acid (E64c), or a stereoisomer, salt, hydrate or solvate of a composition of this invention, e.g. a compound encompassed by Formula I.

In one aspect the present application provides a method for preventing, slowing the progression of, reversing, or treating Alzheimer's disease (AD), VD or Cognitive Dysfunction Syndrome (CDS) in a non-human animal, comprising administering to a patient in need thereof an effective amount a compound of this invention, e.g. a compound of Formula I, which can be a metabolically blocked analog of AB-007 (loxistatin, E64d) and/or loxistatin acid (E64c), or a stereoisomer, salt, hydrate or solvate of a composition of this invention, e.g. a compound encompassed by Formula I.

The present application also provides a method of reducing or preventing the effects of β-amyloid in an individual or subject (e.g., a patient or a non-human animal) comprising administering to said individual or subject (e.g., patient or a non-human animal) an effective amount of a compound of this invention, e.g. a compound of Formula I, which can be a metabolically blocked analog of AB-007 (loxistatin, E64d) and/or loxistatin acid (E64c), or a stereoisomer, salt, hydrate or solvate of a composition of this invention, e.g. a compound encompassed by Formula I, such that the effects of β-amyloid are reduced or prevented.

The present application also provides a method of preventing, slowing or reversing neuronal cell apoptosis or death in an individual or subject (e.g., a patient or a non-human animal) comprising administering to said individual or subject (e.g., patient or a non-human animal) an effective amount of a compound of this invention, e.g. a compound of Formula I, which can be a metabolically blocked analog of AB-007 (loxistatin, E64d) and/or loxistatin acid (E64c), or a stereoisomer, salt, hydrate or solvate of a composition of this invention, e.g. a compound encompassed by Formula I, such that neuronal cell death is prevented.

Dosages

In alternative embodiments, compositions of the invention, or compositions used to practice the methods of the invention, are formulated and administered in a variety of different dosages and treatment regimens, depending on the disease or condition to be ameliorated, the condition of the individual to be treated, the goal of the treatment, and the like, as to be routinely determined by the clinician, see e.g., the latest edition of Remington: *The Science and Practice of Pharmacy*, Mack Publishing Co., supra.

In alternative embodiments, the effective amount of a compound of this invention, e.g. a compound of Formula I, which can be a metabolically blocked analog of AB-007 (loxistatin, E64d) and/or loxistatin acid (E64c), or a stereoisomer, salt, hydrate or solvate of this invention, e.g. a compound encompassed by Formula I, or a composition used to practice the methods of the invention, is between about 0.1 mg and about 20.0 mg per kg of body weight of the individual or subject (e.g., patient). In another variation, the effective amount is between about 0.1 mg and about 10.0 mg per kg of body weight of the individual or subject (e.g., patient) or between about 0.1 mg and about 5.0 mg per kg of body weight of the patient. Alternately, the effective amount is between about 0.2 mg and about 2 mg per kg of body weight of the individual or subject (e.g., patient).

In a further variation of any of the disclosed aspects or as an alternative embodiment, the administration of a therapeutically effective amount of a compound of this invention, e.g. a compound of Formula I, which can be a metabolically blocked analog of AB-007 (loxistatin, E64d) and/or loxistatin acid (E64c), or a stereoisomer, salt, hydrate or solvate of a composition of this invention, e.g. a compound encompassed by Formula I, elicits an "improved" clinical effect during the treatment in said individual, subject or patient per dosage unit thereof as compared to the "parent" AB-007 (loxistatin, E64d) and/or loxistatin acid (E64c); e.g., by administering a composition of this invention instead of AB-007 (loxistatin, E64d) and/or loxistatin acid (E64c), a lower dosage can be used.

While the invention is not limited by any particular mechanism of action, in one embodiment, it is predicated in part on the discovery that AB-007, at dosages significantly lower than that suggested in the art, are effective in treating a loss in cognitive abilities, a dementia or pre-dementia (e.g. as in AD and VD) and Cognitive Dysfunction Syndrome (CDS) in a non-human animal AB-007 (loxistatin, E64d) has been shown to be a neuroprotectant and thus may not only reduce the likely cause of AD, abnormal Aβ accumulation, but also protect against Aβ toxicity and thus be effective in treating a loss in cognitive abilities, a dementia or pre-dementia (e.g. as in AD and VD) and Cognitive Dysfunction Syndrome (CDS) in a non-human animal.

Cathepsin B inhibitors administered intracerebroventricularly (icy) (0.15 mg/kg/day for 30 days) to guinea pigs, which express Aβ identical to human and have APP containing the human wt (wild type) β-secretase site sequence, have been found to reduce brain Aβ and CTFβ (C-terminal β-secretase fragment (CTFβ) derived from APP) by up to 70%. Moreover, this treatment also reduces the Aβ and CTFβ in synaptosome fractions, which are a measure of brain regulated secretion.

It has been reported that deleting the cathepsin B gene in transgenic mice expressing wt hAPP (the allele present in the majority of humans) resulted in 67% less brain Aβ40 and Aβ42 and 41% less CTF3 than in corresponding transgenic controls expressing cathepsin B.

SiRNA silencing cathepsin B reduces secretion of Aβ in primary rat hippocampal cells, which express APP containing the human wild-type β-secretase site. Moreover, it has been shown that a cathepsin B inhibitor reduces regulated secretion of Aβ in the hippocampal cells.

Cathepsin B does not cleave the Swedish (Swe) mutant β-secretase site in APP, and neither inhibiting cathepsin B nor deleting the cathepsin B gene reduces Aβ or CTFβ in animals expressing that site. Most AD patients express APP having the wt β-secretase site whereas only a small number express the Swe β-secretase site.

In contrast, cathepsin B inhibitors are efficacious at lowering Aβ in models expressing the wt APP secretase cleavage site; thus, it is anticipated that they also do so in most Alzheimer's patients (most humans have the wt APP secretase cleavage site). Thus, the compositions and methods of this invention are effective in most Alzheimer's patients.

Oral AB-007 (loxistatin, E64d) is rapidly and completely converted in the gut to E64c (loxistatin acid) as shown above. In humans, the only metabolites are E64c and two hydroxylated forms of E64c. No drug accumulation occurs in humans. The serum half-life (biz) in humans for E64c and the hydroxylated E64c forms is about 1.3 and 2.5 hours, respectively. The Area Under the Curve (AUC) in humans for E64c and the hydroxylated E64c forms is about 4.6 and 5.08 mg/hr/mL, respectively. The total urinary excretion rate in humans is about 30%.

Radioactive AB-007 (loxistatin, E64d) studies in animals have shown that the primary absorption site is the small intestine, where about 60% of an oral dose is absorbed. The maximum tissue concentration occurs 0.5 hours after administration and, excluding the gastrointestinal track, the liver and kidneys have the highest concentrations at about 25 and 12 times that of the plasma concentration, respectively. All other organs, including the brain, have a concentration corresponding to the plasma concentration or concentrations lower than plasma.

The LD50 for oral AB-007 (loxistatin, E64d) is over 10,000 mg/kg and 5,000 mg/kg for rats and dogs, respectively. The subacute no-effect dose for oral AB-007 is under 80 mg/kg/day and 40 mg/kg/day in rats and dogs, respectively. Chronic toxicity data indicate that the liver and kidney are the target organs for toxicity and that no-effect dose level is below 2 mg/kg/day and 5 mg/kg/day in rats and dogs, respectively.

Rats appear to be a particularly sensitive species to AB-007 (loxistatin, E64d) toxicity as the hepatic injury seen in rats does not occur in other species. High oral doses of AB-007 (500 mg/kg and 1 g/kg) depress the central nervous system, causing sedation and mild inhibition of pentetrazol-induced seizure, but have no effect on the cardiovascular system. The maximal intravenous or oral AB-007 doses do not influence vision or hearing in rats.

In healthy human volunteers, single or continuous 1 week oral administration of AB-007 (loxistatin, E64d) at about 5 mg/kg/day causes no change in pulse, blood pressure, body temperature, grip force, electrocardiogram, or physician observations. Moreover, there are no changes in hematological tests, including leukocyte count, erythrocyte count, hemoglobin, hematocrit, platelet count, reticulocyte count, differential leukocyte count, blood chemistry, including GOT, GPT, LDH, A1-P, LAP, γ-GTP, CPK, BUN, creatinine, uric acid, total cholesterol, triglycerides, serum total proteins, protein fraction, Cl, Na, K, Ca, P, and urinalyses including pH, proteins, sugar, urobilinogen, occult blood and sediment.

Oral radioactive AB-007 (loxistatin, E64d) data in animals show that the resulting brain drug dose, although low, is nonetheless ample for reducing brain Aβ via inhibition of cathepsin B. A 5 mg/kg oral AB-007 dose results in E64c brain concentrations in the rat and hamster that are 100 fold and 300 fold, respectively, greater than that needed to inhibit by 50% cathepsin B cleavage of the wt β-secretase cleavage site ($IC_{50}$).

As detailed in the Examples below, a daily 10 mg/kg guinea pig oral dose of AB-007 (loxistatin, E64d) has been shown to reduce brain $A\beta_{40}$ and $A\beta_{42}$ by 42% relative to vehicle treated controls. A 10 mg/kg guinea pig oral dose allometrically scales to a 2 mg/kg human oral dose, which is well below the 5 mg/kg dose of AB-007 previously administered to humans.

In alternative embodiments, the present invention provides dosage forms and formulations of AB-007 (loxistatin, E64d) and/or loxistatin acid (E64c), and compositions of this invention, and compositions used to practice this invention, comprising less than about 1, 2, 3, 4 or 5 mg per kg body weight of a subject or individual. In alternative embodiments, the present invention provides dosage forms and formulations of AB-007 (loxistatin, E64d) and/or loxistatin acid (E64c), compositions of this invention), and compositions of this invention, and compositions used to practice this invention, comprising more than about 5, 6, 7, 8, 9 or 10 or more mg per kg body weight of a subject or individual. In alternative embodiments, for an adult human subject with a body weight of around 75 kg, the daily dosage of about 0.1 mg/kg to about 10 mg/kg to be administered is from about 7.5 mg daily to about 750 mg daily.

In some embodiments, human subjects with similar body weights are treated by administered dosage of e.g., AB-007 (loxistatin, E64d), and/or loxistatin acid (E64c) and/or compositions of this invention, and/or compositions used to practice this invention, from about 0.1 mg/kg to about 2 mg/kg, or from about 7.5 mg to about 150 mg daily. In other embodiments, human subjects are administered a dosage of e.g., AB-007 (loxistatin, E64d) and/or loxistatin acid (E64c) and/or compositions of this invention, and/or compositions used to practice this invention, from about 0.1 mg/kg to about 0.5 mg/kg or from about 7.5 mg to about 38 mg AB-007.

For other human subject with different body weight or non human subject, the amount of drug, e.g., AB-007 (loxistatin, E64d) and/or loxistatin acid (E64c) and/or compositions of this invention or compositions used to practice this invention, to be administered can be readily calculated based on their exact body. In alternative embodiments, these exemplary dosage forms are administered to patients suffering from a cognitive loss, a dementia or pre-dementia, AD (including preclinical, pre-symptomatic forms), VD and/or Cognitive Dysfunction Syndrome (CDS) in a non-human animal. While the suitable drug (e.g., AB-007) dosages employed in the present invention can be described by the amount of drug (e.g., AB-007) per kg of body weight of the subject, the exact amount of a compound of this invention, or loxistatin acid or AB-007, or compositions used to practice this invention, to be administered can be readily (routinely) determined by the skilled artisan (clinician). In alternative embodiments, less (derivatized) compositions of the invention can be used in a dosage or formulation, because use of the (derivatized) compositions of the invention (versus the "parent" AB-007 (E64d) and/or loxistatin acid (E64c)) can result in increasing the effective concentration of a composition of the invention as a drug, and can also increase its half life in vivo.

In alternative embodiments, the invention provides kits comprising a solid dosage form of a compound of this invention, a composition used to practice this invention, or loxistatin acid or AB-007; and also can comprise an instruction for administering said dosage once daily for treatment of the intended disease or condition (or pre-condition), including e.g., a cognitive loss, a dementia or pre-dementia, AD, VD and/or Cognitive Dysfunction Syndrome (CDS) in a non-human animal, wherein said solid dosage form comprises between about 1 mg and about 400 mg of the drug, e.g., loxistatin acid or AB-007.

In alternative embodiments, the solid dosage forms of the invention (e.g., as a pill, tablet or lozenge), including those in the kits or pharmaceutical compositions of the invention, comprise between about 1 mg and about 250 mg of a compound of this invention, a composition used to practice this invention, or AB-007 (loxistatin, E64d) and/or loxistatin acid (E64c); or comprise between about 5 mg and about 150 mg of a compound of this invention, a composition used to practice this invention, or AB-007 (loxistatin, E64d) and/or loxistatin acid (E64c); or comprise between about 1 mg and about 75 mg of a compound of this invention, a composition used to practice this invention, or AB-007 (loxistatin, E64d) and/or loxistatin acid (E64c).

In alternative embodiments, the kits pharmaceutical compositions of the invention can comprise a solid dosage form (e.g., as a pill, tablet or lozenge) comprising about 100 mg, about 150 mg, about 200 mg, about 250 mg, about 300 mg, about 350 mg, or about 400 mg of a compound of this invention, a composition used to practice this invention, or AB-007 (loxistatin, E64d) and/or loxistatin acid (E64c). The solid dosage form (e.g., as a pill, tablet or lozenge) also can comprise about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg of a compound of this invention, a composition used to practice this invention, or AB-007 (loxistatin, E64d) and/or loxistatin acid (E64c). The solid dosage form (e.g., as a pill, tablet or lozenge) can comprise about 5 mg, about 10 mg, about 15 mg, about 20 mg, about 25 mg, about 30 mg, about 35 mg, about 40 mg, about 45 mg, or about 50 mg of a compound of this invention, a composition used to practice this invention, or AB-007 (loxistatin, E64d) and/or loxistatin acid (E64c).

The invention provides methods for treating a cognitive loss, a dementia or pre-dementia, AD, VD and/or Cognitive Dysfunction Syndrome (CDS) in a non-human animal, comprising administering to an individual, subject or patient in need thereof an effective amount of a compound of this invention, a composition used to practice this invention, or AB-007 (loxistatin, E64d) and/or loxistatin acid (E64c), wherein said effective amount (e.g., as a solid dosage, such as a pill, tablet or lozenge) is between about 0.1 mg and about 5.0 mg per kg of body weight of said individual, subject or patient.

In alternative embodiments, an effective amount of a compound of this invention, a composition used to practice this invention, or AB-007 (loxistatin, E64d) and/or loxistatin acid (E64c) (e.g., as a solid dosage, such as a pill, tablet or lozenge) is between about 0.1 mg and about 2.0 mg per kg of body weight of said individual, subject or patient; or is between about 0.1 mg and about 1.0 mg per kg of body weight; or is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, or about 1.0 mg of a compound of this invention, or AB-007 (loxistatin, E64d) and/or loxistatin acid (E64c) per kg of body weight; or an effective amount of a compound of this invention, a composition used to practice this invention, or AB-007 (loxistatin, E64d) and/or loxistatin acid (E64c) is about 0.1 mg, about 0.15 mg, about 0.2 mg, about 0.25 mg or about 0.3 mg per kg of body weight; or an effective amount of a compound of this invention, a composition used to practice this invention, or AB-007 (loxistatin, E64d) and/or loxistatin acid (E64c) is about 0.2 mg AB-007 per kg of body weight.

The invention provides methods for treating a cognitive loss, a dementia or pre-dementia, AD, VD and/or Cognitive Dysfunction Syndrome (CDS) in a non-human animal, comprising administering to an individual, subject or patient in need thereof an effective amount of a compound of this invention, a composition used to practice this invention, or AB-007 (loxistatin, E64d) and/or loxistatin acid (E64c), wherein said effective amount (e.g., as a solid dosage, such as a pill, tablet or lozenge) is between about 1 mg and about 400 mg; or is a solid dosage form comprising between about 1 mg and about 250 mg; or the solid dosage form comprises between about 5 mg and about 150; or the solid dosage form (e.g., as a pill, tablet or lozenge) comprises between about 1 mg and about 75; or the solid dosage form comprises about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg.

The invention provides methods for treating a cognitive loss, a dementia or pre-dementia, AD, VD and/or Cognitive Dysfunction Syndrome (CDS) in a non-human animal, comprising administering to an individual, subject or patient in need thereof a compound of this invention, a composition used to practice this invention, or AB-007 (loxistatin, E64d) and/or loxistatin acid (E64c) administered as a daily oral dosage form (e.g., as a solid dosage, such as a pill, tablet or lozenge).

In one embodiment the invention provides methods of slowing, reversing, reducing or preventing the effects of β-amyloid in an individual, subject or patient comprising administering to an individual, subject or patient in need thereof an effective amount of a compound of this invention, a composition used to practice this invention, or AB-007 (loxistatin, E64d) and/or loxistatin acid (E64c), wherein said effective amount (e.g., as a solid dosage, such as a pill, tablet or lozenge) is between about 0.1 mg and about 5.0 mg per kg of body weight of said patient; or is between about 0.1 mg and about 2.0 mg per kg of body weight; or is between about 0.1 mg and about 1 mg per kg of body weight; or is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, or about 1.0 mg per kg of body weight; or is about 0.1 mg, about 0.15 mg, about 0.2 mg, about 0.25 mg or about 0.3 mg per kg of body weight; or is about 0.2 mg per kg of body weight.

In one embodiment the invention provides methods of slowing, reversing, reducing or preventing the effects of β-amyloid, or β-amyloid accumulation, or β-amyloid plaque formation, in an individual, subject or patient comprising administering to said individual, subject or patient an effective amount of a compound of this invention, a composition used to practice this invention, or AB-007 (loxistatin, E64d) and/or loxistatin acid (E64c) such that the effects of β-amyloid are reduced or prevented, wherein said effective amount (e.g., as a solid dosage, such as a pill, tablet or lozenge) is between about 1 mg and about 400 mg; or is between about 1 mg and about 250 mg; or between about 5 mg and about 150 mg; or between about 1 mg and about 75 mg; or about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg. In one embodiment the compound of this invention, a composition used to practice this invention, or AB-007 (loxistatin, E64d) and/or loxistatin acid (E64c) is administered as a daily oral dosage (e.g., solid dosage, such as a pill, tablet or lozenge) form.

In one embodiment the invention provides methods of slowing, reversing, reducing or preventing neuronal cell death in an individual, subject or patient comprising administering to the individual, subject or patient in need thereof an effective amount of a compound of this invention, a composition used to practice this invention, or AB-007 (loxistatin, E64d) and/or loxistatin acid (E64c), wherein said effective amount is between about 0.1 mg and about 5.0 mg per kg of body weight; or is between about 0.1 mg and about 2.0 mg per kg of body weight; or is between about 0.1 mg and about 1 mg per ckg of body weight of said patient; or is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, or about 1.0 mg per kg of body weight; or is about 0.1 mg, about 0.15 mg, about 0.2 mg, about 0.25 mg or about 0.3 mg per kg of body weight; or is about 0.2 mg per kg of body weight.

In one embodiment the invention provides methods of slowing, reversing, reducing or preventing neuronal cell death in an individual, subject or patient comprising administering to said individual, subject or patient an effective amount of a compound of this invention, a composition used to practice this invention, or AB-007 (loxistatin, E64d) and/or loxistatin acid (E64c) such that neuronal cell death is slowed, reversed, reduced and/or prevented, wherein said effective amount is between about 1 mg and about 400 mg; or is (e.g., as a solid dosage form) between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg. In one embodiment, the compound of this invention, a composition used to practice this invention, or AB-007 (loxistatin, E64d) and/or loxistatin acid (E64c) is administered as a daily oral dosage (e.g., solid dosage, such as a pill, tablet or lozenge) form.

Diagnosis and Assessment of Dementia and AD

In alternative embodiments, any method, procedure or protocol, including those based on one or more psychological, cognitive, imaging, biomarker and/or genetic parameters and/or measurements, are used to predict, detect, monitor the progression of and/or monitor the effectiveness of a prophylactic or clinical treatment (e.g., using a composition or dosage formulation of this invention) for VD, AD and/or any other neuro-dementing disease. This monitoring and assessment allows the skilled artisan to determine if a modification of dosage and/or treatment regimen is needed or desired to maximize effectiveness of a composition of this invention for a particular individual or patient.

For example, in alternative embodiments the following diagnostics can be used alone or in combination: determinations for genetic risk factors or mutations (mainly for FAD cases, but also for sporadic AD diagnostics); neuroimaging methods; diagnostics based on biochemical/biological markers. For example, in humans a gene variant APOE3 is associated with a neutral risk of developing the disease, while the APOE4 variant is associated with a high risk. Thus, an individual having the APOE4 variant is a candidate individual to have administered a composition of this invention and/or a method of this invention.

Risk of developing Alzheimer's appears to be slightly higher if a first-degree relative such as a parent, sister or brother has the disease. Thus, in alternative embodiments, an individual having a first-degree relative with AD, VD, or a dementia or pre-dementia is a candidate individual to have administered a composition of this invention and/or a method of this invention.

Researchers have found that an increase of 5 micromoles of homocysteine per liter of blood increases the risk of AD by 40%. People with higher homocysteine levels in blood had nearly double the risk of disease AD and other dementias in relation to people with low blood homocysteine. Thus, in alternative embodiments, an individual having higher homocysteine levels in blood a candidate individual to have administered a composition of this invention and/or a method of this invention.

In alternative embodiments, criteria to clinically diagnose AD, VD, or a dementia or pre-dementia and/or to monitor (assess) the effectiveness of a composition of the invention or a dosage formulation of the invention comprises the DSM-IIIR criteria and the NINCDS-ADRDA criteria (National Institute of Neurological and Communicative Disorders and Stroke (NINCDS) and the Alzheimer's Disease and Related Disorders Association (ADRDA); see McKhann et al., Neurology 34:939-944, 1984). The criteria for diagnosis of AD under DSM-IIIR can include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgment, abstract thought, and other higher cortical functions, and changes in personality and behavior." (DSM-IIR, 1987).

In alternative embodiments, NINCDS-ADRDA criteria are used; the NINCDS-ADRDA sets forth three categories of AD, including "probable," "possible," and "definite" AD. Clinical diagnosis of "possible" AD may be made on the basis of a dementia or pre-dementia syndrome, in the absence of other neurologic, psychiatric or systemic disorders sufficient to cause dementia. Criteria for the clinical diagnosis of "probable" AD can include (a) dementia established by clinical examination and documented by a test such as the Mini-Mental test (Foldstein et al., J. Psych. Res. 12:189-198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia.

In alternative embodiments, criteria for definite diagnosis of AD include histopathologic evidence obtained from a biopsy, or after autopsy. Since confirmation of definite AD requires histological examination from a brain biopsy specimen (which is often difficult to obtain), it is rarely used for early diagnosis of AD.

In alternative embodiments, neuropathologic diagnosis of AD is used. Presence and numbers of plaques and tangles in the neurocortex (frontal, temporal, and parietal lobes), hippocampus and amygdala are analyzed (Khachaturian, Arch. Neurol. 42:1097-1105; Esiri, "Anatomical Criteria for the Biopsy diagnosis of Alzheimer's Disease," Alzheimer's Disease, Current Research in Early Diagnosis, Becker and Giacobini (eds.), pp. 239-252, 1990).

In alternative embodiments, quantitative electroencephalographic analysis (EEG) is used to diagnose AD. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159-167, 1990) for diagnosis of AD.

In alternative embodiments, quantifying the degree of neural atrophy is used. Such atrophy can be a consequence of AD. Examples of these methods include computed tomographic scanning (CT), and magnetic resonance imaging (MRI) (Leedom and Miller, "CT, MRI, and NMR Spectroscopy in Alzheimer's Disease," Alzheimer's Disease, Current Research in Early Diagnosis, Becker and Giacobini (eds.), pp. 297-313, 1990).

In alternative embodiments, decreased cerebral blood flow or metabolism in the posterior temporoparietal cerebral cortex is used to diagnose VD or AD. Decreased blood flow or metabolism by positron emission tomography (PET) is measured, e.g., see Parks and Becker, "Positron Emission Tomography and Neuropsychological Studies in Dementia," Alzheimer's Disease's, Current Research in Early Diagnosis, Becker and Giacobini (eds.), pp. 315-327, 1990. Single photon emission computed tomography (SPECT) also can be used, see e.g., Mena et al., "SPECT Studies in Alzheimer's Type Dementia Patients," Alzheimer's Disease, Current Research in Early Diagnosis, Becker and Giacobini (eds.), pp. 339-355, 1990). Xenon inhalation methods also can be used, see, e.g., Jagust et al., Neurology 38:909-912; Prohovnik et al., Neurology 38:931-937; and Waldemar et al., Senile Dementias: II International Symposium, pp. 399407, 1988.

In alternative embodiments, AD can be immunologically diagnosed, see e.g., Wolozin, "Immunochemical Approaches to the Diagnosis of Alzheimer's Disease," Alzheimer's Disease, Current Research in Early Diagnosis, Becker and Giacobini (eds.), pp. 217-235, 1990. Wolozin and coworkers (Wolozin et al., Science 232:648-650, 1986) produced a monoclonal antibody "Alz50," that reacts with a 68-kDa protein "A68," which is expressed in the plaques and neuron tangles of patients with Alzheimer's disease. Using the antibody Alz50 and Western blot analysis, A68 was detected in the cerebral spinal fluid (CSF) of some Alzheimer's patients and not in the CSF of normal elderly patients (Wolozin and Davies, Ann. Neurol. 22:521-526, 1987). In another embodiment, antibodies against beta-amyloid (e.g., as described in U.S. Pat. Appl. No. 20090028869) can be used to diagnose or monitor (assess) the effectiveness of a prophylactic or clinical treatment using a composition of this invention.

In alternative embodiments, neurochemical markers of AD are used, including neurochemical markers comprising reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137-156, 1990), reduced somatostatin (Tamming a et al., Neurology 37:161-165, 1987), a negative relation between serotonin and 5-hydroxyindoleacetic acid (Volicer et al., Arch Neurol. 42:127-129, 1985), greater probenecid-induced rise in homovanyllic acid (Gibson et al., Arch. Neurol. 42:489-492, 1985) and/or reduced neuron-specific enolase (Cutler et al., Arch. Neurol. 43:153-154, 1986).

In alternative embodiments, various types of dementia can be diagnosed and monitored, and the progression of the disease over an extended period of time assessed, using (i) a memory assessment, (ii) an extensive neuropyschological exam, (iii) an examination by a geriatric neurologist and/or (iv) MRI imaging of the brain. Disease progression can be documented by changes in these parameters over time. In some embodiments, changes in the parameters of at least one of these assessments can be used to assess the efficacy of a composition of this invention in an individual, patient or subject over time.

In alternative embodiments, a memory assessment is used, e.g., adult patients with complaint of short term memory and/or cognitive decline, whether self-referred or directed from a clinician on the suspicion of a possible or probable memory disorder or dementia, are evaluated (i) memory assessment (ii) an extensive neuropsychological exam, (iii) an examination by a geriatric neurologist and/or (iv) MRI imaging of the brain are performed. A neuropsychology assessment captures a broad inventory of cognitive function which aids in determining the array and severity of deficits. These include assessments of judgment, insight, behavior, orientation, executive Control, general intellectual functioning, visual-spatial function, memory and/or new learning ability. Depression, if present, is identified. A neurological evaluation can captures the history of cognitive alteration as well as the general medical history, and typically a complete neurological exam is performed. A neurological examination can also comprise laboratory studies to exclude reversible causes of dementia including Vitamin B12, Folate, Basic Metabolic Profile, CBC, TSH, ALT, AST, C-reactive protein, serum homocysteine, and RPR.

In alternative embodiments, compositions of the invention are used to treat "pre-dementia" patients, where the first symptoms are often mistaken as related to aging or stress. Detailed neuropsychological testing can reveal mild cognitive difficulties up to eight years before a person fulfills the clinical criteria for diagnosis of AD. These early symptoms can affect the most complex daily living activities. The most noticeable deficit is memory loss, which shows up as difficulty in remembering recently learned facts and inability to acquire new information. Subtle problems with the executive functions of attentiveness, planning, flexibility, and abstract thinking, or impairments in semantic memory (memory of meanings, and concept relationships), can also be symptomatic of the early stages of AD. Apathy can be observed at this stage, and remains the most persistent neuropsychiatric symptom throughout the course of the disease. The preclinical stage of the disease has also been termed mild cognitive impairment, but whether this term corresponds to a different diagnostic stage or identifies the first step of AD is a matter of dispute. In alternative embodiments, compositions of the invention are used to treat individuals with mild cognitive impairment and/or pre-dementia.

Animal Cognitive Dysfunction Syndrome (CDS)

In alternative embodiments, the invention provides pharmaceutical compositions comprising dosage forms and formulations of the invention for administration to human and non-human subjects, e.g., including e.g. domestic, farm, experimental and zoo animals, including e.g., dogs and cats. In alternative embodiments, compositions and methods of the invention are used to treat, prevent, slow the progress of or ameliorate a Cognitive Dysfunction Syndrome (CDS) in a non-human animal, e.g., dogs and cats. In one embodiment, CDS includes Canine Cognitive Dysfunction (CCD), which is sometimes referred to as "old dog syndrome", "brain aging", "doggie dementia" or "senility".

Animal CDS can have a pathology mimicking Alzheimer's disease (AD) pathology. Dogs with CDS accumulate the toxic beta amyloid protein seen in the brains of patients with AD. The deposits in dogs occur in similar brain regions as humans, and the extent of deposition correlates with the level of cognitive impairment, as in patients with AD. In dogs, disturbances in four main behavioral categories emerge: disorientation seen in daily walks or at home; impaired interaction with owners; sleep/wake cycle disturbances with barking and pacing at nights and loss of continence. These areas are often impaired in AD patients, although of course, the manifestations are different.

Much like in people, the risk for cognitive dysfunction in dogs and cats increases with age. In dogs as in people, there is a progression from mild cognitive impairment to frank symptoms of dementia. Dogs nine years and older and cats over 12 are at risk for CDS. Over a quarter of 11 to 12 year old dogs (28 percent) and nearly three quarters (68 percent) of 15 to 16 year old dogs are impaired. Female gender places both dogs and women at higher risk for cognitive impairment. Spayed female dogs are more at risk for CDS just as women who undergo early menopause or hysterectomies have a higher risk for AD. Accordingly, compositions and methods of the invention are designed for and formulated for administration to dogs starting at between about ages 9 to 11.

The evaluation for animal Cognitive Dysfunction Syndrome (CDS), as for AD, involves screening for reversible causes of cognitive impairment such as infections, endocrine problems and other ailments. Brain MRIs in CDS reveal brain shrinkage or atrophy and an increase in the size of the brain's ventricular cavities, parallel to findings in people with AD. Brain MRIs performed for behavioral changes may reveal large or small strokes. Other common conditions that exacerbate CDS and predispose to strokes include untreated hypertension, high cholesterol levels and poorly controlled diabetes.

In alternative embodiments, the invention provides formulations and dosages for slowing, reversing, reducing or preventing animal Cognitive Dysfunction Syndrome (CDS).

Formulations and dosages for administering an effective amount of a compound comprising an inhibitor of a cysteine protease, or a cathepsin, a caspase or a calpain, or a cathepsin L or a cathepsin B, or a cathepsin F, H, K, L1, L2, O, S, W, X or Z, which includes but is not limited to compositions of this invention, for animal Cognitive Dysfunction Syndrome (CDS) are discussed above.

In alternative embodiments, the invention provides formulations and dosages comprising a composition of the invention, or a dosage formulation of the invention, in combination with selegiline (e.g., selegiline hydrochloride) or deprenyl, or ANIPRYL™, which is a pill composed of 2 to 17% selegiline hydrochloride, stearic acid, colloidal silicon dioxide, talc (non-asbestiform), microcrystalline cellulose crospovidone and polyethylene glycol, and is one of the top medications for canine dementia. Selegiline (or deprenyl) also is used to treat Alzheimer's and Parkinson's in humans. ANIPRYL™ works by increasing the level of an essential neurotransmitter called dopamine. ANIPRYL™ has shown to reverse some of the changes associated with canine dementia and it improves the behavior in about 75% of affected dogs in one month. In some cases, it may take up to 60 days.

Combination Formulations

In alternative embodiments, the invention provides pharmaceutical compositions comprising compositions, dosage forms and formulations of the invention further comprising at least one other (e.g., at least one additional, different) pharmaceutical composition, dosage form or formulation used to treat or ameliorate, or treat the symptoms of, or be palliative for: a cognitive dysfunction or a loss of cognition, a dementia or a pre-dementia, Alzheimer's disease (AD), Vascular Dementia (VD), and/or a Cognitive Dysfunction Syndrome (CDS), in humans or in a non-human animal. The at least one additional, different pharmaceutical composition, dosage form or formulation can be any known treatment or palliative for a dementia, AD, VD or CDS.

For example, in alternative embodiments, the at least one other (e.g., at least one additional, different) pharmaceutical composition, dosage form or formulation comprises a selegiline (e.g., selegiline hydrochloride) or deprenyl, or ANIPRYL™

In alternative embodiments, the at least one other (e.g., at least one additional, different) pharmaceutical composition, dosage form or formulation comprises an acetylcholinesterase inhibitor (AChEI) or anti-cholinesterase, e.g., a donepezil (ARICEPT™); a carbamate; edrophonium or comparable reversible acetylcholinesterase inhibitor (e.g., TENSILON™, ENLON™, REVERSOL™); a neostigmine (e.g., PROSTIGMIN™, VAGOSTIGMIN™); a galantamine (e.g., NIVALIN™, RAZADYNE™ RAZADYNE ER™, REMINYL™); a rivastigmine (e.g., EXELON), and any equivalent or combination thereof.

In alternative embodiments, the at least one other (e.g., at least one additional, different) pharmaceutical composition, dosage form or formulation comprises a memantine or comparable blocker of NMDA glutamate receptors (including e.g., AXURA™ AKATINOL™, NAMENDA™, EBIXA™, ABIXA™, MEMOX™), any equivalent or combination thereof.

In alternative embodiments, the at least one other (e.g., at least one additional, different) pharmaceutical composition, dosage form or formulation comprises a nutritional supplement or a vitamin, e.g., vitamin E, vitamin B12 or a folic acid supplement, or any equivalent or combination thereof.

In alternative embodiments, the at least one other (e.g., at least one additional, different) pharmaceutical composition, dosage form or formulation comprises a pain treatment or pain palliative or an anti-inflammatory drug, e.g., an ibuprofen (e.g., ADVIL™ MOTRIN™), naproxen sodium (ALEVE™), indomethacin (INDOCIN™), and any equivalent or combination thereof. The anti-inflammatory drug can comprise a non-steroidal anti-inflammatory drug (a NSAID), e.g., a cyclooxygenase (COX) (or prostaglandin synthase) inhibitor, e.g., an etodolac (e.g., LODINE™, LODINE SR™ or ECCOXOLAC™) naproxen, celecoxib, rofecoxib, etoricoxib, valdecoxib, parecoxib, nabumetone, diclofenac, lumiracoxib, or equivalent. The pain palliative can comprise a neuropathic pain analgesic such as gabapentin or pregabalin.

In alternative embodiments, the at least one other (e.g., at least one additional, different) pharmaceutical composition, dosage form or formulation comprises a tarenflurbil, or R-flurbiprofen (the single enantiomer of the racemate NSAID flurbiprofen), e.g., FLURIZAN™

In alternative embodiments, the at least one other (e.g., at least one additional, different) pharmaceutical composition, dosage form or formulation comprises an (S)-1-[N-(4-chlorobenzyl)succinamoyl]pyrrolidine-2-carbaldehyde (aka, ONO-1603), a prolyl endopeptidase inhibitor and anti-dementia drug.

In alternative embodiments, two or more or all of the drugs of a therapeutic, ameliorative and/or palliative combination (which includes at least one pharmaceutical composition, dosage form or formulation of this invention) are packaged individually, or are packaged together, or packaged in any combination, in a single package, a plurality of packages or packettes, or a blister packet, lidded blister or blister card or packets, or a shrink wrap.

In alternative embodiments, the invention provides a multi-ingredient kit comprising two or more or all of the drugs of a therapeutic, ameliorative and/or palliative combination (which includes at least one pharmaceutical composition, dosage form or formulation of this invention).

In alternative embodiments, the invention provides an ingredient or ingredients (which includes at least one pharmaceutical composition, dosage form or formulation of this invention) in a multi-ingredient kit of the invention separated by physical compartmentalization; e.g. in separate compartments that are part of a kit, where the kit is a multi-compartment kit. In alternative embodiments, separate compartments, e.g., as found in a "blister pack" type of packaging, contain different ingredients (including at least one pharmaceutical composition, dosage form or formulation of this invention)

In alternative embodiments, the invention provides a composition or product of manufacture formulated or made as a multiparticulate and/or a solid dispersion formulation, e.g., as described in, e.g., U.S. Patent App. Pub. No. 20080118560, e.g., comprising a hydrophobic matrix former which is a water-insoluble, non-swelling amphiphilic lipid; and a hydrophilic matrix former which is a meltable, water-soluble excipient. In one embodiment, the pharmaceutical composition, dosage form or formulation of the invention, or any composition, drug combination or product of manufacture of the invention, is/are contained in tablets, pills, capsules, troches, and the like comprising any combination of a binder, e.g., as a starch, polyvinyl pyrrolidone, gum tragacanth or gelatin; a filler, such as microcrystalline cellulose or lactose; a disintegrating agent, such as crospovidone, sodium starch glycolate, corn starch, and the like; a lubricant, such as magnesium stearate, stearic acid, glyceryl behenate; a glidant, such as colloidal silicon dioxide and talc; a sweetening agent, such as sucrose or saccharin, aspartame, acesulfame-K; and/or flavoring agent, such as peppermint, methyl salicylate, or orange flavoring. When the dosage unit form is a capsule, it also can comprise a liquid carrier, such as a fatty oil.

In alternative embodiments, a composition or product of manufacture of the invention comprises (or is contained or packaged in) unit dosage formulations having a coating, e.g., a coat comprising a sugar, shellac, sustained and/or other enteric coating agents, or any pharmaceutically pure and/or nontoxic agents.

In alternative embodiments, a composition or product of manufacture of the invention comprises (or is contained or packaged in) unit dosage formulations, wherein each different compound of the composition or product of manufacture is contained in a different layer of a pill, tablet or capsule, e.g., as described in U.S. Pat. No. 7,384,653, e.g., having an outer base-soluble layer and an inner acid-soluble layer. In alternative embodiments, a composition or product of manufacture of the invention comprises (or is contained or packaged in) unit dosage formulations, wherein each different compound of the composition or product of manufacture is contained in a liquid or a gel of different viscosity, e.g., described in U.S. Patent App. Pub. No. 20050214223. In alternative embodiments, a composition or product of manufacture of the invention comprises (or is contained or packaged in) unit dosage formulations having reduced abuse potential, e.g., as described in U.S. Patent App. Pub. No. 20040228802, e.g., comprising a bittering agent, a bright deterrent/indicator dye, or a fine insoluble particulate matter.

In alternative embodiments of the invention, a drug combination of the invention is formulated, packaged or designed for drug regimen compliance of a particular patient population, e.g., an Alzheimer's disease patient population, or a group of patients with dementia, or a pediatric or geriatric population, or a mentally compromised patient population. In alternative embodiments of the invention drug combination(s) of the invention are formulated, packaged or designed for drug regimen compliance of a particular patient population, e.g., a patient population having mild or severe mental retardation, slow cognition, dementia, senility, Alzheimer's disease, traumatic brain injury, chemical brain damage, mental diseases (e.g., dissociative disorder, obsessive-compulsive disorder, delusional disorder, schizophrenia, mania, panic disorder, depression, dyslexia, any learning disability and the like) posttraumatic stress disorder, traumatic war neurosis, post-traumatic stress syndrome (PTSS), physical disability (e.g., blindness).

In alternative embodiments the invention provides a blister pack or a plurality of blister packettes, a blister package, a lidded blister or a blister card or packet, a clamshell, a tray or a shrink wrap of the invention, or the paper, plastic or cellophane package or a plurality of packettes, wherein a drug combination (which includes at least one pharmaceutical composition, dosage form or formulation of this invention) is formulated, packaged or designed for drug regimen compliance of a particular patient population, e.g., an Alzheimer's disease patient population, or a group of patients with dementia, a pediatric or geriatric population, or a physically challenged or a mentally compromised patient population. In alternative embodiments, the invention provides blister pack or a plurality of blister packettes, a blister package, a lidded blister or a blister card or packet, a clamshell, a tray or a shrink wrap of the invention, or a paper, plastic or cellophane package or a plurality of packettes comprising a drug combination (which includes at least one pharmaceutical composition, dosage form or formulation of this invention) formulated, packaged or designed for drug regimen compliance of a particular patient population having mild or severe mental retardation, slow cognition, dementia, senility, Alzheimer's disease, traumatic brain injury, chemical brain damage, mental diseases (e.g., dissociative disorder, obsessive-compulsive disorder, delusional disorder, schizophrenia, mania, panic disorder, depression, dyslexia, any learning disability and the like) post-traumatic stress disorder, traumatic war neurosis, post-traumatic stress syndrome (PTSS), physical disability (e.g., blindness).

In alternative embodiments the invention provides a food or food supplement and a pharmaceutical composition, dosage form or formulation of this invention; or, a food or food supplement comprising a therapeutic combination or a drug combination (the combination including at least one pharmaceutical composition, dosage form or formulation of this invention). In alternative embodiments the invention provides feed or feed supplements comprising a pharmaceutical composition, dosage form or formulation of this invention; or, a therapeutic combination of the invention. In alternative embodiments the invention provides nutraceuticals comprising a pharmaceutical composition, dosage form or formulation of this invention; or, a therapeutic combination of the invention.

The following examples are provided to further illustrate the invention but not to limit its scope. Other variants of the invention will be readily apparent to one of ordinary skill in the art.

EXAMPLES

Standard procedures and chemical transformation and related methods are well known to one skilled in the art, and such methods and procedures have been described, for example, in standard references such as *Fiesers' Reagents for Organic Synthesis*, John Wiley and Sons, New York, N.Y., 2002; *Organic Reactions*, vols. 1-83, John Wiley and Sons, New York, N.Y., 2006; March J. and Smith M., *Advanced Organic Chemistry*, 6th ed., John Wiley and Sons, New York, N.Y.; and Larock R. C., *Comprehensive Organic Transformations*, Wiley-VCH Publishers, New York, 1999. All texts and references, patents and patent applications cited herein are expressly incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, *Protecting Groups in Organic Synthesis*, 3rd edition, John Wiley & Sons, Inc. 1999.

In alternative embodiments, compounds of Formula I can be prepared as shown in the following protocols, or schemes; and the invention encompasses methods for practicing all of the following protocols and schemes, including routine variations thereof.

Scheme I

In alternative embodiments, compounds of the invention, including compounds encompassed by Formula I, can be prepared using Scheme I, starting with a leucine derivative and an analog of isoamyl amine Reaction of the intermediate with an epoxide yielded a compound of Formula I.

Scheme 1

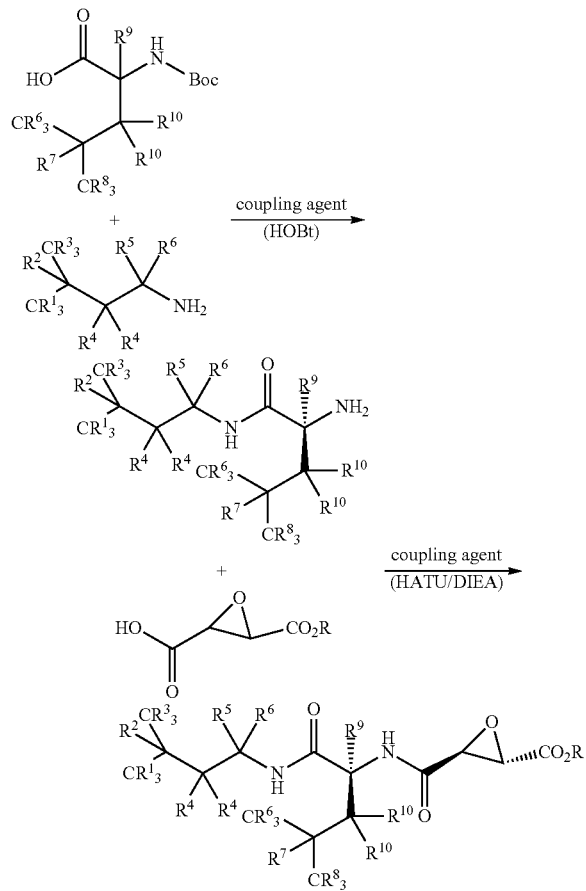

Example 1. Preparation of Compound 1A

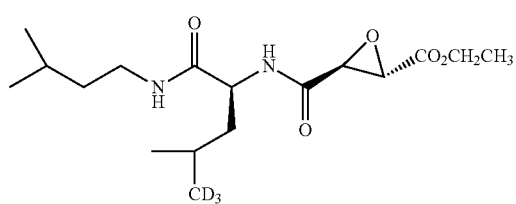

In alternative embodiments, compounds of the invention, including compounds of Formula I, can be prepared as shown in the following protocol or scheme; and the invention encompasses methods comprising this scheme and all routine variations thereof:

N-(tert-butyloxycarbonyl)-L-leucine-$d_3$ (methyl-$d_3$) hydrate (250 mg; 0.99 mmol; C/D/N Isotopes), 1-hydroxybenzotriazole hydrate (197 mg; 1.29 mmol), and isoamyl amine (95 mg; 1.09 mmol) were dissolved in $CH_2Cl_2$ (10 mL) at room temperature under nitrogen. With stirring, 1-ethyl-3-(3-dimethylaminopropyl)carbodiimide hydrochloride (288 mg; 1.50 mmol) was added. After stirring for three hours at room temperature, the reaction was diluted with $CH_2Cl_2$ (80 mL) and extracted with saturated $NaHCO_3$ (2×) and brine (1×). The organic layer was dried over anhydrous $Na_2SO_4$, filtered and concentrated to provide 313 mg of a waxy solid. This solid was dissolved in methanol (5 mL) and p-toluene sulfonic acid hydrate (237 mg; 1.25 mmol) was added with stirring. The solution was heated to 70° C. for four hours. After cooling, the reaction was evaporated to dryness and the residue treated with ether and hexanes. Removal of the volatiles provided a white foam. To this material was added (2S, 3S)-3-(ethoxycarbonyl)oxirane-2-carboxylic acid (160 mg; 1 mmol; Peptech) and $CH_2Cl_2$ (10 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (418 mg; 1.1 mmol) followed by diisopropylethyl amine (358 uL; 2 mmol) were added to the reaction solution. The resulting reaction was stirred at 0° C. for one hour and another hour at room temperature. The reaction was diluted with $CH_2Cl_2$ (100 ml) and extracted with saturated $NaHCO_3$ (2×) and brine (1×). The organic layer was dried over anhydrous $Na_2SO_4$, filtered and concentrated to provide a yellow solid. The crude product was filtered through a silica gel plug eluting with ethyl acetate-hexane (1:9) followed by ethyl acetate-hexane (1:1). Concentration of the 1:1 ethyl acetate-hexane elution fractions provided the desired product as a white solid (295 mg; 0.86 mmol; 86%). Recrystallization from diisopropyl ether-ethanol yielded Compound 1A, mp 122-123° C. $^1H$ NMR ($CDCl_3$, 500 MHz) δ6.71 (d, J=8.6 Hz, 1H), 6.12-6.14 (m, 1H), 4.36-4.41 (m, 1H), 4.21-4.29 (m, 2H), 3.67 (d, J=1.4 Hz, 1H), 3.46 (d, J=1.7 Hz, 1H), 3.20-3.28 (m, 2H), 1.56-1.64 (m, 2H), 1.50-1.55 (m, 2H), 1.38 (q, J=7.0 Hz, 2H), 1.30 (t, J=7.0 Hz, 3H), 0.89-0.92 (m, 9H). $^{13}C$ NMR ($CDCl_3$, 125 MHz) δ171.02, 166.71, 166.22, 62.53, 53.99, 53.11, 51.62, 41.41, 38.49, 38.21, 26.06, 24.81, 22.92, 22.62, 22.58, 22.32, 14.24, LCMS (ESI): m/z calculated (calcd) for $C_{12}H_{22}D_3N_2O_5$ 345.23, [M+H]$^+$ found 346.2.

Example 2. Preparation of Compound 1B

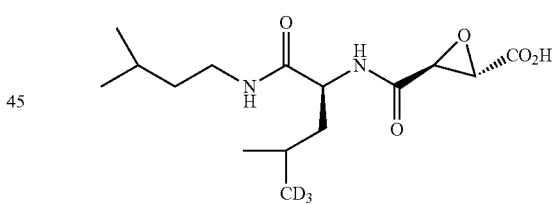

In alternative embodiments, compounds of the invention, including compounds of Formula I, can be prepared as shown in the following protocol or scheme; and the invention encompasses methods comprising this scheme and all routine variations thereof:

The ethyl ester Compound 1A (35 mg; 0.1 mmol) was dissolved in ethanol (2 mL). The stirred solution was cooled to 0° C. (ice-water bath) and treated with a solution of 85% KOH in ethanol (70 uL; 0.11 mmol). The resulting solution was stirred at 0° C. for 20 minutes and at room temperature for 10 minutes. The reaction was concentrated to dryness and the residue partitioned between water and ethyl acetate. The layers were separated and the aqueous extracted once more with ethyl acetate. The aqueous layer was acidified to pH 2 with 1N HCl and extracted with ethyl acetate (3×). The combined organic layers were dried over anhydrous $Na_2SO_4$, filtered and concentrated to provide a white solid, Compound 1B (36 mg; 96%). LCMS (ESI): m/z calcd for $C_{15}H_{23}D_3N_2O_5$ 317.20, [M+H]$^+$ found 318.2.

Example 3. Preparation of Compound 2A

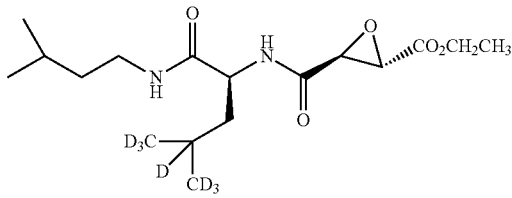

In alternative embodiments, compounds of the invention, including compounds of Formula I, can be prepared as shown in the following protocol or scheme; and the invention encompasses methods comprising this scheme and all routine variations thereof:

N-(tert-butyloxycarbonyl)-L-leucine-d$_7$ (isopropyl-d$_7$) hydrate (250 mg; 0.98 mmol; C/D/N Isotopes), 1-hydroxybenzotriazole hydrate (195 mg; 1.27 mmol), and isoamyl amine (94 mg; 1.07 mmol) were dissolved in $CH_2Cl_2$ (10 mL) at room temperature under nitrogen. With stirring, 1-ethyl-3-(3-dimethylaminopropyl)carbodiimide hydrochloride (282 mg; 1.47 mmol) was added. After stirring for three hours at room temperature, the reaction was diluted with $CH_2Cl_2$ (80 mL) and extracted with saturated $NaHCO_3$ (2×) and brine (1×). The organic layer was dried over anhydrous $Na_2SO_4$, filtered and concentrated to provide 315 mg of a white semi-solid. This material was dissolved in methanol (5 mL) and p-toluene sulfonic acid hydrate (237 mg; 1.25 mmol) was added with stirring. The solution was heated to 70° C. for four hours. After cooling, the reaction was evaporated to dryness and the residue treated with ether and hexanes. Removal of the volatiles provided a white foam. To this material was added (2S, 3S)-3-(ethoxycarbonyl)oxirane-2-carboxylic acid (160 mg; 1 mmol; Peptech) and $CH_2Cl_2$ (10 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (418 mg; 1.1 mmol) followed by diisopropylethyl amine (358 uL; 2 mmol) were added to the reaction solution. The resulting reaction was stirred at 0° C. for one hour and another hour at room temperature. The reaction was diluted with $CH_2Cl_2$ (100 ml) and extracted with saturated $NaHCO_3$ (2×) and brine (1×). The organic layer was dried over anhydrous $Na_2SO_4$, filtered and concentrated to provide a yellow solid. The crude product was filtered through a silica gel plug eluting with ethyl acetate-hexane (1:9) followed by ethyl acetate-hexane (1:1). Concentration of the 1:1 ethyl acetate-hexane elution fractions provided the desired product as a white solid (314 mg; 0.9 mmol; 90%). Recrystallization from diisopropyl ether yielded Compound 2A, mp 122-123° C. $^1$H NMR (CDCl$_3$, 500 MHz) δ 6.68 (d, J=8.6 Hz, 1H), 6.08-6.10 (m, 1H), 4.35-4.40 (m, 1H), 4.21-4.29 (m, 2H), 3.67 (d, J=1.8 Hz, 1H), 3.45 (d, J=1.7 Hz, 1H), 3.20-3.30 (m, 2H), 1.56-1.65 (m, 2H), 1.48-1.52 (m, 1H), 1.38 (q, J=7.3 Hz, 2H), 1.31 (t, J=7.2 Hz, 3H), 0.89-0.91 (d, J=6.6 Hz, 6H). $^{13}$C NMR (CDCl$_3$, 125 MHz) δ171.02, 166.70, 166.22, 62.54, 53.99, 53.11, 51.61, 41.23, 38.49, 38.21, 28.51 (weak), 26.06, 24.11 (m, weak), 22.62, 22.58, 14.24. LCMS (ESI): m/z calcd for $C_{12}H_{23}D_2N_2O_5$ 349.26, [M+H]$^+$ found 350.4.

Example 4. Preparation of Compound 2B

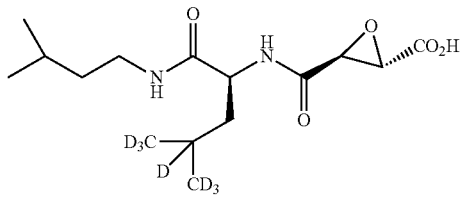 [SMILES: [2H]C([2H])([2H])C([2H])(C[C@H](NC(=O)[C@H]1O[C@@H]1C(=O)O)C(=O)NCCC(C)C)C([2H])([2H])[2H]]

In alternative embodiments, compounds of the invention, including compounds of Formula I, can be prepared as shown in the following protocol or scheme; and the invention encompasses methods comprising this scheme and all routine variations thereof:

The ethyl ester Compound 2A (36 mg; 0.1 mmol) was dissolved in ethanol (2 mL). The stirred solution was cooled to 0° C. (ice-water bath) and treated with a solution of 85% KOH in ethanol (70 uL; 0.11 mmol). The resulting solution was stirred at 0° C. for 20 minutes and at room temperature for 10 minutes. The reaction was concentrated to dryness and the residue partitioned between water and ethyl acetate. The layers were separated and the aqueous extracted once more with ethyl acetate. The aqueous layer was acidified to pH 2 with 1N HCl and extracted with ethyl acetate (3×). The combined organic layers were dried over anhydrous $Na_2SO_4$, filtered and concentrated to provide an off-white powder, Compound 2B (32 mg; 97%). LCMS (ESI): m/z calcd for $C_{15}H_{19}D7N_2O_5$ 321.23, [M+H]$^+$ found 322.2.

Example 5. Preparation of Compound 3A

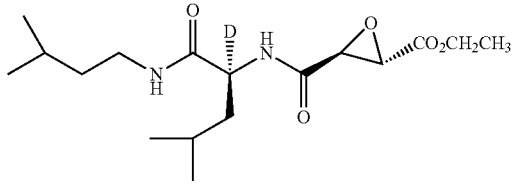

In alternative embodiments, compounds of the invention, including compounds of Formula I, can be prepared as shown in the following protocol or scheme; and the invention encompasses methods comprising this scheme and all routine variations thereof:

L-Leucine-2-di (188 mg; 1.4 mmol; C/D/N Isotopes) was suspended in 8 mL of a 1:1 solution of water and tetrahydrofuran. The suspension was stirred, cooled to 0° C. (ice-water bath), and treated with sodium bicarbonate (353 mg; 4.2 mmol) followed by di-tert-butyl dicarbonate (373 mg; 1.7 mmol). The resulting suspension was stirred at 0° C. for 30 minutes and then at room temperature for 68 hours. The reaction mixture was extracted with ethyl acetate (3×). The aqueous layer was acidified to pH=3 with 1 N HCl and extracted with ethyl acetate (3×). All of the ethyl acetate extractions were combined, washed with brine (3×), dried over anhydrous $Na_2SO_4$, filtered and concentrated to provide a viscous oil (317 mg) of N-(tert-butyloxycarbonyl)-L-leucine-2-di. N-(tert-butyloxycarbonyl)-L-leucine-2-di (405 mg; 1.74 mmol), 1-hydroxybenzotriazole hydrate (346 mg; 2.26 mmol), and isoamyl amine (166 mg; 1.91 mmol) were dissolved in $CH_2Cl_2$ (10 mL) at room temperature under nitrogen. With stirring, 1-ethyl-3-(3-dimethylaminopropyl)carbodiimide hydrochloride (500 mg; 2.61 mmol) was added. After stirring for three hours at room temperature, the reaction was diluted with $CH_2Cl_2$ (80 mL) and extracted with saturated $NaHCO_3$ (2×) and brine (1×). The organic layer was dried over anhydrous $Na_2SO_4$, filtered and concentrated to provide 525 mg of crude product. This material was dissolved in methanol (9 mL) and p-toluene sulfonic acid hydrate (414 mg; 2.18 mmol) was added with stirring. The solution was heated to 70° C. for two hours. After cooling, the reaction was evaporated to dryness to provide 279 mg of crude product. To this material was added (2S, 3S)-3-(ethoxycarbonyl)oxirane-2-carboxylic acid (279 mg; 1.74 mmol; Peptech) and $CH_2Cl_2$ (15 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (722 mg; 1.9 mmol) followed by diisopropylethyl amine (779 uL; 4.35 mmol) were added to the reaction solution. The resulting reaction was stirred at 0° C. for one hour and for two hours at room temperature. The reaction was diluted with $CH_2Cl_2$ (150 ml) and extracted with saturated $NaHCO_3$ (2×) and brine (1×). The organic layer was dried over anhydrous $Na_2SO_4$, filtered and concentrated. The crude product was filtered through a silica gel plug eluting with ethyl acetate-hexane (1:9) followed by ethyl acetate-hexane (1:1). Concentration of the 1:1 ethyl acetate-hexane elution fractions provided the desired product as a white solid (468 mg; 78%). Recrystallization from diisopropyl ether yielded crystalline material, mp 122-123° C. $^1H$ NMR ($CDCl_3$, 500 MHz) $\delta$6.95 (s, 1H), 6.43 (bt, J=5.4 Hz, 1H), 4.19-4.27 (m, 2H), 3.67 (d, J=1.8 Hz, 1H), 3.46 (d, J=1.8 Hz, 1H), 3.23-3.30 (m, 1H), 3.14-3.20 (m, 1H), 1.49-1.62 m, 4H), 1.36 (q, J=7.3 Hz, 2H), 1.29 (t, J=7.2 Hz, 3H), 0.87-0.91 (m, 12H). $^{13}C$ NMR ($CDCl_3$, 125 MHz) $\delta$171.16, 166.81, 166.20, 62.47, 53.93, 52.96, 51.37 (m, weak), 41.40, 38.42, 38.14, 26.02, 24.99, 22.95, 22.59, 22.54, 22.41, 14.19. LCMS (ESI): m/z calcd for $C_{17}H_{29}DN_2O_5$ 343.22, $[M+H]^+$ found 344.2.

Example 6. Preparation of Compound 3B

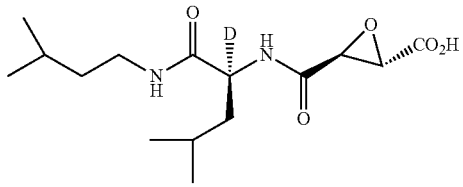

In alternative embodiments, compounds of the invention, including compounds of Formula I, can be prepared as shown in the following protocol or scheme; and the invention encompasses methods comprising this scheme and all routine variations thereof:

The ethyl ester from the above preparation (68 mg; 0.2 mmol) was dissolved in ethanol (3 mL). The stirred solution was cooled to 0° C. (ice-water bath) and treated with a solution of 85% KOH in ethanol (140 uL; 0.22 mmol). The resulting solution was stirred at 0° C. for 60 minutes and was concentrated to dryness. The residue partitioned between water and ethyl acetate. The layers were separated and the aqueous extracted once more with ethyl acetate. The aqueous layer was acidified to pH 1 with 1N HCl and extracted with ethyl acetate (3×). The combined organic layers were dried over anhydrous $Na_2SO_4$, filtered and concentrated to provide an white powder (42 mg; 67%). LCMS (ESI): m/z calcd for $C_{15}H_{25}DN_2O_5$ 315.19, $[M+H]^+$ found 316.2.

Example 6. $IC_{50}$ of Metabolically Blocked Analogs

In alternative embodiments, compounds of the invention, including compounds of Formula I, can be prepared as shown in the following protocol or scheme; and the invention encompasses methods comprising this scheme and all routine variations thereof:

The $IC_{50}$ of Compound 1B, Compound 2B, and Compound 3B were determined and compared to the $IC_{50}$ of E64c in a series of assays evaluating the inhibition of Cathepsin B in the manner well known to those of skill in the art. The measured values are reported in Table 1.

TABLE 1

| Enzymatic activity vs Cathepsin B | |
|---|---|
| Compound | $IC_{50}$ |
| E64c | 1 nM |
| Compound 1B | 2 nM |
| Compound 2B | 1.5 nM |
| Compound 3B | 1.9 nM |

Example 7

In alternative embodiments, compounds of the invention, including compounds of Formula I, can be prepared as shown in the following protocols or schemes; and the invention encompasses methods comprising these schemes and protocols and all routine variations thereof:

Scheme 1. Synthesis of tertiary alcohol analogue of E64C 6[a]

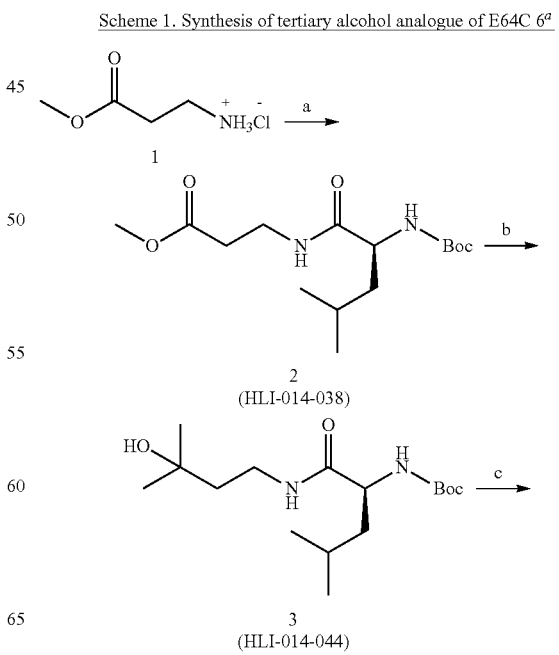

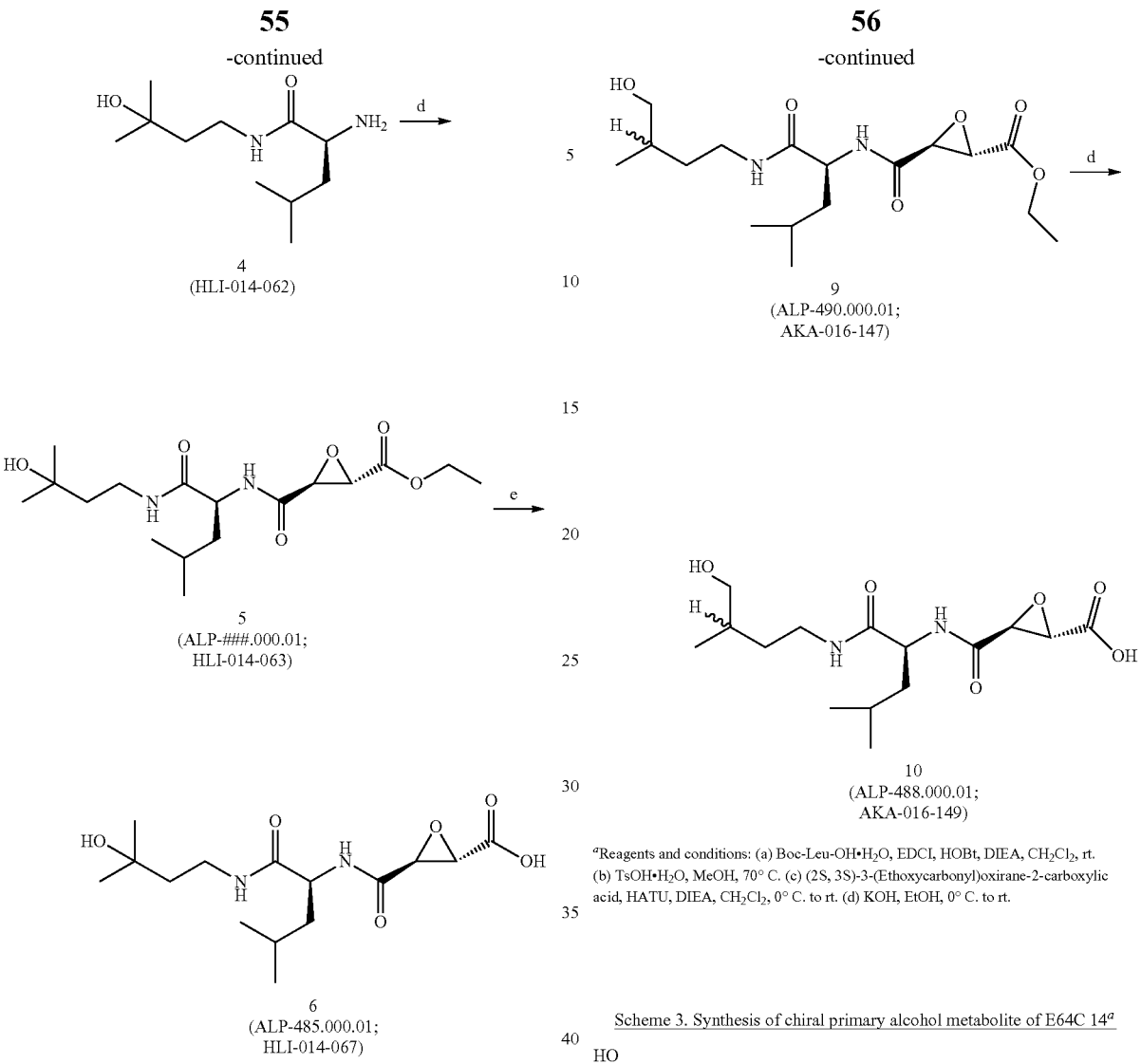

<sup>a</sup>Reagents and conditions: (a) Boc-Leu-OH·H₂O, EDCI, HOBt, DIEA, CH₂Cl₂, rt. (b) TsOH·H₂O, MeOH, 70° C. (c) (2S, 3S)-3-(Ethoxycarbonyl)oxirane-2-carboxylic acid, HATU, DIEA, CH₂Cl₂, 0° C. to rt. (d) KOH, EtOH, 0° C. to rt.

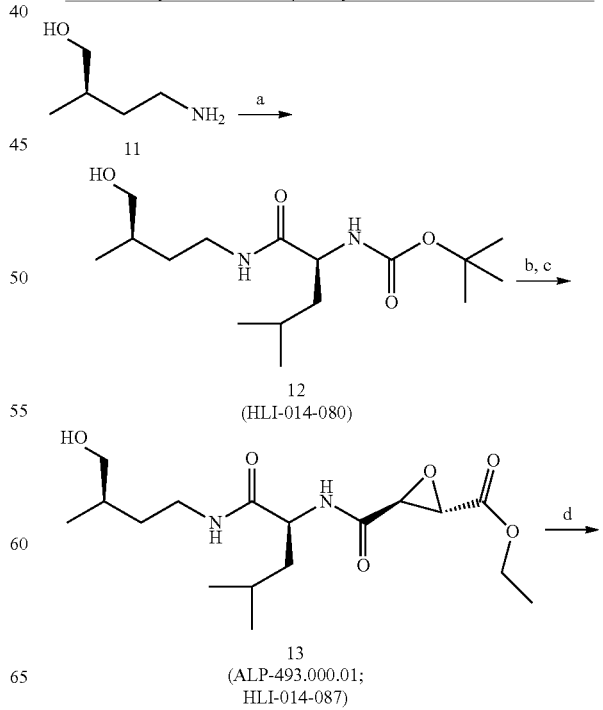

<sup>a</sup>Reagents and conditions: (a) Boc-Leu-OH·H₂O, EDCI, HOBt, DIEA, CH₂Cl₂, rt. (b) MeMgBr, THF, rt. (c) TsOH·H₂O, dioxane-H₂O, 70° C.; NH₄OH. (d) (2S, 3S)-3-(Ethoxycarbonyl)oxirane-2-carboxylic acid, HATU, DIEA, CH₂Cl₂, 0° C. to rt. (e) KOH, EtOH, rt.

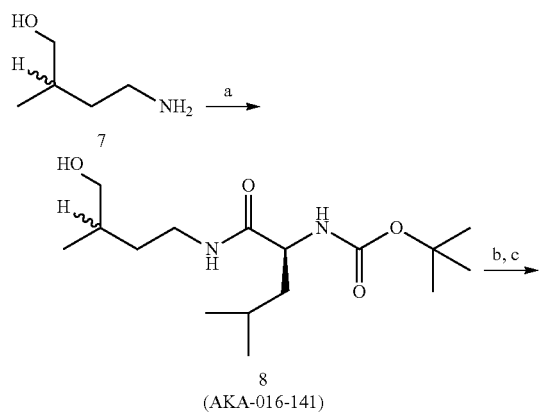

57

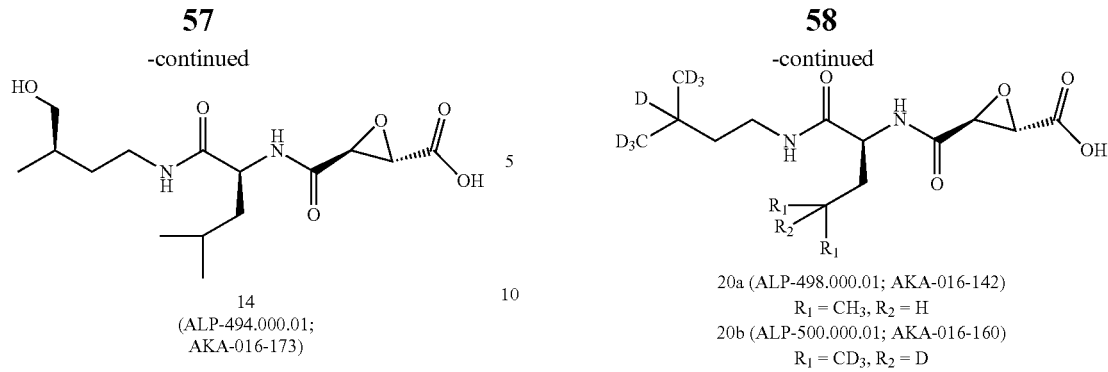

14
(ALP-494.000.01;
AKA-016-173)

*Reagents and conditions: (a) Boc-Leu-OH•H₂O, HATU, DIEA, CH₂Cl₂, 0° C. to rt. (b) TsOH•H₂O, MeOH, 65° C. (c) (2S, 3S)-3-(Ethoxycarbonyl)oxirane-2-carboxylic acid, HATU, DIEA, CH₂Cl₂, 0° C. to rt. (d) KOH, EtOH, 0° C. to rt.

Scheme 4. Synthesis of deuterated isoamyl analogues of E64c 20a and 20b$^a$

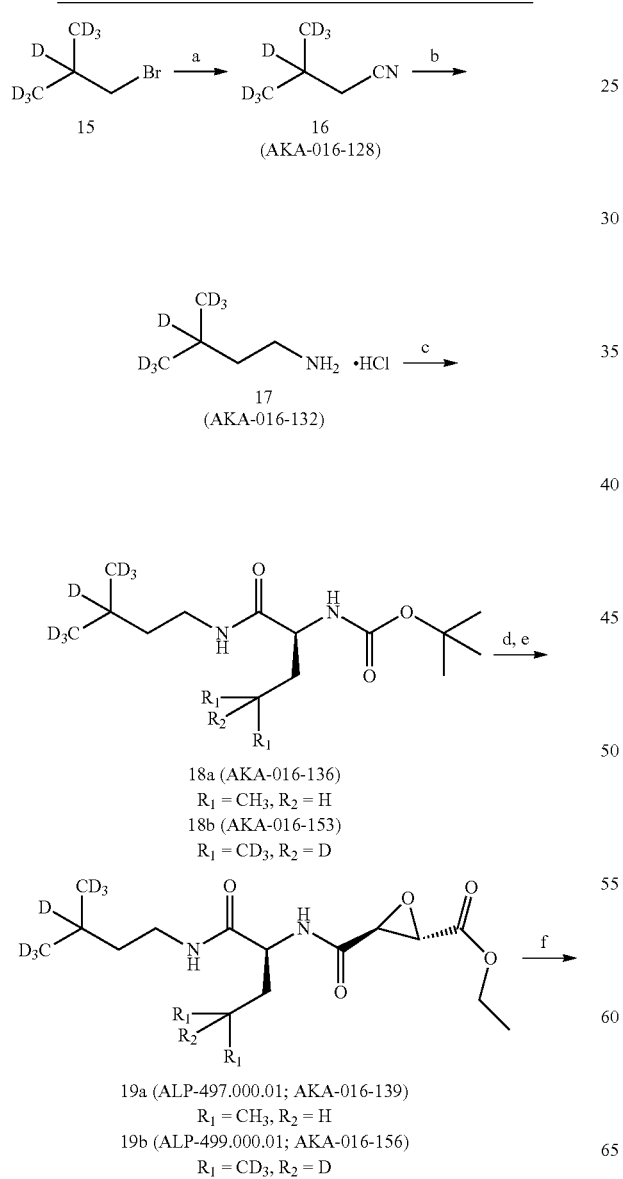

58

20a (ALP-498.000.01; AKA-016-142)
$R_1 = CH_3, R_2 = H$
20b (ALP-500.000.01; AKA-016-160)
$R_1 = CD_3, R_2 = D$

*Reagents and conditions: (a) KCN, EtOH/H₂O, 90° C. (b) LiAlH₄, THF, 0° C. to room temperature (rt); 4N HCl/dioxane, 0° C., (c) Boc-Leu-OH•H₂O, EDCI, HOBt, DIEA, CH₂Cl₂, rt. (d) TsOH•H₂O, MeOH, 70° C. (e) (2S, 3S)-3-(Ethoxycarbonyl)oxirane-2-carboxylic acid, HATU, DIEA, CH₂Cl₂, 0° C. to rt. (f) KOH, EtOH, 0° C. to rt.

Scheme 5. Synthesis of deuterated isoamyl analogue of E64c 25$^a$

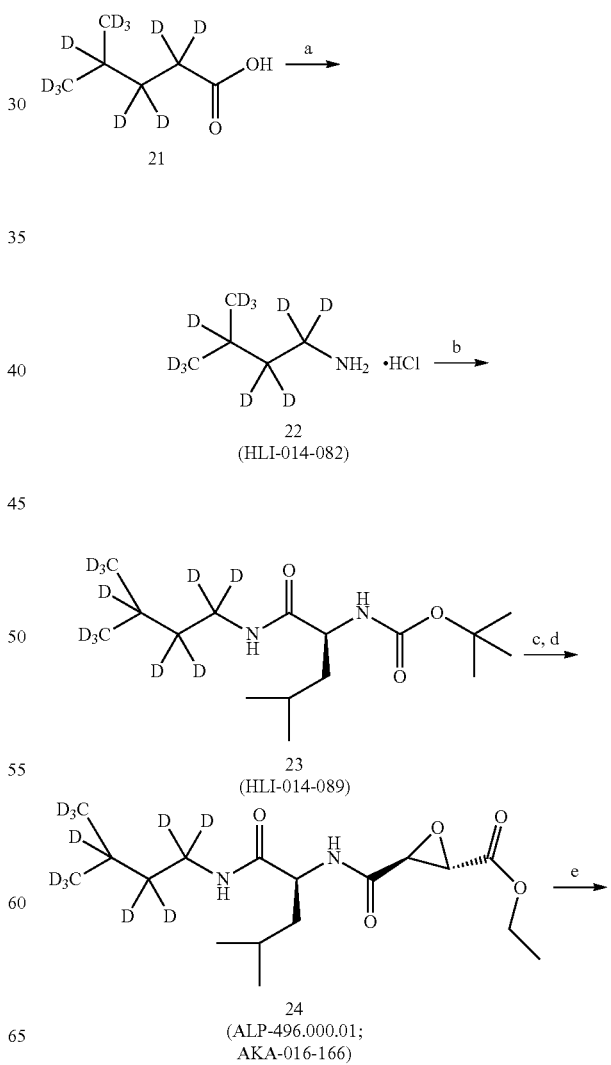

-continued

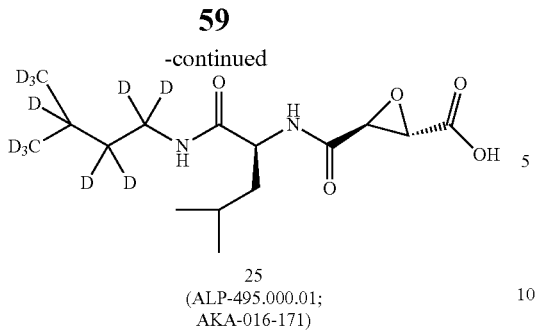

25
(ALP-495.000.01;
AKA-016-171)

*Reagents and conditions: (a) NaN₃, n-Bu₄NBr, Zn(OTf)₂, (Boc)₂O, THF, 40° C.; THF, 85° C.; HCl (b) Boc-Leu-OH•H₂O, EDCI, HOBt, DIEA, CH₂Cl₂, rt. (c) TsOH•H₂O, MeOH, 70° C. (d) (2S, 3S)-3-(Ethoxycarbonyl)oxirane-2-carboxylic acid, HATU, DIEA, CH₂Cl₂, 0° C. to rt. (e) KOH, EtOH, 0° C. to rt.

-continued

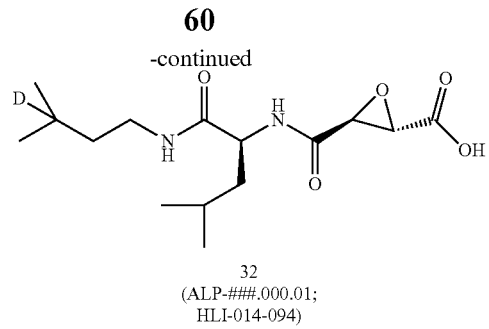

32
(ALP-###.000.01;
HLI-014-094)

*Reagents and conditions: (a) Ethyl cyanoacetate, K₂CO₃, CH₃CN, rt to 65° C. (b) LiOH, THF, H₂O, rt. (c) Cu powder, 200° C. (d) LAH, THF, 0° C. to rt; 4N HCl/dioxane, 0° C. (e) Boc-Leu-OH•H₂O, EDCI, HOBt, DIEA, CH₂Cl₂, rt. (f) TsOH•H₂O, MeOH, 70° C. (g) (2S, 3S)-3-(Ethoxycarbonyl)-oxirane-2-carboxylic acid, HATU, DIEA, CH₂Cl₂, 5° C. to rt. (h) KOH, EtOH, rt.

Scheme 6. Synthesis of monodeuterated isoamyl analogue of E64c 32ᵃ

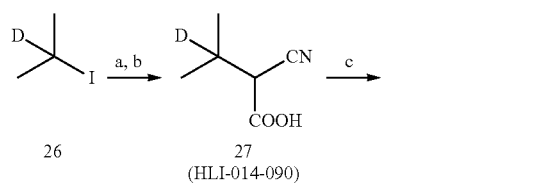

26    27
      (HLI-014-090)

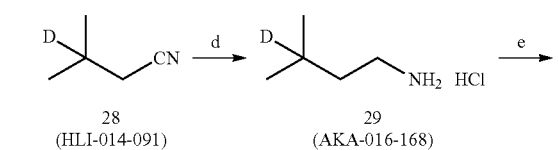

28              29
(HLI-014-091)   (AKA-016-168)

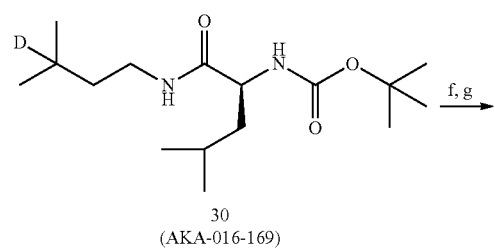

30
(AKA-016-169)

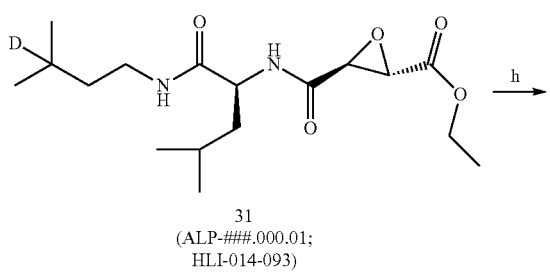

31
(ALP-###.000.01;
HLI-014-093)

Scheme 7. Synthesis of deuterated leucine analogue of E64c 36ᵃ

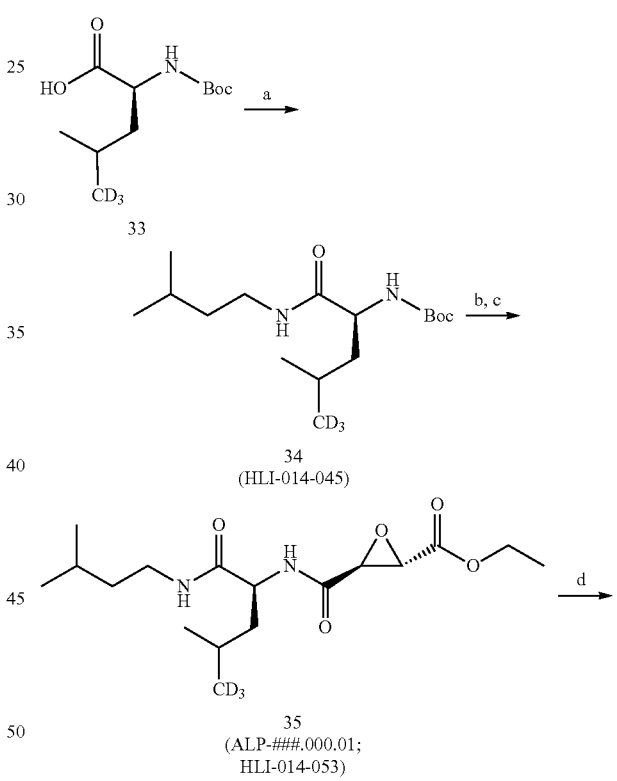

33

34
(HLI-014-045)

35
(ALP-###.000.01;
HLI-014-053)

36
(ALP-481.000.01;
HLi-014-057)

*Reagents and conditions: (a) Isoamylamine, EDCI, HOBt, CH₂Cl₂, rt. (b) TsOH•H₂O, MeOH, 70° C. (c) (2S, 3S)-3-(Ethoxycarbonyl)-oxirane-2-carboxylic acid, HATU, DIEA, CH₂Cl₂, 0° C. to rt. (d) KOH, EtOH, 0° C. to rt.

Scheme 8. Synthesis of deuterated leucine analogue of E64c 40[a]

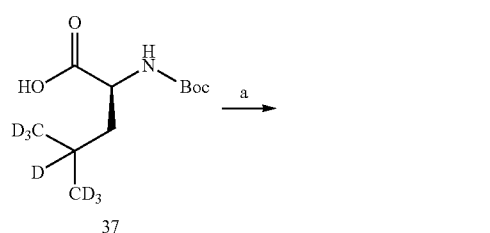

37

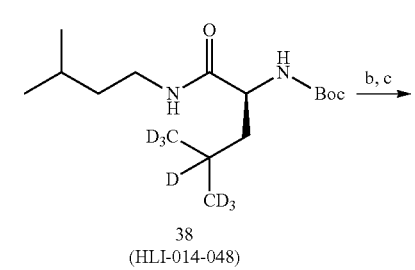

38
(HLI-014-048)

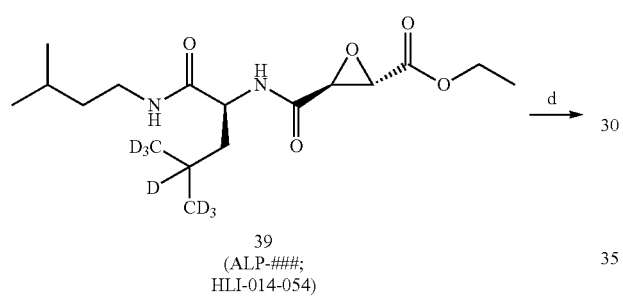

39
(ALP-###;
HLI-014-054)

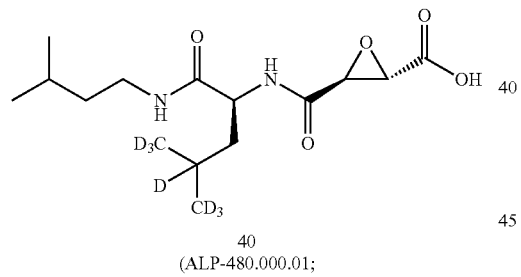

40
(ALP-480.000.01;
HLI-014-058)

[a]Reagents and conditions: (a) Isoamylamine, EDCI, HOBt, CH$_2$Cl$_2$, rt.
(b) TsOH·H$_2$O, MeOH, 70° C. (c) (2S, 3S)-3-(Ethoxycarbonyl)-oxirane-2-carboxylic acid, HATU, DIEA, CH$_2$Cl$_2$, 0° C. to rt. (d) KOH, EtOH, 0° C. to rt.

Scheme 9. Synthesis of monodeuterated leucine analogue of E64c 44[a]

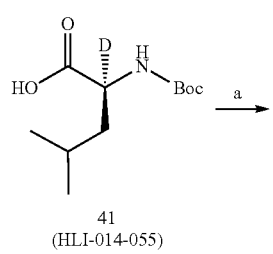

41
(HLI-014-055)

-continued

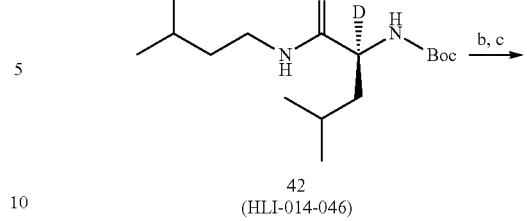

42
(HLI-014-046)

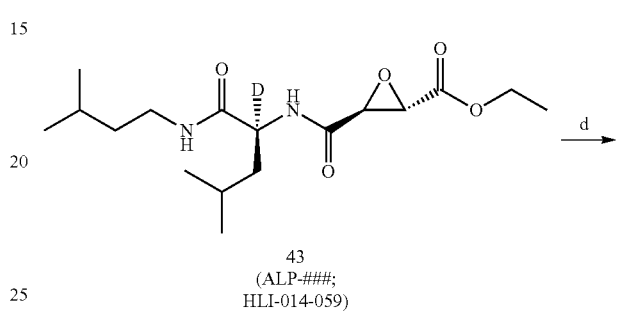

43
(ALP-###;
HLI-014-059)

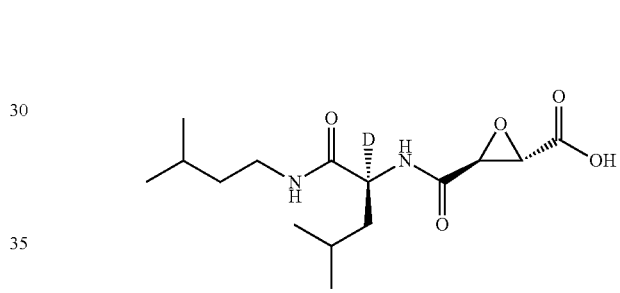

44
(ALP-479.000.01;
HLI-014-060)

[a]Reagents and conditions: (a) Isoamylamine, EDCI, HOBt, CH$_2$Cl$_2$, rt.
(b) TsOH·H$_2$O, MeOH, 70° C. (c) (2S, 3S)-3-(Ethoxycarbonyl)-oxirane-2-carboxylic acid, HATU, DIEA, CH$_2$Cl$_2$, 0° C. to rt. (d) KOH, EtOH, 0° C.

Scheme 10. Synthesis of deuterated leucine analogue of E64c 48[a]

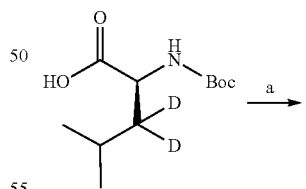

45
(HLI-014-065)

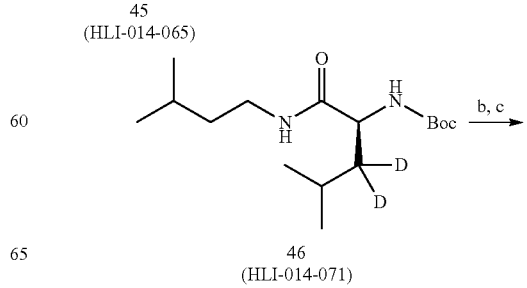

46
(HLI-014-071)

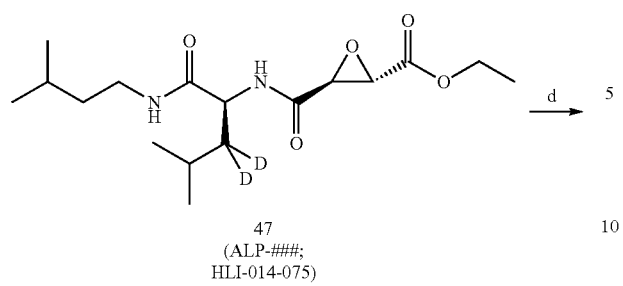

47
(ALP-###;
HLI-014-075)

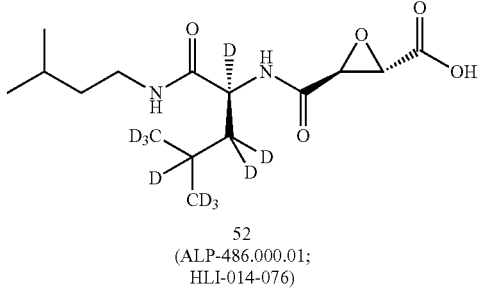

52
(ALP-486.000.01;
HLI-014-076)

<sup>a</sup>Reagents and conditions: (a) Isoamylamine, EDCI, HOBt, CH$_2$Cl$_2$, rt.
(b) TsOH·H$_2$O, MeOH, 70° C. (c) (2S, 3S)-3-(Ethoxycarbonyl)-oxirane-2-carboxylic acid, HATU, DIEA, CH$_2$Cl$_2$, 0° C. to rt. (d) KOH, EtOH, rt.

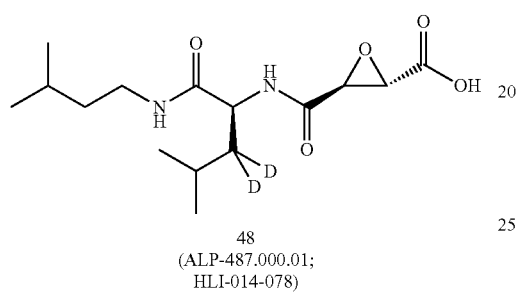

48
(ALP-487.000.01;
HLI-014-078)

<sup>a</sup>Reagents and conditions: (a) Isoamylamine, EDCI, HOBt, CH$_2$Cl$_2$, rt.
(b) TsOH·H$_2$O, MeOH, 70° C. (c) (2S, 3S)-3-(Ethoxycarbonyl)-oxirane-2-carboxylic acid, HATU, DIEA, CH$_2$Cl$_2$, 0° C. to rt. (d) KOH, EtOH, rt.

Scheme 11. Synthesis of deuterated leucine analogue of E64c 52<sup>a</sup>

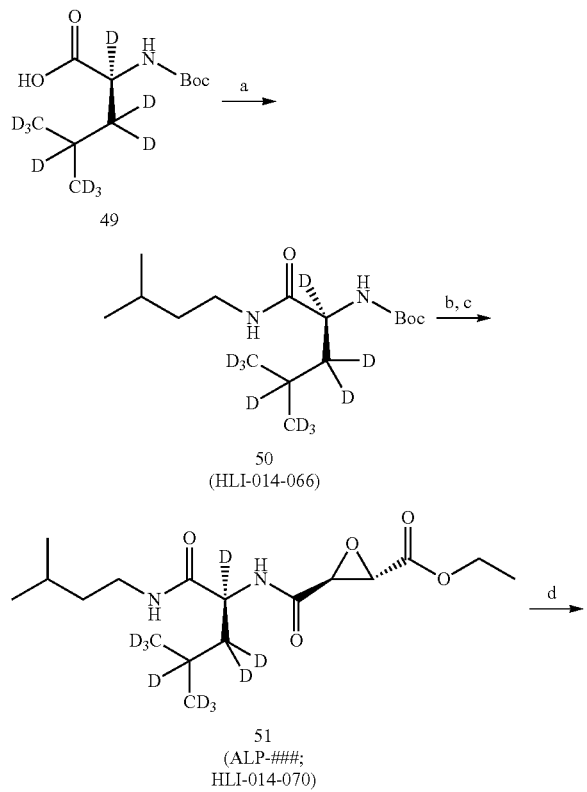

49

50
(HLI-014-066)

51
(ALP-###;
HLI-014-070)

EXPERIMENTAL SECTION

General Experimental Procedures. All commercially available reagents were used without further purification unless otherwise specified. Analytical TLC was performed on EMD precoated silica gel 60 F254 plates with 0.25 mm thickness. Flash column chromatography was carried out using Davisil Grade 63 FC Type 60A silica gel (170-400 mesh) or with pre-packed REVELERIS™ (Grace, Deerfield, Ill.) High Resolution Flash Cartridges. NMR spectra were obtained on a 500 MHz spectrometer at 500 MHz for $^1$H NMR and 125 MHz for $^{13}$C NMR with chemical shifts reported in units of parts per million (ppm). Mass spectra (MS) were recorded on a PE/SCIEX API-150EX™ (AB SCIEX, Foster City, Calif.) mass spectrometer using ESI. The purity of tested compounds were analyzed on an HPLC equipped with a Waters 1525™ pump, a Waters 2487™ dual λ, Absorbance detector, a Waters 717™ (Waters, Milford, Mass.) Plus autosampler and a LUNA™ (Phenomenex, Torrance, Calif.) C18(2) 100 mm×4.6 mm reverse-phase column using a gradient (see Table 1) with solvents [A] 0.1% trifluoroacetic acid in water and [B] 0.1% trifluoroacetic acid in acetonitrile with a flow rate of 1 mL/min.

TABLE 1

| Solvent gradient for condition I | | | | |
|---|---|---|---|---|
| Step | Time (min) | Flow (ml/min) | % A | % B |
| 1 | 0.00 | 1.00 | 90.0 | 10.0 |
| 2 | 5.00 | 1.00 | 90.0 | 10.0 |
| 3 | 15.00 | 1.00 | 60.0 | 40.0 |
| 4 | 45.00 | 1.00 | 45.0 | 55.0 |
| 5 | 47.00 | 1.00 | 0.0 | 100 |
| 6 | 50.00 | 1.00 | 0.0 | 100 |
| 7 | 51.00 | 1.00 | 90.0 | 10.0 |

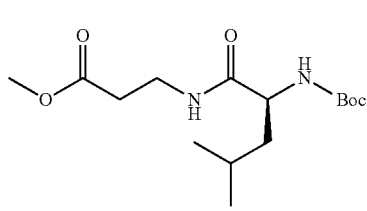

2

(HLI-014-038)

3-(2-tert-Butoxycarbonylamino-4-methylpentanoylamino)-propionic acid methyl ester (HLI-014-038) (2)

N-(tert-butyloxycarbonyl)-L-leucine hydrate (1.50 g, 6.0 mmol), 1-hydroxybenzotriazole hydrate (1.11 g, 7.8 mmol), and B-alanine methyl ester hydrochloride (1) (0.92 g, 6.6 mmol) were dissolved in $CH_2Cl_2$ (50 mL) at room temperature under nitrogen. With stirring, diisopropylethylamine (1.08 mL, 6.0 mmol) was added into the reaction mixture, followed by 1-ethyl-3-(3-dimethylaminopropyl)carbodiimide hydrochloride (1.73 g, 9.0 mmol) at rt. After stirring for five hours at room temperature, the reaction was diluted with $CH_2Cl_2$ (100 mL) and extracted with saturated $NaHCO_3$ (2×) and brine (2×). The organic layer was dried over anhydrous $Na_2SO_4$, filtered and concentrated to provide compound 2 (1.90 g, 100%) as a white waxy solid: ESI MS m/z 317.2 $(M+H)^+$.

2-Amino-4-methylpentanoic acid (3-hydroxy-3-methylbutyl)amide (HLI-014-062) (4)

Boc protected material 3 (0.080 g, 0.25 mmol) was dissolved in a mixture of dioxane (3 mL) and water (1 mL) and then treated with p-toluenesulfonic acid hydrate (0.071 g, 0.38 mmol) with stirring. The solution was heated to 70° C. for six and half hours. After cooling, the reaction was concentrated under reduced pressure at room temperature and the remaining liquid was treated with 28% $NH_4OH$ aqueous solution to pH 10. The resulting mixture was extracted with dichloromethane (3×) and the combined extracts were dried over $Na_2SO_4$, filtered, concentrated to provide amine 4 as an off-white viscous oil (0.054, 99%); ESI MS m/z 217.2 $(M+H)^+$. This material was used in the next step without further purification.

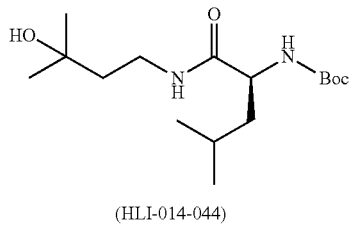

(HLI-014-044)

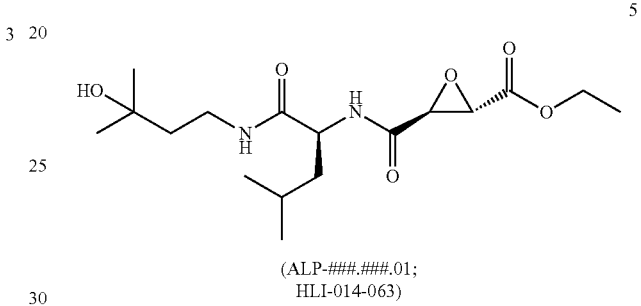

(ALP-###.###.01; HLI-014-063)

[1-(3-Hydroxy-3-methyl-butylcarbamoyl-3-methyl-butyl]carbamic acid tert-butyl ester (HLI-014-044) (3)

Compound 2 (0.158 g; 0.5 mmol) was dissolved in anhydrous THF (3 mL) and then treated with a solution of methyl magnesium bromide in diethyl ether (3.0 M, 1.00 mL, 3.0 mmol) under nitrogen with stirring. The solution was stirred at room temperature for 20 hours and then quenched with saturated $NH_4Cl$ aqueous solution. The resulting mixture was extracted with ethyl acetate (3×). The combined ethyl acetate layers were washed with saturated $NH_4Cl$ aqueous solution (3×) and brine (1×). The organic layer was dried over anhydrous $Na_2SO_4$, filtered and concentrated to provide alcohol 3 as a white foam. The crude product was filtered through a silica gel plug eluting with ethyl acetate-hexane (1:9 to 1:1). Concentration of the 1:1 ethyl acetate-hexane elution fractions provided the pure compound 3 as a white viscous oil (0.105 g; 0.33 mmol, 66%); $^1$H NMR ($CDCl_3$, 500 MHz) δ 6.85 (br s, 1H), 4.96 (d, J=8.1 Hz, 1H), 3.98-4.05 (m, 1H), 3.42-3.48 (m, 1H), 3.31-3.38 (m, 1H), 1.77-1.82 (m, 1H), 1.67 (t, J=6.6 Hz, 2H), 1.60-1.68 (m, 2H), 1.43 (s, 9H), 1.26 (s, 3H), 1.25 (s, 3H), 0.91-0.95 (m, 6H); ESI MS m/z 317.2 $(M+H)^+$.

(2S,3S)-3-((S)-[1-(3-Hydroxy-3-methylbutylcarbamoyl)-3-methylbutylcarbamoyl]-oxirane-2-carboxylic acid ethyl ester (ALP-###.000.01; HLI-014-063) (5)

To crude amine 4 (0.070 g, 0.32 mmol) was added (2S,3S)-3-(ethoxycarbonyl)oxirane-2-carboxylic acid (0.054 g, 0.34 mmol, Peptech) and $CH_2Cl_2$ (4 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (0.13 g, 0.35 mmol) followed by diisopropylethylamine (0.12 mL, 0.68 mmol) were added to the reaction solution. The resulting reaction was stirred at 0° C. for one hour and two and half hours at room temperature. The reaction was diluted with $CH_2Cl_2$ (80 ml) and extracted with saturated $NaHCO_3$ (2×) and brine (1×). The organic layer was dried over anhydrous $Na_2SO_4$, filtered and concentrated to provide crude 32 as a yellow, viscous oil. The crude product was filtered through a silica gel plug eluting with ethyl acetate-hexane (1:9) to pure ethyl acetate. Concentration of elution fractions provided the title compound as a clear, viscous oil (0.075 g, 65%). Treatment of this oil with diethyl ether-hexanes yielded compound 5 as a white solid; $^1$H NMR ($CDCl_3$, 500 MHz) δ 6.91 (br s, 1H), 6.64 (d, J=8.2 Hz, 1H), 4.32-4.37 (m, 1H), 4.21-4.31 (m, 2H), 3.68 (s, 1H), 3.47 (s, 1H), 3.37-3.44 (m, 2H), 1.91 (s, 1H), 1.67 (t, J=6.5 Hz, 2H), 1.63-1.65 (m, 1H), 1.49-1.59 (m, 2H), 1.31 (t, J=7.1 Hz, 3H), 1.27 (s, 3H), 1.26 (s, 3H), 0.90-0.93 (m, 6H); ESI MS m/z 359.4 $(M+H)^+$.

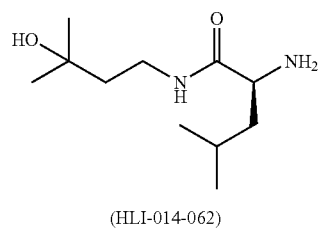

(HLI-014-062)

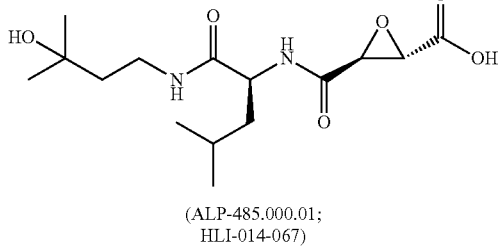

(ALP-485.000.01;
HLI-014-067)

(2S,3S)-3-((S)-1-(3-hydroxy-3-methylbutylamino)-
4-methyl-1-oxopentan-2-ylcarbamoyl)oxirane-2-
carboxylic acid (ALP-485.000.01; HLI-014-067)
(6)

Ethyl ester 5 (25 mg, 0.07 mmol) was dissolved in ethanol (3.0 mL). The stirred solution was treated with a solution of 85% KOH in ethanol (100 µL, 0.07 mmol). The resulting solution was stirred at room temperature for 30 minutes. The reaction was acidified to pH 4 with a solution of HCl in dioxane and ethanol. The mixture was filtered through a pad of Celite (diatomaceous earth) and concentrated to afford acid 33 as a colorless viscous oil (23 mg, 100%); $^1$H NMR (acetone-$d_6$, 500 MHz) δ 7.65 (br s, 1H), 7.56 (br s, 1H), 4.44 (t, J=7.4 Hz, 1H), 3.66 (s, 1H), 3.56 (s, 1H), 3.31 (t, J=6.2 Hz, 2H), 2.09 (s, 1H), 1.61-1.70 (m, 5H), 1.19 (s, 6H), 0.88-0.93 (m, 6H); ESI MS m/z 331.0 (M+H)$^+$.

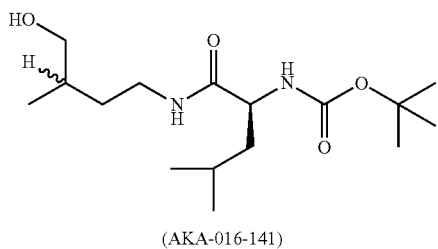

(AKA-016-141)

[1-(4-Hydroxy-3-methylbutylcarbamoyl)-3-methyl-
butyl]-carbamic acid tert-butyl ester (AKA-016-
141) (8)

To a solution of Boc-Leu-OH.H$_2$O (2.30 g, 9.23 mmol) in CH$_2$Cl$_2$ (100 mL) under nitrogen at room temperature was added 1-hydroxybenzotriazole hydrate (1.84 g, 12.00 mmol), 1-ethyl-3(3-dimethyl aminopropyl)carbodiimide hydrochloride (2.65 g, 13.85 mmol) and 4-amino-2-methylbutanol (1.00 g, 9.69 mmol, Ryan Scientific). After stirring for 5 h at rt, the reaction mixture was diluted with CH$_2$Cl$_2$ (200 mL) and the organics were washed with saturated NaHCO$_3$ (2×), brine (1×), dried over anhydrous Na$_2$SO$_4$, filtered and concentrated to provide a white foam. Purification by silica gel chromatography (elution with 33% to 50% to 80% ethyl acetate/hexanes) gave a mixture of diastereomers 8 (2.53 g, 87%) as a colorless foam: TLC R$_f$ 0.49 (EtOAc; Ninhydrin stain); $^1$H NMR CDCl$_3$, 500 MHz) δ 6.70 (bs, 1H), 5.07-5.09 (m, 1H), 4.05 (bs, 1), 3.49-3.53 (m, 1H), 3.20-3.43 (m, 3H), 2.71-2.78 (m, 1H), 1.57-1.70 (m, 4H), 1.46-1.48 (m, 2H), 1.42 (s, 9H), 0.89-0.94 (m, 9H); $^{13}$C NMR (CDCl$_3$, 125 MHz) δ 172.89, 156.07, 80.26, 67.85, 53.45, 41.56, 37.76 (37.63), 33.76 (33.69), 33.51 (33.45), 28.53, 24.97, 23.10, 22.26, 17.16 (17.07); ESI MS m/z 317.4 (M+H)$^+$.

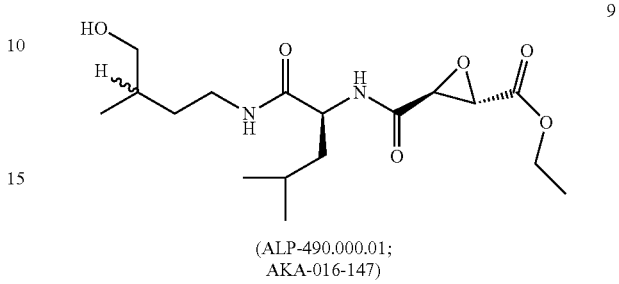

(ALP-490.000.01;
AKA-016-147)

3-[1-(4-Hydroxy-3-methylbutylcarbamoyl)-3-meth-
ylbutylcarbamoyl]-oxirane-2-carboxylic acid ethyl
ester (ALP-490.000.01; AKA-016-147) (9)

To a solution of [1-(4-Hydroxy-3-methylbutylcarbamoyl)-3-methylbutyl]-carbamic acid tert-butyl ester (8) (2.53 g, 8.01 mmol) in MeOH (65 mL) was added p-toluenesulfonic acid hydrate (1.90 g; 10.00 mmol) at rt. The mixture was stirred at 70° C. for 2.5 h. After cooling, the reaction mixture was evaporated to dryness to give a colorless foam. To this material was added (2S, 3S)-3-(ethoxycarbonyl) oxirane-2-carboxylic acid (1.28 g, 8.01 mmol, Peptech) and CH$_2$Cl$_2$ (65 mL) at rt giving a homogeneous solution. The solution was cooled to 0° C. (ice-water bath) under nitrogen. With stirring, 2-(7-azabenzotriazol-1-yl)-1,1,3,3-tetramethyluronium hexafluorophosphate (3.35 g; 8.81 mmol) followed by diisopropylethyl amine (2.87 mL; 16.02 mmol) were added to the reaction solution. The resulting reaction was stirred at 0° C. for one hour and another 4 hours at room temperature. The reaction mixture was diluted with CH$_2$Cl$_2$ (400 ml) and the organics washed with saturated NaHCO$_3$ (2×) and brine (1×). The organic layer was dried over anhydrous Na$_2$SO$_4$, filtered and concentrated to provide a viscous oil. The crude product was purified by silica gel chromatography (elution with 17% to 50% to 80% ethyl acetate/hexanes and 100% ethyl acetate) providing the desired product as a viscous oil (2.32 g, 81%). Recrystallization from ethyl acetate-hexanes (1:1) yielded crystalline material: mp 92-95° C.; TLC R$_f$ 0.50 (EtOAc; PMA stain) $^1$H NMR (CDCl$_3$, 500 MHz) δ 6.96 (d, J=8.6 Hz, 1H), 6.87 (t, J=5.3 Hz, 1H), 4.39-4.40 (m, 1H), 4.22-4.29 (m, 2H), 3.69 (d, J=1.8, 1H), 3.50-3.54 (m, 1H), 3.48 (d, J=1.7 Hz, 1H), 3.40-3.42 (m, 1H), 3.31-3.35 (m, 1H), 3.21-3.23 (m, 1H), 2.74 (t, J=5.2 Hz, 1H), 1.60-1.68 (m, 3H), 1.51-1.54 (m, 2H), 1.38-1.42 (m, 1H), 1.30 (t, J=7.2 Hz, 3H), 0.89-0.92 (m, 9H); $^{13}$C NMR (CDCl$_3$, 125 MHz) δ 171.41, 166.90, 166.38, 67.85, 62.58, 53.99, 53.02, 51.81, 41.42, 37.95 (37.85), 33.85 (33.74), 33.35 (33.33), 25.04, 23.00, 22.29, 17.09 (17.00), 14.21; ESI MS m/z 359.4 [M+H]$^+$; HPLC Purity: 100% t$_R$ 16.2 min (Condition I, UV215 nm)

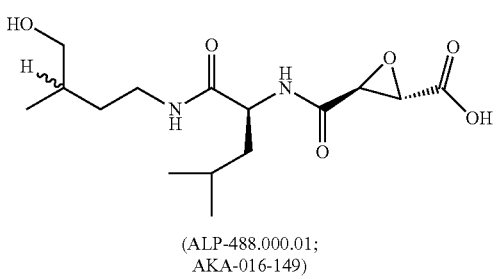

(ALP-488.000.01;
AKA-016-149)

3-[1-(4-Hydroxy-3-methyl-butylcarbamoyl)-3-methyl-butylcarbamoyl]-oxirane-2-carboxylic acid
(ALP-488.000.01; AKA-016-149) (10)

Ethyl ester 9 (215 mg, 0.60 mmol) was dissolved in ethanol (6 mL). The stirred solution was cooled to 0° C. (ice-water bath) and treated with a 1.0 M solution of 85% KOH in ethanol (0.613 mL, 0.61 mmol). The resulting solution was stirred at 0° C. for 60 minutes then warmed to rt and then stirred at rt for 2 hours. The solvent was removed in vacuo and the residue partitioned between water (4 mL) and CH$_2$Cl$_2$ (4 mL). The aqueous layer was acidified to pH 2 with 2 N HCl and extracted with ethyl acetate (4×). The combined organic layers were washed with brine (2×), dried over anhydrous Na$_2$SO$_4$, filtered and concentrated to provide a viscous oil that was dissolved in CH$_3$CN and yielded a colorless foam (103 mg, 52%) after concentration in vacuo: $^1$H NMR (500 MHz, acetone-d$_6$) δ 7.57 (d, J=8.4 Hz, 1H), 7.48 (bs, 1H), 4.45-4.49 (m, 1H), 3.66 (d, J=1.6 Hz, 1H), 3.58 (d, J=1.7 Hz, 1H), 3.37 (d, J=5.7 Hz, 2H), 3.21-3.28 (m, 2H), 1.58-1.67 (m, 5H), 1.29-1.31 (m, 1H), 0.92 (d, J=6.4 Hz, 3H), 0.89 (d, J=6.3 Hz, 6H); $^{13}$C NMR (125 MHz, acetone-d$_6$) δ 172.22 (172.14), 168.91, 166.40 (166.33), 67.75, 54.39 (54.37), 52.73, 52.46 (52.43), 42.56 (42.52), 38.14 (38.02), 34.47, 34.44, 25.57, 23.48, 22.23, 17.21; ESI MS m/z 331.2 (M+H)$^+$.

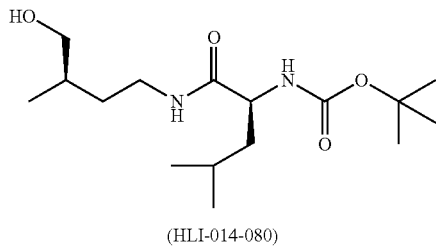

(HLI-014-080)

Compound [1-(4-Hydroxy-3-methylbutylcarbamoyl)-3-methylbutyl]-carbamic acid tert-butyl ester (HLI-014-080) (12)

To a solution of Boc-Leu-OH.H$_2$O (1.27 g, 5.09 mmol) and (R)-4-amino-2-methylbutanol (0.50 g, 4.85 mmol, Ryan Scientific) in CH$_2$Cl$_2$ (25 mL) at 0° C. was added 2-(7-azabenzotriazol-1-yl)-1,1,3,3-tetramethyluronium hexafluorophosphate (2.03 g, 5.33 mmol) followed by diisopropylethyl amine (1.74 mL, 9.70 mmol). The reaction mixture was stirred for 30 minutes at 0° C. and at rt for 1.5 hours under nitrogen. The reaction mixture was diluted with CH$_2$Cl$_2$ (100 mL) and the organics were washed with saturated NaHCO$_3$ (2×), brine (1×), dried over anhydrous Na$_2$SO$_4$, filtered and concentrated. Purification by silica gel chromatography (elution with 10% to 17% to 50% to 60% ethyl acetate/hexanes) gave 12 (1.61 g, 87%, 100%) as a viscous oil: ESI MS m/z 317.4 (M+H)$^+$.

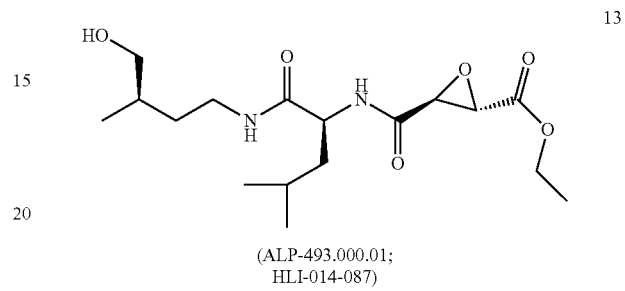

(ALP-493.000.01;
HLI-014-087)

3-[1-(4-Hydroxy-3-methylbutylcarbamoyl)-3-methylbutylcarbamoyl]-oxirane-2-carboxylic acid ethyl ester (ALP-493.000.01; HLI-014-087) (13)

To a solution of 12 (0.90 g, 2.80 mmol) in MeOH (15 mL) was added p-toluenesulfonic acid hydrate (0.676 g, 3.60 mmol) at rt. The reaction mixture was stirred at 65° C. for 1 h. After cooling, the reaction mixture was evaporated to dryness to give a viscous oil. To this material was added (2S, 3S)-3-(ethoxycarbonyl)oxirane-2-carboxylic acid (0.480 g, 2.90 mmol, Peptech) and CH$_2$Cl$_2$ (25 mL) at rt. The solution was cooled to 0° C. With stirring, 2-(7-azabenzotriazol-1-yl)-1,1,3,3-tetramethyluronium hexafluorophosphate (1.17 g, 3.10 mmol) followed by diisopropylethyl amine (1.00 mL, 5.60 mmol) were added to the reaction solution. The resulting reaction was stirred at 5° C. for one hour and another 1 h at room temperature. The reaction mixture was diluted with CH$_2$Cl$_2$ (150 ml) and the organics washed with saturated NaHCO$_3$ (2×) and brine (2×). The organic layer was dried over anhydrous Na$_2$SO$_4$, filtered and concentrated to provide a viscous oil. The crude product was purified by silica gel chromatography (elution with 17% to 25% to 75% to 83% ethyl acetate/hexanes and 100% ethyl acetate) providing the desired product 13 (0.748 g, 73%) as a white solid. Recrystallization from ethyl acetate-ethyl ether-hexanes (1:1:1) yielded crystalline material: mp 106-108° C.; $^1$H NMR (CDCl$_3$, 500 MHz) δ 6.76 (d, J=8.5 Hz, 1H), 6.66 (t, J=5.0 Hz, 1H), 4.35-4.40 (m, 1H), 4.22-4.29 (m, 2H), 3.68 (d, J=1.5 Hz, 1H), 3.52-3.55 (m, 1H), 3.47 (d, J=1.4 Hz, 1H), 3.40-3.45 (m, 1H), 3.37-3.39 (m, 1H), 3.17-3.25 (m, 1H), 2.38 (bs, 1H), 1.60-1.70 (m, 3H), 1.51-1.55 (m, 2H), 1.42-1.47 (m, 1H), 1.31 (t, J=7.2 Hz, 3H), 0.90-0.93 (m, 9H); δ171.27, 166.79, 166.36, 67.96, 62.59, 54.00, 53.11, 51.80, 41.40, 37.89, 33.79, 33.42, 25.07, 23.02, 22.31, 17.06, 14.23; ESI MS m/z 359.4 [M+H]$^+$; HPLC Purity: 99% t$_R$ 16.1 min (Condition I, UV 215 nm).

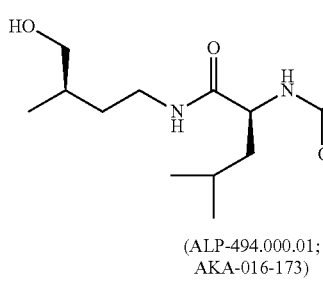

(ALP-494.000.01;
AKA-016-173)

3-[1-(4-Hydroxy-3-methyl-butylcarbamoyl)-3-methyl-butylcarbamoyl]-oxirane-2-carboxylic acid (ALP-494.000.01; AKA-016-173) (14)

Ethyl ester 13 (100 mg, 0.28 mmol) was dissolved in ethanol (3 mL). The stirred solution was cooled to 0° C. (ice-water bath) and treated with a 1.0 M solution of 85% KOH in ethanol (0.285 mL, 0.285 mmol). The resulting solution was stirred at 0° C. for 40 minutes then warmed to rt and then stirred at rt for 20 minutes. The solvent was removed in vacuo and the residue partitioned between water (3 mL) and $CH_2Cl_2$ (4 mL). The aqueous layer was acidified to pH 2 with 2 N HCl and extracted with ethyl acetate (5×). The combined organics were dried over anhydrous $Na_2SO_4$, filtered and concentrated to provide a viscous oil that was dissolved in $CH_3CN$ and after concentration in vacuo yielded 14 as a colorless foam (49 mg, 53%): $^1$H NMR (500 MHz, acetone-$d_6$) δ 7.58 (d, J=8.4 Hz, 1H), 7.49 (app t, 1H), 4.45-4.49 (m, 1H), 3.66 (d, J=1.9 Hz, 1H), 3.58 (d, J=1.7 Hz, 1H), 3.37 (d, J=5.7 Hz, 2H), 3.21-3.28 (m, 2H), 1.58-1.66 (m, 5H), 1.29-1.31 (m, 1H), 0.91 (d, J=6.5 Hz, 3H), 0.89 (d, J=6.2 Hz, 6H); $^{13}$C NMR (125 MHz, acetone-$d_6$) δ 172.15, 168.94, 166.36, 67.70, 54.38, 52.76, 52.37, 42.51, 38.02, 34.42, 34.16, 25.57, 23.48, 22.23, 17.21; ESI MS m/z 331.4 $(M+H)^+$; HPLC Purity: 95% $t_R$=23.7 min, respectively (Condition II, UV 215 nm).

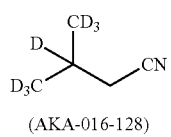

(AKA-016-128)

Compound (AKA-016-128) (16)

To a pressure vial charged with a stirbar was added potassium cyanide (0.508 g, 7.80 mmol) and water (1 mL). Gentle heating was required to dissolve all of the solids. To this solution was added absolute ethanol (3 mL) and 1-bromo-2-methyl-$d_3$-propane-2,3,3,3,-$d_4$ (15) (0.940 g, 6.50 mmol, C/D/N Isotopes). The tube was sealed and heated at 90° C. for 23 h and after an hour a white solid had precipitated from solution. After cooling to rt, water (4 mL) was added to the mixture to dissolve the salts that had formed followed by $CHCl_3$ (2 mL). The organic phase was washed with brine (1×) and concentrated in vacuo carefully giving nitrile 10 (368 mg, 63%) as an oil: $^1$H NMR ($CDCl_3$, 500 MHz) δ 2.16 (s, 2H); $^{13}$C NMR ($CDCl_3$, 125 MHz) δ 119.1, 26.0, 25.2 (t, J=20 Hz), 20.8 (septet, J=19 Hz).

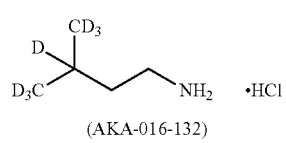

(AKA-016-132)

Compound (AKA-016-132) (17)

To a 1 M $LiAlH_4$ solution (0.775 g, 20.4 mL, 20.4 mmol) stirring at 0° C. (ice-bath) under nitrogen was added a solution of nitrile 16 (0.368 g, 4.08 mmol) dropwise over 15 minutes. After stirring for 1 hour at 0° C., the mixture was warmed to rt and stirring was continued for 19 h. The reaction mixture was quenched at 0° C. with water (0.775 mL), 15% NaOH (aq) (0.775 mL) and water (2.34 mL) giving a heterogeneous mixture. Ethyl ether (10 mL) was added to break up the slurry and the mixture was stirred for 2 h at rt. The solids were removed by filtration over a pad of $Na_2SO_4$ and were rinsed with $Et_2O$ (4×50 mL). The filtrate was cooled to 0° C. and 4 N HCl in dioxane (3 mL, 12.2 mmol) was added dropwise and the reaction mixture was stirred at rt for 30 minutes. The solvent was removed in vacuo to give a clear oil as the crude amine salt. The residue was treated with $CHCl_3$ and xylenes and concentrated in vacuo to yield 17 as a waxy solid, 335 mg (63%): ESI MS m/z 95.4 $(M+H)^+$.

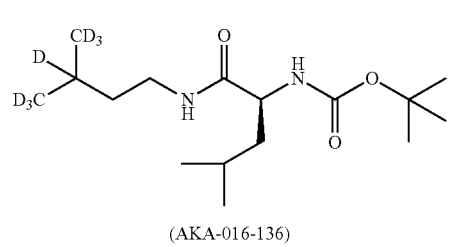

(AKA-016-136)

Compound (AKA-016-136) (18a)

To a solution of Boc-Leu-OH.$H_2O$ (0.573 g, 2.30 mmol) and isoamylamine-$d_7$.HCl (17) (0.335 g, 2.50 mmol) in $CH_2Cl_2$ (20 mL) under nitrogen at room temperature was added 1-hydroxybenzotriazole hydrate (0.459 g, 3.00 mmol), diisopropylethylamine (0.803 mL, 4.60 mmol) and 1-ethyl-3(3-dimethyl aminopropyl)carbodiimide hydrochloride (0.671 g, 3.50 mmol). After stirring for 6 h at rt, the reaction mixture was diluted with $CH_2Cl_2$ (100 mL) and the organics were washed with saturated $NaHCO_3$ (2×), brine (2×), dried over anhydrous $Na_2SO_4$, filtered and concentrated to provide the crude product. Purification by silica gel chromatography (12 g Grace Reveleris column, elution with 10% to 20% ethyl acetate/hexanes) gave compound 18a (0.400 g, 57%) as a waxy, colorless solid: TLC $R_f$ 0.67 (40% EtOAc/hexanes; Ninhydrin stain); $^1$H NMR ($CDCl_3$, 500 MHz) δ 6.16 (bs, 1H), 4.91 (d, J=7.4 Hz, 1H), 4.04 (bs, 2H), 3.22-3.26 (m, 2H), 1.64-1.66 (m, 3H), 1.43-1.51 (m, 11H), 1.34-1.37 (t, J=7.4 Hz, 2H), 0.91-0.94 (m, 6H). $^{13}$C NMR ($CDCl_3$, 125 2 MHz) δ 172.56, 155.99, 62.75, 53.38, 41.46, 38.37, 37.94, 29.90, 28.35, 24.99, 23.10, 22.07; ESI MS m/z 308.4 $(M+H)^+$.

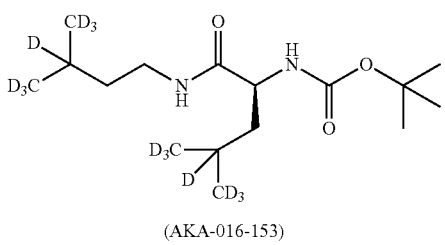

(AKA-016-153)

Compound (AKA-016-153) (18b)

To a solution of L-Leucine-d₇-N-t-Boc.H₂O (0.500 g, 1.95 mmol; C/D/N Isotopes) and isoamylamine-d₇.HCl (17) (0.280 g, 2.15 mmol) in CH₂Cl₂ (20 mL) under nitrogen at room temperature was added 1-hydroxybenzotriazole hydrate (0.389 g, 2.54 mmol), diisopropylethylamine (0.681 mL, 3.90 mmol) and 1-ethyl-3(3-dimethyl aminopropyl) carbodiimide hydrochloride (0.562 g, 2.93 mmol). After stirring for 2.5 h at rt, the reaction mixture was diluted with CH₂Cl₂ (100 mL) and the organics were washed with saturated NaHCO₃ (2×), brine (2×), dried over anhydrous Na₂SO₄, filtered and concentrated to provide the crude product. Purification by silica gel chromatography (20 g SiO2, elution with 10% to 20% to 25% to 30% ethyl acetate/hexanes) gave compound 18b (0.409 g, 67%) as a waxy, colorless solid: TLC R$_f$0.80 (50% EtOAc/hexanes; Ninhydrin stain); ¹H NMR (CDCl₃, 500 MHz) δ 5.16 (bs, 1H), 4.91 (app d, J=6.8 Hz), 4.01-4.05 (m, 1H), 3.24 (q, J=6.5 Hz, 2H), 1.62-1.66 (m, 1H), 1.39-1.46 (m, 9H), 1.36 (t, J=7.4 Hz, 2H); ¹³C NMR (CDCl₃, 125 MHz) δ 172.57, 155.98, 80.19, 53.39, 41.22, 38.36, 37.94, 28.63, 28.52; ESI MS m/z 315.2 (M+H)⁺.

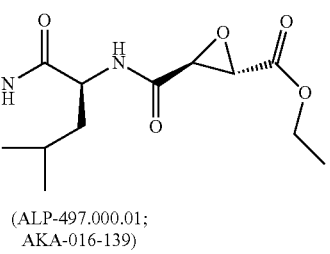

(ALP-497.000.01; AKA-016-139)

Compound (ALP-497.000.01; AKA-016-139) (19a)

To a solution of compound 18a (0.384 g, 1.25 mmol) in MeOH (10 mL) was added p-toluenesulfonic acid hydrate (0.297 g, 1.56 mmol) with stirring. The solution was heated to 70° C. for 2.5 h. After cooling to rt, the reaction was concentrated to provide the crude tosic salt. To this material was added (2S, 3S)-3-(ethoxycarbonyl)oxirane-2-carboxylic acid (0.200 g, 1.25 mmol, Peptech) and CH₂Cl₂ (10 mL) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (0.524 g, 1.38 mmol) followed by diisopropylethylamine (0.448 mL, 2.50 mmol) were added to the reaction solution and the mixture was stirred at 0° C. for 1 h and 3 h at rt. The reaction was diluted with CH₂Cl₂ (70 mL) and the organics were washed with saturated NaHCO₃ (2×) and brine (1×). The organic layer was dried over anhydrous Na₂SO₄, filtered and concentrated in vacuo. The crude product was passed through a silica gel plug eluting with ethyl acetate-hexane (1:9) followed by ethyl acetate-hexane (1:5) and ethyl acetate-hexane (1:1). Concentration of the 1:1 ethyl acetate-hexane elution fractions provided the desire product 19a (340 mg, 78%) as a white solid. Recrystallization from diisopropyl ether-ethanol yielded crystalline material: mp 123-124° C.; ¹H NMR (500 MHz, CDCl₃) δ 6.69 (d, J=8.5 Hz, 1H), 6.10 (bs, 1H), 4.36-4.40 (m, 1H), 4.22-4.28 (m, 2H), 3.67 (s, 1H), 3.46 (s, 1H), 3.19-3.29 (m, 2H), 1.62-1.65 (m, 1H), 1.49-1.53 (m, 2H), 1.37 (t, J=7.5 Hz, 2H), 1.30 (t, J=7.1 Hz, 3H), 0.91 (app t, J=6.9 Hz, 6H); ¹³C NMR (125 MHz, CDCl₃) δ 171.01, 166.71, 166.22, 62.53, 53.99, 53.11, 51.61, 41.46, 38.20, 25.05, 23.00 22.40, 14.23; ESI MS m/z 350.4 (M+H)⁺; HPLC Purity: 100% t$_R$=22 6 min (Condition I, UV 215 nm).

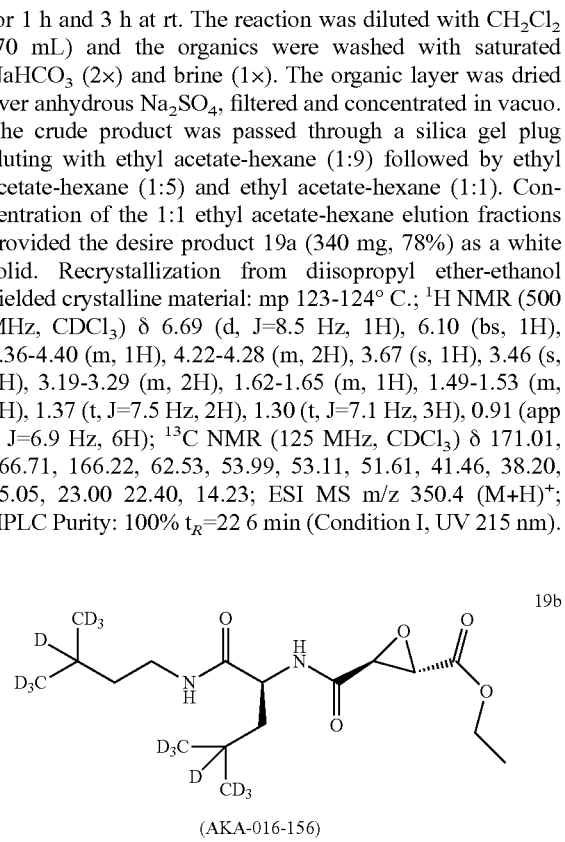

(AKA-016-156)

Compound (ALP-499.000.01; AKA-016-156) (19b)

To a solution of compound 18b (0.389 g, 1.24 mmol) in MeOH (10 mL) was added p-toluenesulfonic acid hydrate (0.281 g, 1.48 mmol) with stirring. The solution was heated to 70° C. for 2.75 h. After cooling to rt, the reaction was concentrated to provide the crude tosic salt. To this material was added (2S, 3S)-3-(ethoxycarbonyl)oxirane-2-carboxylic acid (0.208 g, 1.30 mmol, Peptech) and CH₂Cl₂ (11 mL) to provide a homogeneous solution. The solution was cooled to 0° C. (ice-water bath) under nitrogen. With stirring, 2-(7-azabenzotriazol-1-yl)-1,1,3,3-tetramethyluronium hexafluorophosphate (0.543 g, 1.43 mmol) followed by diisopropylethylamine (0.466 mL, 2.60 mmol) were added to the reaction solution and the mixture was stirred at 0° C. for 1 h and 2.5 h at rt. The reaction was diluted with CH₂Cl₂ (80 mL) and the organics were washed with saturated NaHCO₃ (2×) and brine (1×). The organic layer was dried over anhydrous Na₂SO₄, filtered and concentrated in vacuo. The crude product was passed through a silica gel plug eluting with ethyl acetate-hexane (1:9) followed by ethyl acetate-hexane (1:5) and ethyl acetate-hexane (1:1). Concentration of the 1:1 ethyl acetate-hexane elution fractions provided the desired product 19b (400 mg, 86%) as a white solid. Recrystallization from diisopropyl ether-ethanol yielded crystalline material: mp 121-122° C.; ¹H NMR (500 MHz, CDCl₃) δ 6.72 (d, J=8.7 Hz, 1H), 6.15 (t, J=5.4 Hz, 1H), 4.36-4.40 (m, 1H), 4.22-4.28 (m, 2H), 3.67 (d, J=1.7 Hz, 1H), 3.46 (d, J=1.8 Hz, 1H), 3.18-3.30 (m, 2H), 1.60-1.64 (m, 1H), 1.49-1.53 (m, 1H), 1.37 (t, J=7.5 Hz, 2H), 1.30 (t, J=7.1 Hz, 3H); ¹³C NMR (125 MHz, CDCl₃) δ 171.04, 166.72, 166.22, 62.53, 53.99, 53.10, 51.62, 41.24, 25.25 (m, weak), 24.12 (m, weak), 21.61 (m, weak), 21.44 (m, weak), 38.22, 14.23; ESI MS m/z 357.2 (M+H)+; Anal. ($C_{17}H_{18}D_{14}N_2O_5$) C, H, N; HPLC Purity: 99% $t_R$=22.2 min (Condition I, UV 215 nm).

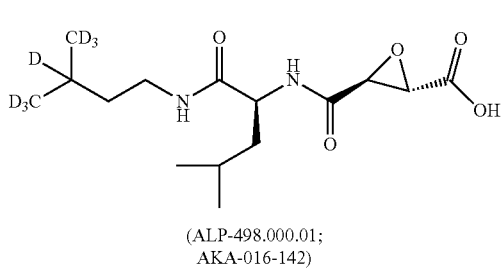

(ALP-498.000.01; AKA-016-142)

Compound (ALP-498.000.01; AKA-016-142) (20a)

Ethyl ester 19a (117 mg, 0.334 mmol) was dissolved in ethanol (3 mL). The stirred solution was cooled to 0° C. (ice-water bath) and treated with a 1.0 M solution of 85% KOH in ethanol (0.34 mL, 0.34 mmol). The resulting solution was stirred at 0° C. for 1 h and after warming to rt was concentrated in vacuo. The residue was partitioned between water (2 mL) and $CH_2Cl_2$ (2 mL). The layers were separated and the aqueous portion was extracted once more with $CH_2Cl_2$. The aqueous layer was acidified to pH 2 with 2 N HCl and extracted with ethyl acetate (3×). The combined organic layers were dried over anhydrous $Na_2SO_4$, filtered and concentrated to provide an oil (94 mg, 88%). Recrystallization from hexanes-ethyl acetate (1:1) yielded 20a as colorless crystals: mp=150-151° C.; $^1$H NMR (500 MHz, acetone-$d_6$) δ 7.52 (d, J=8.4 Hz, 1H), 7.41 (bs, 1H), 4.44-4.49 (m, 1H), 3.66 (d, J=1.8 Hz, 1H), 3.57 (d, J=1.8 Hz, 1H), 3.17-3.24 (m, 2H), 1.57-1.68 (m, 3H), 1.35 (t, J=7.3 Hz, 2H), 0.91 (dd, J=6.4, 11.0 Hz, 6H); $^{13}$C NMR (125 MHz, acetone-$d_6$) δ 172.05, 168.85, 166.26, 54.37, 52.72, 52.30 (m), 42.64 (m), 39.07, 38.11 (m), 25.57, 23.47, 22.25; ESI MS m/z 322.2 (M+H)+; HPLC Purity: 95% $t_R$=18.0 min (Condition I, UV 215 nm).

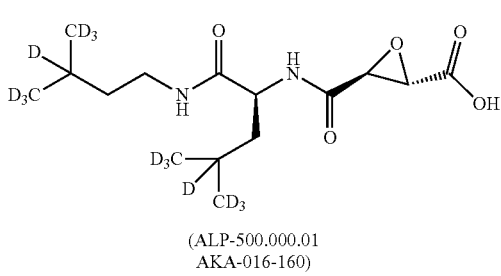

(ALP-500.000.01 AKA-016-160)

Compound (ALP-500.000.01; AKA-016-160) (20b)

Ethyl ester 19b (94 mg, 0.264 mmol) was dissolved in ethanol (3 mL). The stirred solution was cooled to 0° C. (ice-water bath) and treated with a 1.0 M solution of 85% KOH in ethanol (0.269 mL, 0.269 mmol). The resulting solution was stirred at 0° C. for 0.5 h and after warming to rt was concentrated in vacuo. The residue was partitioned between water (4 mL) and $CH_2Cl_2$. The layers were separated and the aqueous layer was acidified to pH 2 with 2 N HCl and extracted with ethyl acetate (3×). The combined organic layers were washed with brine and dried over anhydrous $Na_2SO_4$, filtered and concentrated to provide a white solid (78 mg, 90%). Recrystallization from hexanes-ethyl acetate (1:1) yielded 20b as colorless crystals: mp=150-151° C.; $^1$H NMR (500 MHz, acetone-$d_6$) δ 4.44-4.47 (m, 1H), 3.66 (d, J=1.9 Hz, 1H), 3.57 (d, J=1.9 Hz, 1H), 3.15-3.25 (m, 2H), 1.57-1.59 (m, 2H), 1.35 (t, J=7.3 Hz, 2H); $^{13}$C NMR (125 MHz, acetone-$d_6$) δ 172.09, 168.92, 166.26, 54.37, 52.77, 52.28, 42.38, 39.07, 38.11; ESI MS m/z 329.4 (M+H)+; Anal. ($C_{15}H_{12}D_{14}N_2O_5$) C, H, N; HPLC Purity: 99% $t_R$=18.0 min (Condition I, UV 215 nm).

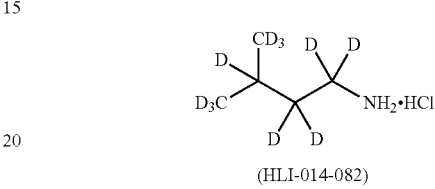

(HLI-014-082)

Compound (HLI-014-082) (22)

To a mixture of sodium azide (455 mg, 7.0 mmol), 4-pentanoic acid-$d_{11}$ (255 mg, 2.0 mmol, C/D/N Isotopes), n-butylammonium bromide (96 mg, 0.3 mmol) and zinc triflate (24 mg, 0.06 mmol) in a 30-mL pressure vial was added THF (20 mL). To the vial heated to 40° C. with stirring was added (Boc)$_2$O (480 mg, 2.2 mmol) in one portion. The vial was sealed and stirred at 50° C. for 2 hours. After the reaction mixture was cooled, it was poured into 10% NaNO$_2$ (aq) (40 mL). Then ethyl acetate (50 mL) was added and the mixture was stirred at rt for 20 minutes. The aqueous layer was separated and extracted with ethyl acetate (3×). The combined organic layers were washed with saturated NH$_4$Cl$_1$ (1×), saturated NaHCO$_3$ (1×), brine (1×) and dried over Na$_2$SO$_4$, filtered and concentrated to give an oily residue of an intermediate product. The residue was dissolved in THF (10 mL) and heated at 85° C. for 2 hours. The temperature was lowered to 46° C. and 1 N HCl (1 mL) was added to the mixture which was stirred for 6 h. The reaction mixture was cooled to rt and conc. HCl (0.5 mL) was added and stirring was continued for 3 days. The solvent was removed in vacuo and the aqueous phase was extracted with Et$_2$O (2×). The aqueous phase was basified with 1 N NaOH to pH=12 and extracted with Et$_2$O (3×). The combined organics were dried over MgSO$_4$ and filtered. The filtrate was treated with 4 N HCl/dioxane (0.8 mL) and a white solid formed immediately. After concentration, the crude amine HCl salt was isolated as a colorless, amorphous solid (111 mg, 41%): ESI MS m/z 99.2 (M+H)+.

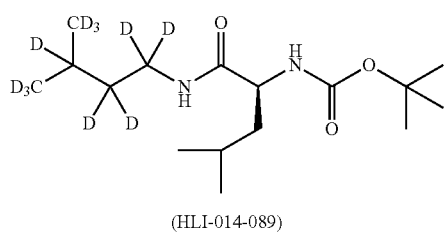

(HLI-014-089)

Compound (HLI-014-089) (23)

To a solution of Boc-Leu-OH.H₂O (226 mg, 0.90 mmol), isoamylamine-d₁₁ HCl (22) (111 mg, 0.82 mmol) and 1-hydroxybenzotriazole hydrate (163 mg, 1.07 mmol), in CH₂Cl₂ (8 mL) under nitrogen at room temperature was added 1-ethyl-3(3-dimethyl aminopropyl)carbodiimide hydrochloride (236 mg, 1.23 mmol) followed by the addition of diisopropylethylamine (0.294 mL, 1.64 mmol). After stirring for 49 h at rt, the reaction mixture was diluted with CH₂Cl₂ (100 mL) and the organics were washed with saturated NaHCO₃ (2×), brine (2×), dried over anhydrous Na₂SO₄, filtered and concentrated to provide an oil (374 mg). Purification by silica gel chromatography (elution with 10% to 20% to 30% ethyl acetate/hexanes) gave amide 23 (124 mg, 49%) as a waxy, white solid: TLC $R_f$ 0.25 (20% EtOAc/hexanes; phosphomolybdic stain); ¹H NMR CDCl₃, 500 MHz) δ6.03 (bs, 1H), 4.86 (bs, 1H), (m, 1H), 4.01-4.05 (m, 1H), 1.57-1.69 (m, 3H), 1.44 (s, 9H), 0.92-0.99 (m, 6H); ESI MS m/z 312.4 (M+H)⁺.

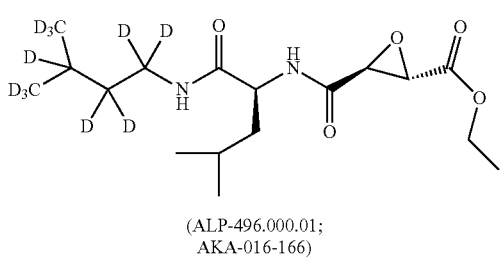

(ALP-496.000.01;
AKA-016-166)

Compound (ALP-496.000.01; AKA-016-166) (24)

To a solution of compound 23 (121 mg, 0.389 mmol) in MeOH (3 mL) was added p-toluenesulfonic acid hydrate (89 mg, 0.467 mmol) with stirring. The solution was heated to 70° C. for 3 h. After cooling to rt, the reaction was concentrated to provide the crude tosic salt. To this material was added (2S, 3S)-3-(ethoxycarbonyl)oxirane-2-carboxylic acid (62 mg, 0.389 mmol; Peptech) and CH₂Cl₂ (4 mL). The solution was cooled to 0° C. (ice-water bath) under nitrogen. With stirring, 2-(7-azabenzotriazol-1-yl)-1,1,3,3-tetramethyluronium hexafluorophosphate (163 mg, 0.428 mmol) followed by diisopropylethylamine (0.140 mL, 0.778 mmol) were added to the reaction solution and the mixture was stirred at 0° C. for 1.25 h and 30 minutes at rt. The reaction was diluted with CH₂Cl₂ (50 mL) and the organics were washed with saturated NaHCO₃ (2×) and brine (1×). The organic layer was dried over anhydrous Na₂SO₄, filtered and concentrated in vacuo. The crude product was purified by silica gel chromatography eluting with 10% to 17% to 50% ethyl acetate/hexanes and provided the desired product 24 (110 mg, 80%) as a white solid. Recrystallization from ethyl acetate-hexanes (1:1) yielded crystalline material: mp 123-124° C.; ¹H NMR (500 MHz, CDCl₃) δ 6.53 (d, J=8.6 Hz, 1H), 5.87 (bs, 1H), 4.34-4.38 (m, 1H), 4.23-4.30 (m, 2H), 3.67 (d, J=1.7 Hz, 1H), 3.46 (d, J=1.9 Hz, 1H), 1.62-1.66 (m, 1H), 1.49-1.55 (m, 2H), 1.32 (t, J=7.0 Hz, 3H), 0.92 (t, J=6.5 Hz, 6H); ¹³C NMR (125 MHz, CDCl₃) δ 170.94, 166.64, 166.25, 62.57, 54.03, 53.21, 51.59, 41.43, 25.08, 23.03, 22.40, 14.26; ESI MS m/z 354.4 (M+H)⁺; HPLC Purity: 100% $t_R$=22.6 min (Condition I, UV 215 nm).

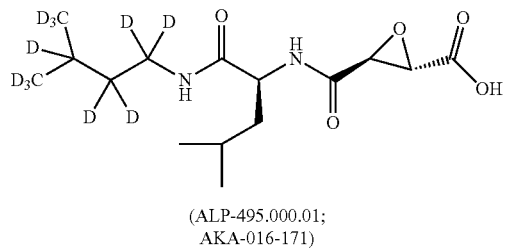

(ALP-495.000.01;
AKA-016-171)

Compound (ALP-495.000.01; AKA-016-171) (25)

Ethyl ester 24 (48 mg, 0.135 mmol) was dissolved in ethanol (2 mL). The stirred solution was cooled to 0° C. (ice-water bath) and treated with a 1.0 M solution of 85% KOH in ethanol (0.137 mL, 0.137 mmol). The resulting solution was stirred at 0° C. for 0.5 h and then slowly warmed to rt and stirred for an additional 1.5 h. The solvent was removed in vacuo and the residue was partitioned between water (4 mL) and CH₂Cl₂ (2 mL). The layers were separated and the aqueous layer was acidified to pH 2 with 2 N HCl and extracted with ethyl acetate (3×10 mL). The combined organic layers were washed with brine and dried over anhydrous Na₂SO₄, filtered and concentrated to provide a white solid (30 mg, 69%). Recrystallization from hexanes-ethyl acetate (1:1) yielded 25 as colorless crystals: mp=152-153° C.; ¹H NMR (500 MHz, acetone-d₆) δ 4.44-4.47 (m, 1H), 3.63 (d, J=1.9 Hz, 1H), 3.55 (d, J=1.8 Hz, 1H), 1.61-1.66 (m, 1H), 1.56-1.59 (m, 2H), 0.85-92 (m, 6H); ¹³C NMR (125 MHz, acetone-d₆) δ 171.98, 169.06, 166.36, 54.37, 52.99, 52.26, 42.64, 25.58, 23.49, 22.27; ESI MS m/z 326.4 (M+H)⁺; HPLC Purity: 100% $t_R$=18.3 min (Condition I, UV 215 nm).

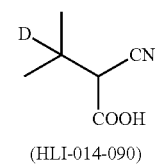

(HLI-014-090)

Compound (HLI-014-090) (27)

To a mixture of 2-iodopropane-2 di (2.25 g, 13.2 mmol; C/D/N Isotopes) and ethyl cyanoacetate (1.50 g, 13.2 mmol) in a pressure vial was added CH₃CN (6 mL) and potassium carbonate (3.64 g, 26.4 mmol). The vial was sealed and the mixture was stirred at rt for 52 hours. The reaction mixture was heated to 65° C. and stirred for 48 h. After cooling, the potassium carbonate was removed by filtration and the solids were rinsed with CH₃CN (20 mL). The filtrate was concentrated in vacuo to give the cyanoester as a yellow oil (2.1 g, quantitative yield) which was used in the following step without further purification. To a solution of the crude ester dissolved in a mixture THF (25 mL) and water (8 mL) was added LiOH.H₂O (1.1 g, 26.8 mmol) at rt with stirring. The reaction mixture was stirred for 71 hours. Then the solvent was removed in vacuo and the remaining aqueous solution was diluted with water (10 mL) and extracted with ethyl ether (2×). The aqueous layer was then acidified with 1 N HCl to pH=1 and extracted with ethyl ether (3×). The combined organic layers were dried over MgSO$_4$, filtered and concentrated to give 27 (1.33 g, 78%) as a viscous yellow oil. $^1$H NMR (500 MHz, CDCl$_3$) δ 9.61 (bs, 1H), 3.47 (d, J=8.5 Hz, 1H), 2.41-2.47 (m, 1H), 1.17 (d, J=6.8 Hz, 3H), 1.30 (d, J=6.7 Hz, 3H).

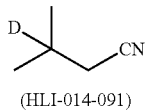

(HLI-014-091)

Compound (HLI-014-091) (28)

Acid 27 (1.32 g, 10.3 mmol) and copper powder (150 mg, 2.4 mmol) were placed into a pressure vial and after it was sealed with a septum was heated to 200° C. with stirring. The decarboxylation occurred immediately and the nitrile was distilled via a canula needle into an empty tube sealed with a septum. Nitrile 28 (0.88 g, 100%) was obtained as a clear oil. $^1$H NMR (CDCl$_3$, 500 MHz) δ 2.23 (s, 2H), 1.06 (s, 6H); $^{13}$C NMR (125 MHz, CDCl$_3$) δ 119.0, 26.2, 21.8.

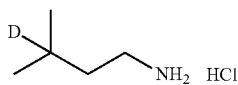

(AKA-016-168)

Compound (AKA-016-168) (29)

To a 1.0 M LiAlH$_4$ solution (29.9 mL, 29.9 mmol) in THF at 0° C. under N$_2$ was added dropwise a solution of nitrile 28 (0.503 g, 5.98 mmol) in THF (20 mL) over 15 minutes. After an hour, the ice-bath was removed and stirring was continued at rt for 22 h. The reaction mixture was cooled to 0° C. and carefully quenched with water (1.13 mL); then 15% NaOH (aq) (1.13. mL) was added followed by the addition of water (3.39 mL). Some Et$_2$O was added to break-up the slurry and the mixture was stirred for 2 h at rt. The solids were removed by filtration and rinsed with Et$_2$O (4×50 mL). The filtrate was cooled to 0° C. and 4 N HCl/dioxane (4.5 mL, 17.94 mmol) was added dropwise. After stirring at 0° C. for 30 minutes, the solvent was removed in vacuo. The residue was treated with CH$_2$Cl$_2$ and xylenes and concentrated in vacuo to give 29 as a light-colored waxy solid (quantitative): ESI MS m/z 89.0 (M+H)$^+$.

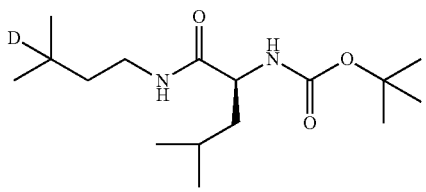

(AKA-016-169)

Compound (AKA-016-169) (30)

To a solution of Boc-Leu-OH.H$_2$O (1.35 g, 5.44 mmol) and amine salt (29) (0.742 g, 5.98 mmol) in CH$_2$Cl$_2$ (50 mL) under nitrogen at room temperature was added 1-hydroxy-benzotriazole hydrate (1.08 g, 7.07 mmol), diisopropylethylamine (1.90 mL, 10.9 mmol) and 1-ethyl-3(3-dimethylaminopropyl)-carbodiimide hydrochloride (1.56 g, 8.16 mmol). After stirring for 3 h at rt, the reaction mixture was diluted with CH$_2$Cl$_2$ (200 mL) and the organics were washed with saturated NaHCO$_3$ (2×), brine (2×), dried over anhydrous Na$_2$SO$_4$, filtered and concentrated to provide the crude product. Purification by silica gel chromatography (50 g SiO$_2$, elution with 10% to 15% to 20% to 30% ethyl acetate/hexanes) gave compound 30 (0.992 g, 60%) as a waxy, colorless solid: TLC R$_f$ 0.45 (40% EtOAc/hexanes; Ninhydrin stain); $^1$H NMR (CDCl$_3$, 500 MHz) δ 6.16 (bs, 1H), 4.91 (d, J=7.7 Hz, 1H), 4.04-4.08 (m, 1H), 3.24 (q, J=6.4 Hz, 2H), 1.63-1.68 (m, 2H), 1.43 (s, 9H), 1.35-1.38 (t, J=7.4 Hz, 2H), 0.91-0.96 (m, 7H), 0.88 (s, 6H); ESI MS m/z 302.4 (M+H)$^+$.

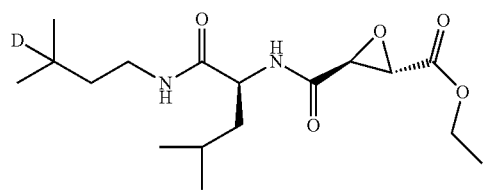

(ALP-###.000.01; HLI-014-093)

Compound (HLI-014-093) (31)

To a solution of compound 30 (0.98 g, 3.25 mmol) in MeOH (15 mL) was added p-toluenesulfonic acid hydrate (0.772 g, 4.06 mmol) with stirring. The solution was heated to 70° C. for 1 h. After cooling to rt, the reaction was concentrated to provide the crude tosic salt. To this material was added (2S, 3S)-3-(ethoxycarbonyl)oxirane-2-carboxylic acid (0.520 g, 3.25 mmol, Peptech) and CH$_2$Cl$_2$ (20 mL). The solution was cooled to 5° C. (dry ice-water bath) under nitrogen. With stirring, 2-(7-azabenzotriazol-1-yl)-1,1,3,3-tetramethyluronium hexafluorophosphate (1.36 g, 3.58 mmol) followed by diisopropylethylamine (1.16 mL, 6.50 mmol) were added to the reaction solution and the mixture was stirred at 5° C. for 1 h and 1 h at rt. The reaction mixture was diluted with CH$_2$Cl$_2$ (150 mL) and the organics were washed with saturated NaHCO$_3$ (2×) and brine (1×). The organic layer was dried over anhydrous Na$_2$SO$_4$, filtered and concentrated in vacuo. The crude product was passed through a silica gel plug eluting with ethyl acetate-hexane (1:9) followed by ethyl acetate-hexane (1:5), ethyl acetate-hexane (1:3) and ethyl acetate-hexane (1:1). Concentration of the 1:1 and 1:3 ethyl acetate-hexane elution fractions provided the desired product 31 (0.98 g, 88%) as a white solid. Recrystallization from diisopropyl ether-ethanol yielded crystalline material: $^1$H NMR (500 MHz, CDCl$_3$) δ 6.85 (d, J=8.7 Hz, 1H), 6.29 (t, J=5.4 Hz, 1H), 4.40-4.43 (m, 1H), 4.21-4.28 (m, 2H), 3.67 (d, J=1.6 Hz, 1H), 3.46 (d, J=1.7 Hz, 1H), 3.17-3.28 (m, 2H), 1.60-1.64 (m, 1H), 1.50-1.55 (m, 2H), 1.37 (t, J=7.5 Hz, 2H), 1.30 (t, J=7.1 Hz, 3H), 0.88-0.92 (m, 12H); $^{13}$C NMR (125 MHz, CDCl$_3$) δ

171.09, 166.76, 166.21, 62.49, 53.96, 53.04, 51.65, 41.50, 38.35, 38.16, 25.57 (t, J=19.1 H), 25.03, 22.98, 22.43, 22.41, 14.21; ESI MS m/z 344.2 (M+H)+.

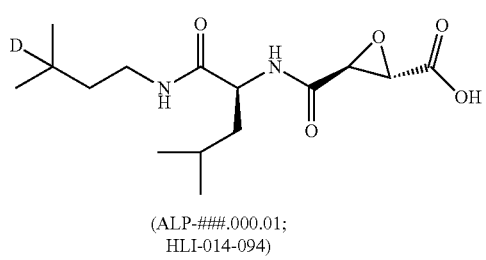

Compound (HLI-014-094) (32)

Ethyl ester 31 (171 mg, 0.5 mmol) was dissolved in ethanol (6 mL). The stirred solution was treated with a 0.65 M solution of 85% KOH in ethanol (0.77 mL, 0.5 mmol). The resulting solution was stirred at rt for an hour. After concentrating in vacuo, the residue was partitioned between water (10 mL) and ethyl ether. The layers were separated and the aqueous layer was extracted with ethyl ether (2×) then acidified to pH 2 with 1 N HCl and extracted with ethyl acetate (3×). The combined organic layers were dried over anhydrous Na$_2$SO$_4$, filtered and concentrated to provide a white solid that was recrystallized from hexanes-ethyl acetate (1:2) to yield 32 (30 mg, 19%) as colorless crystals; $^1$H NMR (500 MHz, acetone-d$_6$) δ 7.59 (d, J=8.4 Hz, 1H), 7.46 (bs, 1H), 4.46-4.50 (m, 1H), 3.66 (d, J=1.7 Hz), 3.58 (d, J=1.7 Hz, 1H), 3.18-3.25 (m, 2H), 1.63-1.67 (m, 1H), 1.59 (t, J=6.8 Hz, 2H), 1.36 (t, J=7.3 Hz, 2H), 0.95 (d, J=6.6 Hz, 3H), 0.92 (d, J=5.1 Hz, 3H), 0.88 (s, 6H); $^{13}$C NMR (125 MHz, acetone-d$_6$) δ 172.18, 168.95, 166.30, 54.36, 52.75, 52.30, 42.59, 39.17, 38.14, 25.99 (weak t, J=19.1 Hz), 25.57, 23.46, 22.71, 22.26; ESI MS m/z 316.4 (M+H)+; HPLC Purity: 96% t$_R$=17.2 min (Condition I, UV 215 nm).

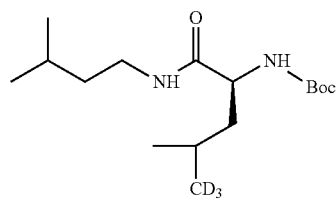

Compound (HLI-014-045) (34)

N-(tert-butyloxycarbonyl)-L-leucine-d$_3$ (methyl-d$_3$) hydrate (33) (250 mg, 0.99 mmol, C/D/N Isotopes), 1-hydroxybenzotriazole hydrate (197 mg, 1.29 mmol), and isoamylamine (95 mg, 1.09 mmol) were dissolved in CH$_2$Cl$_2$ (10 mL) at room temperature under nitrogen. With stirring, 1-ethyl-3-(3-dimethylaminopropyl)carbodiimide hydrochloride (288 mg, 1.50 mmol) was added. After stirring for three hours at room temperature, the reaction was diluted with CH$_2$Cl$_2$ (80 mL) and extracted with saturated NaHCO$_3$ (2×) and brine (1×). The organic layer was dried over anhydrous Na$_2$SO$_4$, filtered and concentrated to provide 313 mg of compound 34 as a waxy solid: ESI MS m/z 304.2 (M+H)+.

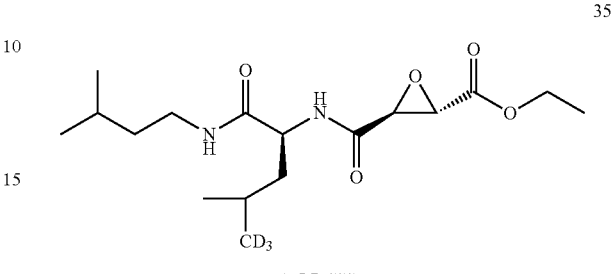

Compound (ALP-###; HLI-014-053) (35)

Compound 34 was dissolved in methanol (5 mL) and then treated with p-toluenesulfonic acid hydrate (237 mg, 1.25 mmol) with stirring. The solution was heated to 70° C. for four hours. After cooling, the reaction was evaporated to dryness and the residue treated with ether and hexanes. Removal of the volatiles provided the tosic salt as a white foam: ESI MS m/z 204.2 (C$_{11}$H$_{22}$D$_3$N$_2$O)+. To this material was added (2S, 3S)-3-(ethoxycarbonyl)oxirane-2-carboxylic acid (160 mg, 1.0 mmol, Peptech) and CH$_2$Cl$_2$ (10 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluoro-phosphate (418 mg, 1.1 mmol) followed by diisopropylethylamine (358 μL, 2.0 mmol) were added to the reaction solution. The resulting reaction was stirred at 0° C. for one hour and another hour at room temperature. The reaction was diluted with CH$_2$Cl$_2$ (100 ml) and extracted with saturated NaHCO$_3$ (2×) and brine (1×). The organic layer was dried over anhydrous Na$_2$SO$_4$, filtered and concentrated to provide 35 a yellow solid. The crude product was filtered through a silica gel plug eluting with ethyl acetate-hexane (1:9) followed by ethyl acetate-hexane (1:1). Concentration of the 1:1 ethyl acetate-hexane elution fractions provided the title compound 35 as a white solid (295 mg, 0.86 mmol, 86%). Recrystallization from diisopropyl ether-ethanol yielded crystalline material: mp 122-123° C.; $^1$H NMR (CDCl$_3$, 500 MHz) δ 6.71 (d, J=8.6 Hz, 1H), 6.12-6.14 (m, 1H), 4.36-4.41 (m, 1H), 4.21-4.29 (m, 2H), 3.67 (d, J=1.4 Hz, 1H), 3.46 (d, J=1.7 Hz, 1H), 3.20-3.28 (m, 2H), 1.56-1.64 (m, 2H), 1.50-1.55 (m, 2H), 1.38 (q, J=7.0 Hz, 2H), 1.30 (t, J=7.0 Hz, 3H), 0.89-0.92 (m, 9H); $^{13}$C NMR (CDCl$_3$, 125 MHz) δ 171.02, 166.71, 166.22, 62.53, 53.99, 53.11, 51.62, 41.41, 38.49, 38.21, 26.06, 24.81, 22.92, 22.62, 22.58, 22.32, 14.24; ESI MS m/z 346.2 (M+H)+; Anal. (C$_{17}$H$_{27}$D$_3$N$_2$O$_5$) C, H, N; HPLC purity: 99.7%. t$_R$=22.8 min (Condition I, UV 215 nm).

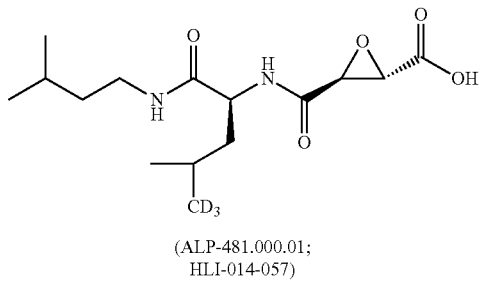

(ALP-481.000.01;
HLI-014-057)

Compound (2S,3S)-3-((S)-1-(Isopentylamino)-4-methyl-d$_3$-1-oxopentan-2-ylcarbamoyl)oxirane-2-carboxylic acid (ALP-481.000.01; HLI-014-057) (36)

The ethyl ester 35 from the above preparation (35 mg, 0.1 mmol) was dissolved in ethanol (2.0 mL). The stirred solution was cooled to 0° C. (ice-water bath) and treated with a solution of 85% KOH in ethanol (70 µL, 0.11 mmol). The resulting solution was stirred at 0° C. for 20 minutes and at room temperature for 10 minutes. The reaction was concentrated to dryness and the residue partitioned between water and ethyl acetate. The organic layer was separated and the aqueous extracted once more with ethyl acetate. The aqueous layer was acidified to pH 2 with 1 N HCl and extracted with ethyl acetate (3×). The combined organic layers were dried over anhydrous Na$_2$SO$_4$, filtered and concentrated to provide 36 as a white solid (36 mg, 96%). Recrystallization from ethyl acetate-hexanes yielded acid 36 as a colorless crystal: mp 152-153° C.; $^1$H NMR (acetone-d$_6$, 500 MHz) δ7.60 (d, J=8.5 Hz, 1H), 7.49 (br s, 1H), 4.48 (q, J=7.5 Hz, 1H), 3.66 (d, J=1.6 Hz, 1H), 3.58 (d, J=1.8 Hz, 1H), 3.17-3.26 (m, 2H), 1.57-1.66 (m, 4H), 1.37 (q, J=7.2 Hz, 2H), 0.91 (d, J=6.3 Hz, 3H), 0.88 (d, J=6.7 Hz, 6H); $^{13}$C NMR (acetone-d$_6$, 125 MHz) δ172.36, 168.99, 166.37, 54.37, 52.71, 52.41, 52.37 (weak), 52.33 (weak), 42.54, 39.27, 38.29, 38.17, 26.45, 25.32, 23.37, 22.84, 22.82, 22.18; ESI MS m/z 318.2 (M+H)$^+$; HPLC purity: 99.5%. $t_R$=18.0 min (Condition I, UV 215 nm).

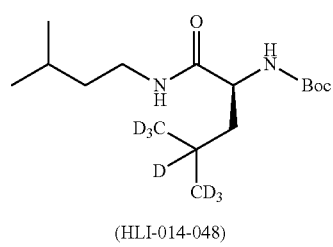

(HLI-014-048)

Compound (HLI-014-048) (38)

N-(tert-butyloxycarbonyl)-L-leucine-d$_7$ (isopropyl-d$_7$) hydrate (37) (250 mg, 0.98 mmol, C/D/N Isotopes), 1-hydroxybenzotriazole hydrate (195 mg, 1.27 mmol) and isoamylamine (94 mg, 1.07 mmol) were dissolved in CH$_2$Cl$_2$ (10 mL) at room temperature under nitrogen. With stirring, 1-ethyl-3-(3-dimethylaminopropyl)carbodiimide hydrochloride (282 mg, 1.47 mmol) was added. After stirring for three hours at room temperature, the reaction was diluted with CH$_2$Cl$_2$ (80 mL) and extracted with saturated NaHCO$_3$ (2×) and brine (1×). The organic layer was dried over anhydrous Na$_2$SO$_4$, filtered and concentrated to provide 315 mg of 38 as a white semi-solid: ESI MS m/z 308.4 (M+H)$^+$.

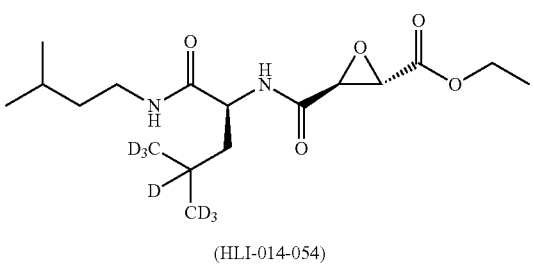

(HLI-014-054)

Compound (HLI-014-054) (39)

Compound 38 was dissolved in methanol (5 mL) and p-toluenesulfonic acid hydrate (237 mg, 1.25 mmol) was added with stirring. The solution was heated to 70° C. for four hours. After cooling, the reaction was evaporated to dryness and the residue treated with diethyl ether and hexanes. Removal of the volatiles provided the tosic salt as a white foam: ESI MS m/z 208.0 (C$_{11}$H$_{18}$D$_7$N$_2$O$^+$). To this material was added (2S, 3S)-3-(ethoxycarbonyl)oxirane-2-carboxylic acid (160 mg, 1.00 mmol, Peptech) and CH$_2$Cl$_2$ (10 ml) to provide a homogeneous solution. The solution was cooled to 0° C. (ice-water bath) under nitrogen. With stirring, 2-(7-azabenzotriazol-1-yl)-1,1,3,3-tetramethyluronium hexafluoro-phosphate (418 mg, 1.1 mmol) followed by diisopropylethylamine (358 µL, 2.0 mmol) were added to the reaction solution. The resulting reaction was stirred at 0° C. for one hour and another hour at room temperature. The reaction was diluted with CH$_2$Cl$_2$ (100 ml) and extracted with saturated NaHCO$_3$ (2×) and brine (1×). The organic layer was dried over anhydrous Na$_2$SO$_4$, filtered and concentrated to provide product 39 as a yellow solid. The crude product was filtered through a silica gel plug eluting with ethyl acetate-hexane (1:9) followed by ethyl acetate-hexane (1:1). Concentration of the 1:1 ethyl acetate-hexane elution fractions provided the desired product 39 as a white solid (314 mg; 0.9 mmol; 90%). Recrystallization from diisopropyl ether-ethanol yielded crystalline material: mp 122-123° C.; $^1$H NMR (CDCl$_3$, 500 MHz) δ 6.68 (d, J=8.6 Hz, 1H), 6.08-6.10 (m, 1H), 4.35-4.40 (m, 1H), 4.21-4.29 (m, 2H), 3.67 (d, J=1.8 Hz, 1H), 3.45 (d, J=1.7 Hz, 1H), 3.20-3.30 (m, 2H), 1.56-1.65 (m, 2H), 1.48-1.52 (m, 1H), 1.38 (q, J=7.3 Hz, 2H), 1.31 (t, J=7.2 Hz, 3H), 0.89-0.91 (d, J=6.6 Hz, 6H); $^{13}$C NMR (CDCl$_3$, 125 MHz) δ 171.02, 166.70, 166.22, 62.54, 53.99, 53.11, 51.61, 41.23, 38.49, 38.21, 28.51 (weak), 26.06, 24.11 (m, weak), 22.62, 22.58, 14.24; ESI MS m/z 350.4 (M+H)$^+$; HPLC purity: 99.7%. $t_R$=22 5 min (Condition I, UV 215 nm).

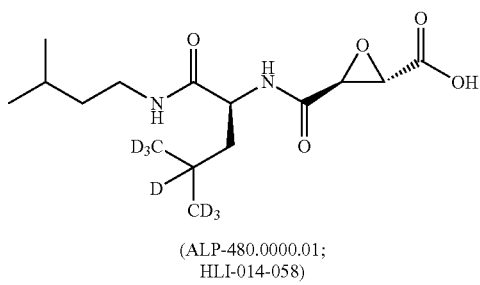

(ALP-480.0000.01; HLI-014-058)

Compound (2S,3S)-3-((S)-4,5,5,5-d$_4$-1-(isopentylamino)-1-oxo-4-(methyl-d$_3$)pentan-2-ylcarbamoyl)oxirane-2-carboxylic acid (ALP-480.000.01; HLI-014-058) (40)

The ethyl ester 39 from the above preparation (36 mg, 0.1 mmol) was dissolved in ethanol (2 mL). The stirred solution was cooled to 0° C. (ice-water bath) and treated with a solution of 85% KOH in ethanol (70 µL, 0.11 mmol). The resulting solution was stirred at 0° C. for 20 minutes and at room temperature for 10 minutes. The reaction was concentrated to dryness and the residue partitioned between water and ethyl acetate. The layers were separated and the aqueous extracted once more with ethyl acetate. The aqueous layer was acidified to pH 2 with 1 N HCl and extracted with ethyl acetate (3×). The combined organic layers were dried over anhydrous Na$_2$SO$_4$, filtered and concentrated to provide 40 as an off-white powder (32 mg, 97%). Recrystallization from ethyl acetate-hexanes yielded acid 40 as a colorless crystal: mp 153° C.; $^1$H NMR (acetone-d$_6$, 500 MHz) δ 7.61 (d, J=8.3 Hz, 1H), 7.49 (br s, 1H), 4.48 (q, J=7.5 Hz, 1H), 3.66 (d, J=1.0 Hz, 1H), 3.58 (s, 1H), 3.17-3.26 (m, 2H), 1.57-1.66 (m, 3H), 1.37 (q, J=7.2 Hz, 2H), 0.88 (d, J=6.6 Hz, 6H); $^{13}$C NMR (acetone-d$_6$, 125 MHz) δ172.32, 168.99, 166.33, 54.37, 52.71, 52.41, 52.37 (weak), 52.32 (weak), 52.28 (weak), 42.37, 39.26, 38.29, 38.17, 26.44, 24.95 (m, weak), 22.84, 22.82, 22.75 (m, weak), 21.50 (m, weak); ESI MS m/z 322.2 (M+H)$^+$; HPLC purity: 96.8% t$_R$=18.1 min (Condition I, UV 215 nm).

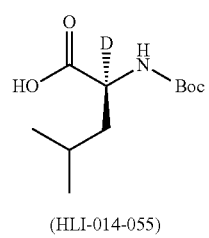

(HLI-014-055)

Compound Boc-L-Leu-2-d$_1$ (HLI-014-055) (41)

L-Leucine-2-d$_1$ (188 mg; 1.4 mmol; C/D/N Isotopes) was suspended in 8 mL of a 1:1 solution of water and tetrahydrofuran. The suspension was stirred, cooled to 0° C. (ice-water bath), and treated with sodium bicarbonate (353 mg; 4.2 mmol) followed by di-tert-butyl dicarbonate (373 mg; 1.7 mmol). The resulting suspension was stirred at 0° C. for 30 minutes and then at room temperature for 68 hours. The reaction mixture was extracted with ethyl acetate (3×). The aqueous layer was acidified to pH=3 with 1 N HCl and extracted with ethyl acetate (3×). All of the ethyl acetate extractions were combined, washed with brine (3×), dried over anhydrous Na$_2$SO$_4$, filtered and concentrated to provide a viscous oil (317 mg, 97%) of N-(tert-butyloxycarbonyl)-L-leucine-2-di: ESI MS m/z 233.2 (M+H)$^+$.

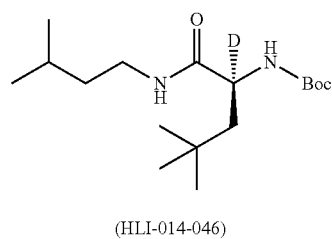

(HLI-014-046)

Compound (HLI-014-046) (42)

N-(tert-butyloxycarbonyl)-L-leucine-2-d$_1$ (41) (405 mg, 1.74 mmol), 1-hydroxybenzotriazole hydrate (346 mg, 2.26 mmol), and isoamylamine (166 mg, 1.91 mmol) were dissolved in CH$_2$Cl$_2$ (10 mL) at room temperature under nitrogen. With stirring, 1-ethyl-3-(3-dimethylaminopropyl)carbodiimide hydrochloride (500 mg, 2.61 mmol) was added. After stirring for three hours at room temperature, the reaction was diluted with CH$_2$Cl$_2$ (80 mL) and extracted with saturated NaHCO$_3$ (2×) and brine (1×). The organic layer was dried over anhydrous Na$_2$SO$_4$, filtered and concentrated to provide 525 mg of crude product 42 as a white semi-solid: APCI MS m/z 302.4 (M+H)$^+$.

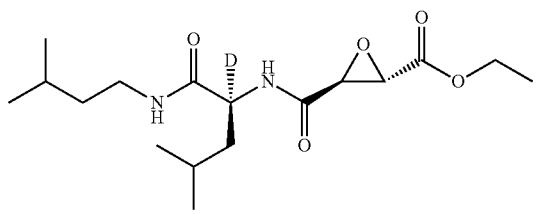

(HLI-014-059)

Compound (HLI-014-059) (43)

Compound 42 was dissolved in methanol (9 mL) and p-toluenesulfonic acid hydrate (414 mg, 2.18 mmol) was added with stirring. The solution was heated to 70° C. for two hours. After cooling, the reaction was evaporated to dryness to provide 279 mg of the tosic salt as a white semi-solid: ESI MS m/z 202.2 (C$_{11}$H$_{24}$DN$_2$O$^+$). To this material was added (2S, 3S)-3-(ethoxycarbonyl)oxirane-2-carboxylic acid (279 mg, 1.74 mmol; Peptech) and CH$_2$Cl$_2$ (15 ml) to provide a homogeneous solution. The solution was cooled to 0° C. (ice-water bath) under nitrogen. With stirring, 2-(7-azabenzotriazol-1-yl)-1,1,3,3-tetramethyl-uronium hexafluorophosphate (722 mg, 1.90 mmol) followed by diisopropylethyl amine (779 µL, 4.35 mmol) were added to the reaction solution. The resulting reaction was stirred at 0° C. for one hour and for two hours at room temperature.

The reaction was diluted with $CH_2Cl_2$ (150 ml) and extracted with saturated $NaHCO_3$ (2×) and brine (1×). The organic layer was dried over anhydrous $Na_2SO_4$, filtered and concentrated. The crude product was filtered through a silica gel plug eluting with ethyl acetate-hexane (1:9) followed by ethyl acetate-hexane (1:1). Concentration of the 1:1 ethyl acetate-hexane elution fractions provided the desired product 43 as a white solid (468 mg, 78%). Recrystallization from diisopropyl ether-ethanol yielded crystalline material: mp 122-123° C. $^1H$ NMR ($CDCl_3$, 500 MHz) δ 6.95 (s, 1H), 6.43 (br t, J=5.4 Hz, 1H), 4.19-4.27 (m, 2H), 3.67 (d, J=1.8 Hz, 1H), 3.46 (d, J=1.8 Hz, 1H), 3.23-3.30 (m, 1H), 3.14-3.20 (m, 1H), 1.49-1.62 (m, 4H), 1.36 (q, J=7.3 Hz, 2H), 1.29 (t, J=7.2 Hz, 3H), 0.87-0.91 (m, 12H); $^{13}C$ NMR ($CDCl_3$, 125 MHz) δ171.16, 166.81, 166.20, 62.47, 53.93, 52.96, 51.37 (m, weak), 41.40, 38.42, 38.14, 26.02, 24.99, 22.95, 22.59, 22.54, 22.41, 14.19; APCI MS m/z 344.2 $(M+H)^+$; HPLC purity: 98.6% $t_R$=22.7 min (Condition I, UV 215 nm).

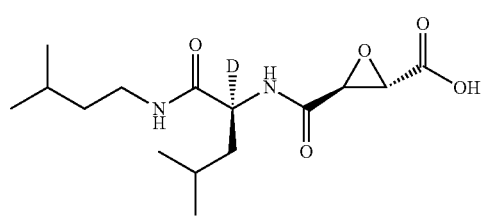

(ALP-479.000.01; HLI-014-060)

Compound (2S,3S)-3-((S)-2-$d_1$-1-(isopentylamino)-4-methyl-1-oxopentan-2-ylcarbamoyl)oxirane-2-carboxylic acid (ALP-479.000.01; HLI-014-060) (44)

The ethyl ester 43 from the above preparation (68 mg, 0.2 mmol) was dissolved in ethanol (3 mL). The stirred solution was cooled to 0° C. (ice-water bath) and treated with a solution of 85% KOH in ethanol (140 μL, 0.22 mmol). The resulting solution was stirred at 0° C. for 1 h and was concentrated to dryness. The residue partitioned between water and ethyl acetate. The layers were separated and the aqueous extracted once more with ethyl acetate. The aqueous layer was acidified to pH 1 with 1 N HCl and extracted with ethyl acetate (3×). The combined organic layers were dried over anhydrous $Na_2SO_4$, filtered and concentrated to provide a white powder (42 mg, 67%). Recrystallization from ethyl acetate-hexanes yielded acid 44 as a colorless crystal: mp 152-153° C.; $^1H$ NMR (acetone-$d_6$, 500 MHz) δ 7.62 (br s, 1H), 7.50 (br s, 1H), 3.66 (d, J=1.7 Hz, 1H), 3.58 (d, J=1.6 Hz, 1H), 3.17-3.26 (m, 2H), 1.57-1.68 (m, 4H), 1.37 (q, J=7.1 Hz, 2H), 0.87-0.96 (m, 12H); $^{13}C$ NMR (acetone-$d_6$, 125 MHz) δ 172.37, 169.0, 166.33, 54.36, 54.34, 52.71, 52.13 (m, weak), 42.50, 42.46, 39.26, 38.29, 38.17, 26.45, 25.54, 23.45, 22.84, 22.82, 22.26; APCI MS m/z 316.2 $(M+H)^+$; HPLC purity: 94.0% $t_R$=18.2 min (Condition I, UV 215 nm).

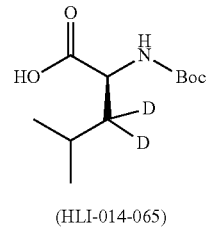

(HLI-014-065)

Compound Boc-L-Leu-3,3-$d_2$ (HLI-014-065) (45)

L-Leucine-3,3-$d_2$ (250 mg, 1.9 mmol, C/D/N Isotopes) was suspended in 10 mL of a 1:1 solution of water and tetrahydrofuran. The suspension was stirred, cooled to 0° C. (ice-water bath), and treated with sodium bicarbonate (474 mg, 5.6 mmol) followed by di-tert-butyl dicarbonate (492 mg, 2.3 mmol). The resulting suspension was stirred at 0° C. for 30 minutes and then at room temperature for 42 hours. The reaction mixture was extracted with ethyl acetate (3×). The aqueous layer was acidified to pH=2 with 1 N HCl and extracted with ethyl acetate (3×). All of the ethyl acetate extractions were combined, washed with brine (3×), dried over anhydrous $Na_2SO_4$, filtered and concentrated to provide a viscous oil (440 mg, 100%) of N-(tert-butyloxycarbonyl)-L-leucine-3,3-$d_2$: APCI MS m/z 234.2 $(M+H)^+$.

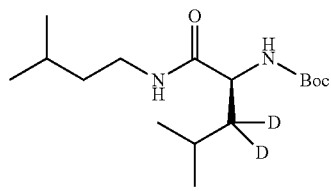

(HLI-014-071)

Compound (HLI-014-071) (46)

N-(tert-butyloxycarbonyl)-L-leucine-3,3-$d_2$ (45) (440 mg, 1.88 mmol), 1-hydroxybenzotriazole hydrate (374 mg, 2.44 mmol), and isoamylamine (176 mg, 2.01 mmol) were dissolved in $CH_2Cl_2$ (10 mL) at room temperature under nitrogen. With stirring, 1-ethyl-3-(3-dimethylaminopropyl) carbodiimide hydrochloride (540 mg, 2.82 mmol) was added. After stirring for 18 hours at room temperature, the reaction was diluted with $CH_2Cl_2$ (80 mL) and extracted with saturated $NaHCO_3$ (2×) and brine (1×). The organic layer was dried over anhydrous $Na_2SO_4$, filtered and concentrated to provide 525 mg of crude product 46 as a white foam: APCI MS m/z 303.4 $(M+H)^+$.

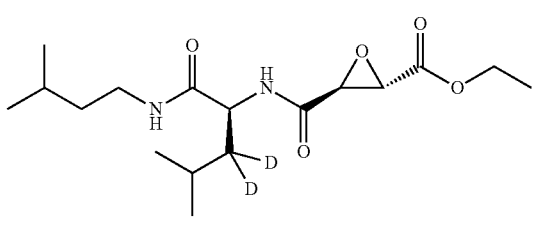

(ALP-###;
HLI-014-075)

(2S,3S)-Ethyl 3-((S)-3,3-d$_2$-1-(isopentylamino)-4-methyl-1-oxopentan-2-ylcarbamoyl)oxirane-2-carboxylate (HLI-014-075) (47)

This material was dissolved in methanol (10 mL) and p-toluenesulfonic acid hydrate (447 mg, 2.35 mmol) was added with stirring. The solution was heated to 70° C. for two hours. After cooling, the reaction was evaporated to dryness to provide 789 mg of tosic salt as a off-white foam: APCI MS m/z 203.2 (C$_{11}$H$_{23}$D$_2$N$_2$O$^+$). To this material was added (2S, 3S)-3-(ethoxycarbonyl)oxirane-2-carboxylic acid (304 mg, 1.90 mmol; Peptech) and CH$_2$Cl$_2$ (15 ml) to provide a homogeneous solution. The solution was cooled to 0° C. (ice-water bath) under nitrogen. With stirring, 2-(7-azabenzotriazol-1-yl)-1,1,3,3-tetramethyl-uronium hexafluorophosphate (794 mg, 2.10 mmol) followed by diisopropylethyl amine (681 µL, 3.80 mmol) were added to the reaction solution. The resulting reaction was stirred at 0° C. for one hour and for two hours at room temperature. The reaction was diluted with CH$_2$Cl$_2$ (100 ml) and extracted with saturated NaHCO$_3$ (2×) and brine (1×). The organic layer was dried over anhydrous Na$_2$SO$_4$, filtered and concentrated. The crude product 47 was filtered through a silica gel plug eluting with ethyl acetate-hexane (1:9) followed by ethyl acetate-hexane (1:1). Concentration of the 1:1 ethyl acetate-hexane elution fractions provided the desired product 47 as a white solid (649 mg, 99%). Recrystallization from t-butylmethyl ether-ethanol yielded crystalline material: $^1$H NMR (CDCl$_3$, 500 MHz) δ 6.89 (d, J=8.7 Hz, 1H), 6.36 (br t, J=5.4 Hz, 1H), 4.40 (d, J=8.7 Hz, 1H), 4.19-4.28 (m, 2H), 3.67 (d, J=1.8 Hz, 1H), 3.46 (d, J=1.7 Hz, 1H), 3.23-3.30 (m, 1H), 3.15-3.21 (m, 1H), 1.49-1.62 (m, 2H), 1.37 (q, J=7.3 Hz, 2H), 1.29 (t, J=7.1 Hz, 3H), 0.88-0.91 (m, 12H); $^{13}$C NMR (CDCl$_3$, 125 MHz) δ171.14, 166.79, 166.21, 62.49, 53.95, 53.00, 51.55, 40.70 (m, weak), 38.44, 38.16, 26.03, 24.85, 22.91, 22.60, 22.55, 22.35, 14.20; APCI MS m/z 345.2 (M+H)$^+$; HPLC purity: 99.5% t$_R$=22.78 min (Condition I, UV 215 nm).

Compound (2S,3S)-3-((S)-3,3-d$_2$-1-(isopentylamino)-4-methyl-1-oxopentan-2-ylcarbamoyl)oxirane-2-carboxylic acid (ALP-487.000.01; HLI-014-078) (48)

The ethyl ester 47 (101 mg, 0.29 mmol) was dissolved in ethanol (4 mL). The stirred solution was treated with a solution of 85% KOH in ethanol (450 µL, 0.29 mmol) at room temperature. The resulting solution was stirred at room temperature for 1 h and was concentrated to dryness. The residue was partitioned between water and dichloromethane. The layers were separated and the aqueous extracted once more with dichloromethane. The aqueous layer was acidified to pH 2 with 1 N HCl and extracted with ethyl acetate (3×). The combined organic layers were dried over anhydrous Na$_2$SO$_4$, filtered and concentrated to provide acid 48 as a white solid (85 mg, 92%). Recrystallization from ethyl acetate-hexanes yielded acid 48 as a colorless crystal: mp 149-150° C.; $^1$H NMR (acetone-d$_6$, 500 MHz) δ 7.63 (d, J=8.5 Hz, 1H), 7.50 (br s, 1H), 4.48 (d, J=8.6 Hz, 1H), 3.66 (d, J=1.7 Hz, 1H), 3.58 (d, J=1.8 Hz, 1H), 3.17-3.26 (m, 2H), 1.57-1.67 (m, 2H), 1.37 (q, J=7.2 Hz, 2H), 0.87-0.96 (m, 12H); $^{13}$C NMR (acetone-d$_6$, 125 MHz) δ172.39, 169.00, 166.41, 54.35, 54.33, 52.71, 52.32, 52.24 (m, weak), 41.50 (br m, weak), 39.25, 38.30, 38.17, 26.44, 25.39, 23.39, 22.83, 22.81, 22.20; APCI MS m/z 317.2 (M+H)$^+$; HPLC purity: 97.4% t$_R$=18.1 min (Condition I, UV 215 nm).

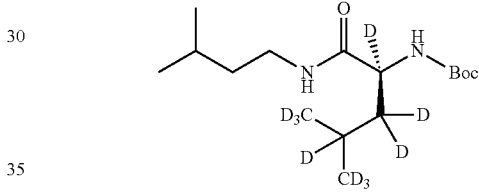

(HLI-014-066)

Compound (HLI-014-066) (50)

N-(tert-butyloxycarbonyl)-L-leucine-d$_{10}$ hydrate (49) (250 mg, 0.96 mmol, C/D/N Isotopes), 1-hydroxybenzotriazole hydrate (191 mg, 1.25 mmol), and isoamylamine (92 mg, 1.06 mmol) were dissolved in CH$_2$Cl$_2$ (10 mL) at room temperature under nitrogen. With stirring, 1-ethyl-3-(3-dimethylaminopropyl)carbodiimide hydrochloride (276 mg, 1.44 mmol) was added. After stirring for 18 hours at room temperature, the reaction was diluted with CH$_2$Cl$_2$ (100 mL) and extracted with saturated NaHCO$_3$ (2×) and brine (1×). The organic layer was dried over anhydrous Na$_2$SO$_4$, filtered and concentrated to provide 313 mg of crude product 50 as a viscous oil: APCI MS m/z 311.4 (M+H)$^+$.

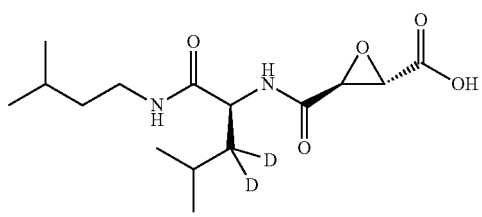

(ALP-487.000.01;
HLI-014-078)

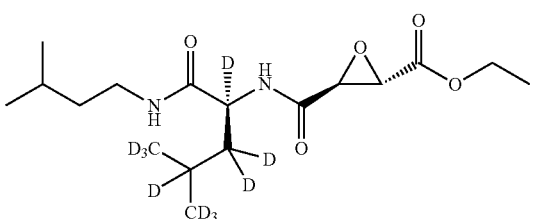

(ALP-###;
HLI-014-070)

Compound (2S,3S)-3-((S)-2,3,3,4,5,5,5-d$_7$-1-(iso-pentylamino)-1-oxo-4-(methyl-d$_3$)pentan-2-ylcarbamoyl) oxirane-2-carboxylate (HLI-014-070) (51)

This material was dissolved in methanol (10 mL) and p-toluenesulfonic acid hydrate (237 mg, 1.25 mmol) was added with stirring. The solution was heated to 70° C. for three hours. After cooling, the reaction was evaporated to dryness to provide 440 mg of the tosic salt as a viscous oil: APCI MS m/z 211.2 ($C_{11}H_{15}D_{10}N_2O^+$). To this material was added (2S, 3S)-3-(ethoxycarbonyl)oxirane-2-carboxylic acid (160 mg, 1.00 mmol, Peptech) and CH$_2$Cl$_2$ (15 ml) to provide a homogeneous solution. The solution was cooled to 0° C. (ice-water bath) under nitrogen. With stirring, 2-(7-azabenzotriazol-1-yl)-1,1,3,3-tetramethyl-uronium hexafluorophosphate (418 mg, 1.10 mmol) followed by diisopropylethylamine (358 μL, 2.00 mmol) were added to the reaction solution. The resulting reaction was stirred at 0° C. for 30 minutes and for one hour at room temperature. The reaction was diluted with CH$_2$Cl$_2$ (80 ml) and extracted with saturated NaHCO$_3$ (2×) and brine (1×). The organic layer was dried over anhydrous Na$_2$SO$_4$, filtered and concentrated. The crude product 51 was filtered through a silica gel plug eluting with ethyl acetate-hexane (1:9) followed by ethyl acetate-hexane (1:1). Concentration of the 1:1 ethyl acetate-hexane elution fractions provided the desired product 51 as a white solid (345 mg, 98%). Recrystallization from diisopropyl ether-ethanol yielded crystalline material: $^1$H NMR (CDCl$_3$, 500 MHz) δ 6.84 (s, 1H), 6.43 (br t, J=5.3 Hz, 1H), 4.19-4.29 (m, 2H), 3.67 (d, J=1.7 Hz, 1H), 3.46 (d, J=1.7 Hz, 1H), 3.24-3.30 (m, 1H), 3.16-3.23 (m, 1H), 1.58 (septet, J=6.7 Hz, 1H), 1.37 (q, J=7.3 Hz, 2H), 1.30 (t, J=7.3 Hz, 3H), 0.89 (d, J=6.6 Hz, 6H); $^{13}$C NMR (CDCl$_3$, 125 MHz) δ171.13, 166.78, 166.22, 62.50, 53.96, 53.03, 51.24 (t, weak), 41.05 (br, weak), 38.45, 38.16, 26.04, 24.00 (br, weak), 22.61, 22.56, 14.21; APCI MS m/z 353.4 (M+H)$^+$; HPLC purity: 99.3% t$_R$=22 6 min (Condition I, UV 215 nm).

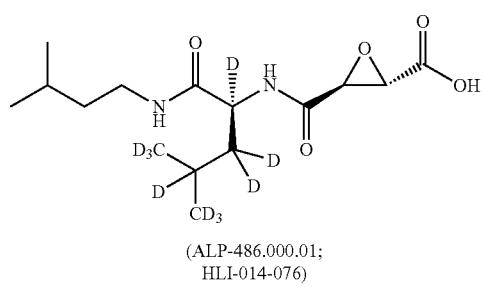

(ALP-486.000.01; HLI-014-076)

Compound (2S,3S)-3-(S)-2,3,3,4,5,5,5-d$_7$-1-(isopentylamino)-1-oxo-4-(methyl-d$_3$)pentan-2-ylcarbamoyl)oxirane-2-carboxylic acid (ALP-486.000.01; HLI-014-076) (52)

The ethyl ester 51 from the above preparation (105 mg, 0.3 mmol) was dissolved in ethanol (4 mL). The stirred solution was treated with a solution of 85% KOH in ethanol (448 μL; 0.3 mmol) at room temperature. The resulting solution was stirred at room temperature for 45 minutes and was concentrated to dryness. The residue was partitioned between water and dichloromethane. The layers were separated and the aqueous extracted once more with dichloromethane. The aqueous layer was acidified to pH 2 with 1N HCl and extracted with ethyl acetate (3×). The combined organic layers were dried over anhydrous Na$_2$SO$_4$, filtered and concentrated to provide acid 52 as a white solid (78 mg, 81%). Recrystallization from ethyl acetate-hexanes yielded acid 52 as a colorless crystal: mp 150-151° C.; $^1$H NMR (acetone-d$_6$, 500 MHz) δ7.62 (br s, 1H), 7.50 (br s, 1H), 3.66 (d, J=1.8 Hz, 1H), 3.58 (d, J=1.6 Hz, 1H), 3.17-3.27 (m, 2H), 1.59 (septet, J=6.7 Hz, 1H), 1.37 (q, J=7.2 Hz, 2H), 0.88 (d, J=6.7 Hz, 6H); $^{13}$C NMR (acetone-d$_6$, 125 MHz) δ172.41, 169.01, 166.38, 54.36, 52.70, 52.25 (br, weak), 41.50 (br, weak), 39.25, 38.28, 38.16, 26.44, 22.83, 22.81; APCI MS m/z 325.4 (M+H)$^+$; HPLC purity: 99.3% t$_R$=18.0 min (Condition I, UV 215 nm).

Example 8: Modulation of Aβ Levels in an Animal Model of Aβ Production

This example demonstrates the successful reduction of levels of brain Aβ40 and Aβ42 in wild-type guinea pigs, an animal model of Aβ production. Wild-type guinea pigs are an art-accepted model for normal Aβ production and are known to produce Aβ peptides that are immunologically identical to human Aβ. Wild-type guinea pigs represent an animal model for a physiological hallmark of Alzheimer's disease.

Oral dosing of AB-007 in Guinea Pigs in DMSO solution

Guinea Pigs #70 (3 weeks of age, Charles River Labs) were gavaged once daily for 7 days with AB-007 suspended in DMSO (500 uL). 10 animals were administered each of the following doses: 0 mg/kg/day, 0.1 mg/kg/day, 0.5 mg/kg/day, 1 mg/kg/day, 5 mg/kg/day, 10 mg/kg/day, or 50 mg/kg/day.

Preparation of Samples

On the 7th day of administration of AB-007, 4 hours after the final dosing, the animals were sacrificed (isoflurane anesthesia with exsanguination), the brains removed and frozen in liquid nitrogen. In preparation for testing, the frozen hemi-brains were weighed, and homogenized at 1 mL/100 mg in 1 mL THB+PIC (Tissue Homogenization Buffer: 250 mM sucrose, 20 mM TRIS base, 1 mM EDTA, 1 mM EGTA in ddH$_2$O, pH 7.4). Homogenized brain samples were snap frozen in liquid nitrogen.

Measurement of Brain Aβ40 and Brain Aβ42 (pg/mg)

Figure 2:
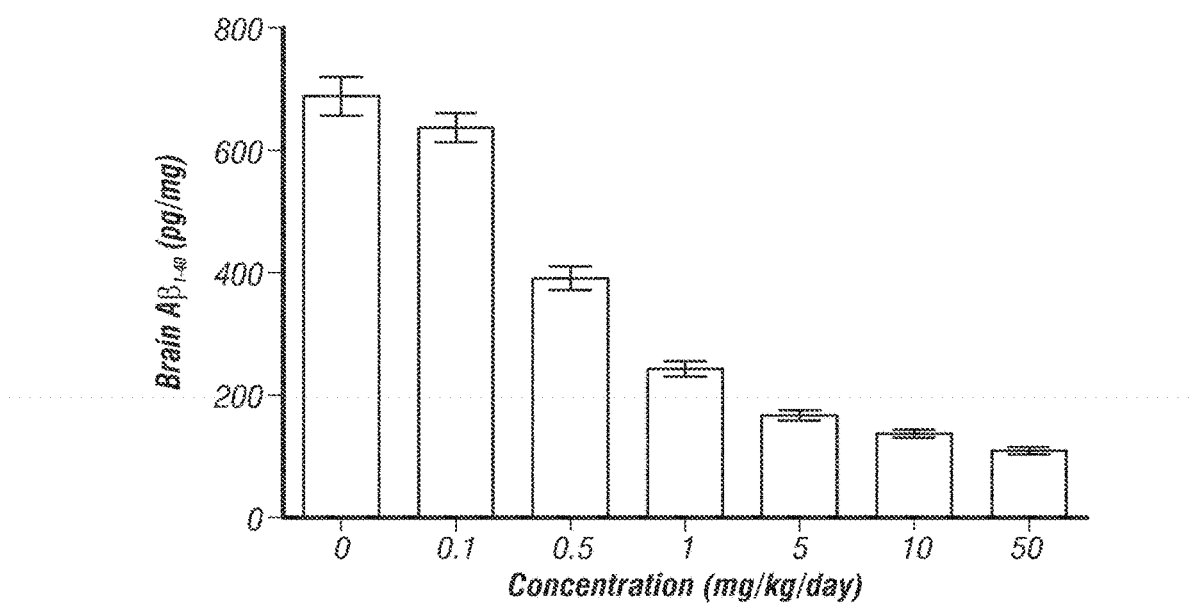
FIG. 2 graphically illustrates data showing the measurements of brain $A\beta_{1-40}$ in guinea pigs administered between 0 and 50 mg/kg/day AB-007 via oral gavage for 7 days, as discussed in detail in Example 8, below.
Figure 3:
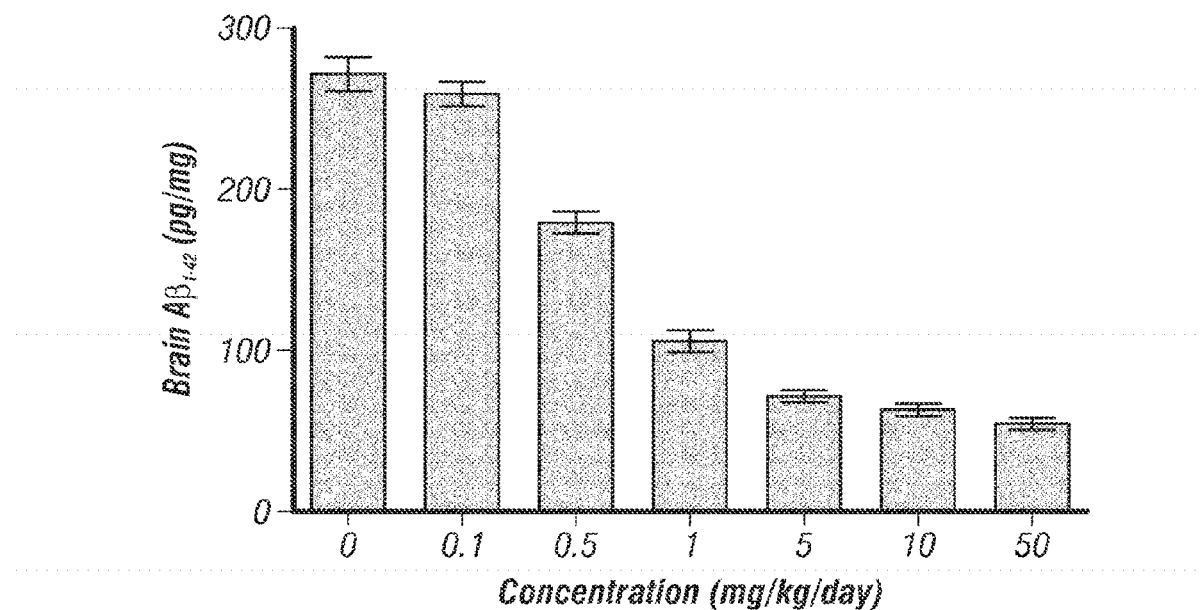
FIG. 3 graphically illustrates data showing the measurements of brain $A\beta_{1-42}$ in guinea pigs administered between 0 and 50 mg/kg/day AB-007 via oral gavage for 7 days, as discussed in detail in Example 8, below.

Duplicate ELISA assays were run on thawed undiluted homogenized brain samples (using Amyloid-β (1-40) ELISA and Amyloid-β (1-42) ELISA kits and following instructions provided by IBL International GmbH, Hamburg, Germany) to measure the concentration of brain Aβ40 and brain Aβ42 in pg/mg brain sample. As shown in FIG. 1, after 7 days of 10 mg/kg/day dosing reduces brain Aβ40 and of brain Aβ42 by 42% relative to vehicle control (0 mg/kg/day dosing). Measurement of brain Aβ40 and brain Aβ42 (pg/mg) for each of the doses from Example 8 are provided in FIG. 2 and FIG. 3 respectively.

Measurement of Cathepsin B Activity

Figure 4:
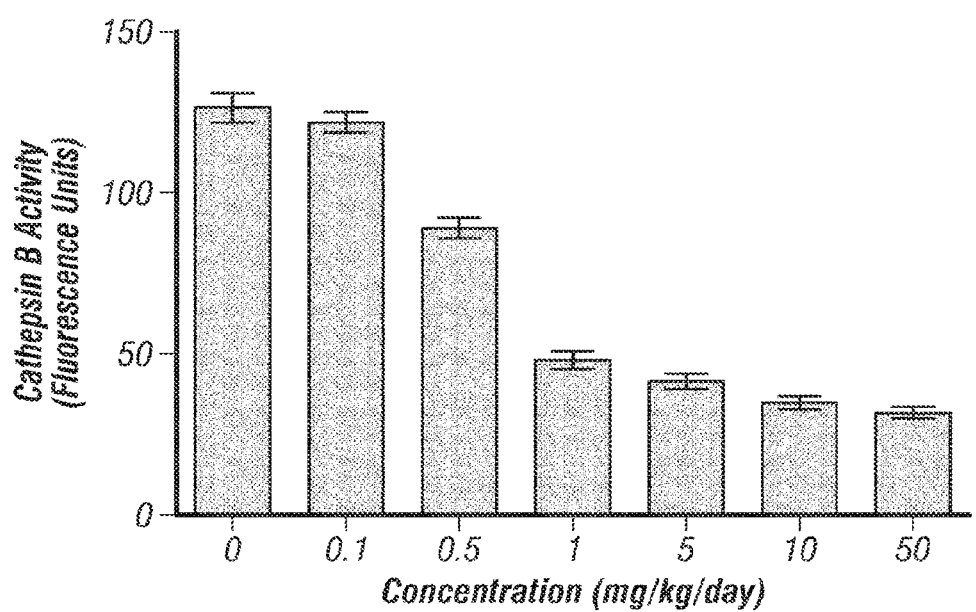
FIG. 4 graphically illustrates data showing the measurements of Cathepsin B activity after administration of between 0 and 50 mg/kg/day AB-007 to guinea pigs via oral gavage for 7 days, as discussed in detail in Example 8, below.

Whole tissue brain homogenates (5 uL) were added to cold 1× cell Extraction Buffer (245 uL) (final protein concentration of roughly 2.0 mg/mL). The lysate was incubated on ice and centrifuged. The supernatant was transferred to a new tube and kept on ice (cell lysate had approximate protein concentration of 2 mg/mL). The Cathepsin B activity was measured using the Cathepsin B Activity Assay Kit (Fluorometric) (ab65300, abcam, Cambridge, Mass.). Measurement of Cathepsin B activity for each of the doses from Example 8 are provided in FIG. 4.

Measurement of β-secretase Activity (BACE-1)

Figure 5:
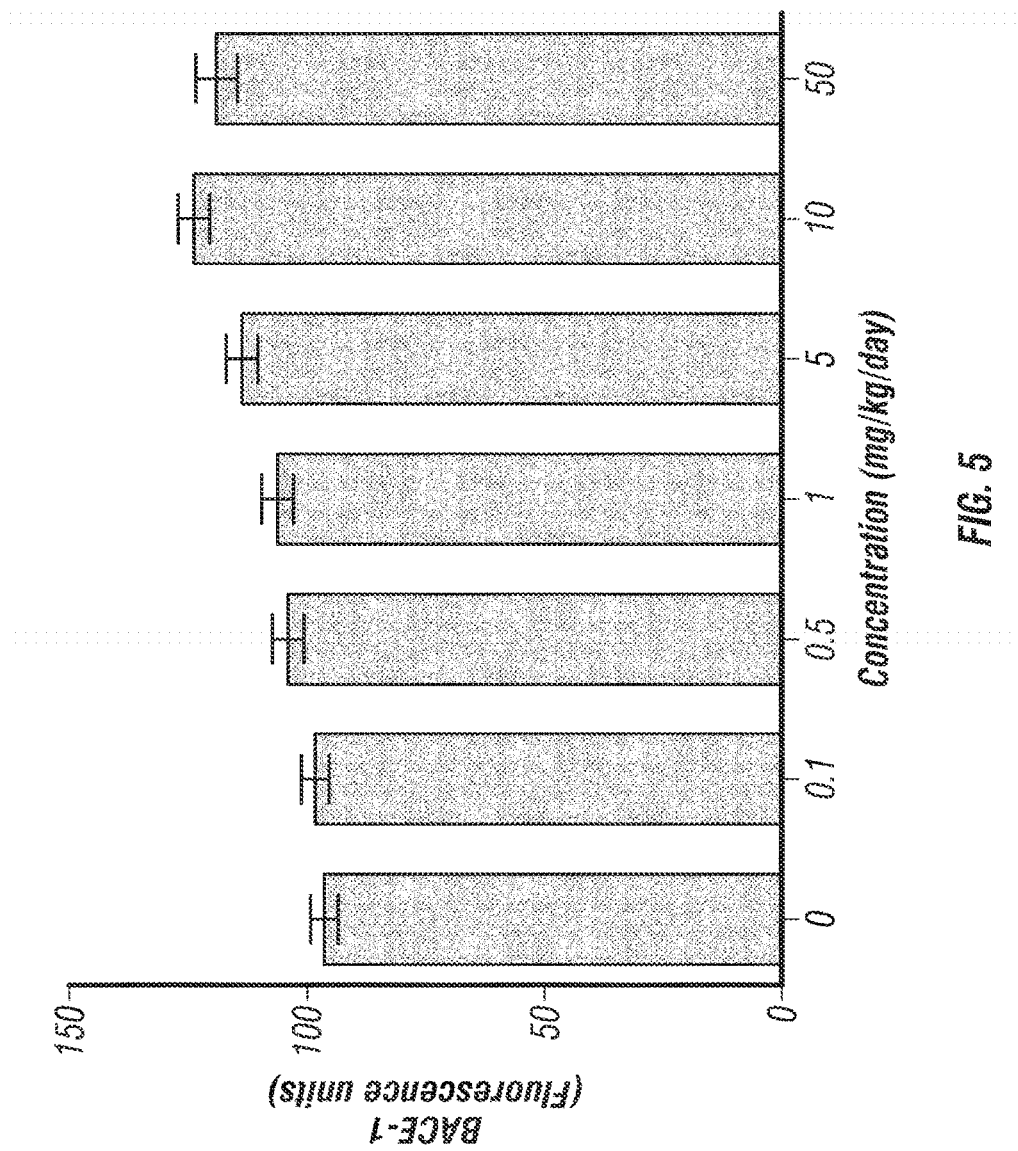
FIG. 5 graphically illustrates data showing the measurements of BACE-1 activity after administration of between 0 and 50 mg/kg/day AB-007 to guinea pigs via oral gavage for 7 days, as discussed in detail in Example 8, below.

Whole tissue brain homogenates (5 uL) were added to cold 1× cell Extraction Buffer (245 uL) (final protein concentration of roughly 2.0 mg/mL). The lysate was incubated on ice and centrifuged. The supernatant was transferred to a new tube and kept on ice (cell lysate had approximate protein concentration of 2 mg/mL). The β-secretase activity was measured using β-secretase Activity Kit (Catalog Number: FP002, R&D Systems, Minneapolis, Minn.). Fluorescence between 495 and 510 nm was measured, following EDANS excitation between 335 and 355 nm Measurement of BACE-1 for each of the doses from Example 8 are provided in FIG. 5.

Example 9: Modulation of Aβ Levels in an Animal Model of Aβ Production

This example presents data and analysis demonstrating that oral administration of AB-007 (E64d, loxistatin) results in a dose response reduction in brain Aβ(40) and brain Aβ(42) peptides, CSF Aβ and CSF Aβ(42) peptides, and plasma Aβ(40) and Aβ(42) peptides. These data demonstrate that oral administration of AB-007 (E64d, loxistatin) to guinea pigs results in a dose response reduction of brain cathepsin B activity, and that brain cathepsin B inhibition reduces brain Aβ(40) and Aβ(42) peptides. These data demonstrate that oral administration of the invention's exemplary composition of the invention "E64d7" (a hepta-deuterated isoform of E64d, illustrated above) to guinea pigs results in a dose response reduction in brain Aβ(40) and brain Aβ(42) peptides, cerebrospinal fluid (CSF) Aβ and CSF Aβ(42) peptides, and plasma Aβ(40) and Aβ(42) peptides. These data demonstrate that once-a-day oral administration of "E64d7" to guinea pigs results in a dose response reduction of brain cathepsin B activity; and that brain cathepsin B inhibition reduces brain Aβ(40) and Aβ(42) peptides. These data demonstrate that feeding mice E64d-doped chow for 1 or 3 months caused a significant reduction in brain Aβ(40) and Aβ(42) peptides in both the young and old mice relative to age-matched controls.

This example presents data and analysis demonstrating that that feeding APPlon mice E64d-doped chow for either 1 month or 3 months to either age group significantly reduced the mean latency period relative to age-matched controls; thus, this treatment improved the memory deficit in animals having either mild or severe spatial memory deficit; and the data demonstrates that oral administration of E64d is effective for improving the early and late memory deficit that develops in Alzheimer's disease.

This example presents data and analysis demonstrating that in general brain Aβ(40) and Aβ(42) is highly positively correlated with spatial memory deficit and that treating the animals with E64d results in about the same or slightly less positive correlation in the young animals and a much greater positive correlation in old animals relative to age-matched controls. These data also illustrate the efficacy of E64d in improving memory deficit in aged animals; and while the invention is not limited by any particular mechanism of action, these also data illustrate the efficacy of E64d in decreasing levels of brain Aβ(40) and Aβ(42) peptide.

Materials and Methods

AB-007 (E64d, loxistatin) AB-007 (E64d, loxistatin) was synthesized by American Life Science Pharmaceuticals (San Diego, Calif.). Purity was determined to be 99% by reverse-phase high-pressure liquid chromatograph (RP-HPLC) and the identity of the compound confirmed by $^1$H nuclear magnetic resonance (NMR), melting point, elemental analysis and liquid chromatography mass spectroscopy (LCMS). E64d exhibited excellent stability with 99% of the compound remaining after a 5-week stability test at 60° C.

Animal Models

Guinea Pigs. Guinea Pigs (Harley strain, average weight 400 g corresponding to animals about 6 weeks old) were obtained from Charles River (Wilmington, Mass.). The animals were given free access to standard chow and water before and during the experiment.

Transgenic AD Mice. Transgenic mice expressing human APP containing the wt β-secretase site and the London mutant γ-secretase site sequences (also called "transgenic APPlon mice", or "London APP mice") were generated at the Ralph A. Johnson VA Medical Center (Charleston, S.C.) by methods previously described, see e.g., Hook, et al. (2008) J. Biol. Chem. 283:7745-7753. Briefly, APPLn was generated using site-directed mutagenesis to insert the V7171 London mutation into human APP cDNA. The mouse strain was created in a C57BL/6 mouse background using the Thy-1.2 expression cassette driven by the Thy-1 promoter containing an SV40 polyadenylation site. Mice were given free access to food and water before and during the experiment.

Oral Formulations

Gavage Formulation: Delivering a drug by gavage offers the advantage of accurate dosing but is traumatic and thus only suitable for relatively short dosing periods. Gavage delivery was used for the guinea pig work. E64d was resuspended in DMSO at indicated concentrations (see Figures, and below) and guinea pigs were gavaged daily using a feeding tube. Vehicle control animals were provided DMSO alone.

Mouse Chow Formulation: Delivering a drug by doped chow feeding allows for extended dosing periods without trauma but results in less accurate dosing because individual animals consume variable amounts of chow. Doped chow feeding was used for the transgenic AD mice experiments. The guinea pig data found that a 10 mg/kg/day E64d oral dose was maximally effective at lowering brain Aβ and cathepsin B activity and, therefore, that dose was used for the doped chow studies to increase the chances of a positive outcome. E64d doped mouse chow was prepared in the mouse chow routinely used to feed the transgenic AD mice (2018, Teklad Global 18% Protein Rodent Diet, Harlan Laboratories, Inc. of Madison, Wis.). Briefly, 40 milligrams (mg) of E64d per kilogram (kg) of chow was processed into standard 0.5 inch pellets according to the manufacturer's procedure. The resulting doped chow was analyzed by RP-HPLC and found to contain 20 mg of E64d per kg of chow. Studies of chow spiked with E64d found that RP-HPLC spike recovery of about 50%, suggesting that the chow contained 40 mg E64d per kg of chow. The mice consume on average about 5 grams (gm) of chow per day and had an average body weight of about 20 μm. Thus, an average mice ate a calculated daily E64d dose of 10 mg/kg.

Oral Dosing

Guinea Pig Gavage Dosing: Guinea pigs were gavaged daily for one week. Guinea pigs were lightly anesthetized with isoflurane prior to gavaging. 250 μl of compound solution was gavaged daily per animal and animals were sacrificed 4 hrs after the last dosing.

Mouse Chow Dosing: Two age groups of transgenic AD mice treated with two dose regimes were studied. One group of animals aged for 6 months and the other for 12 months before beginning E64d treatment, which consisted of either feeding the animals E64d doped chow for 1 or 3 months (controls received normal chow for the same time periods).

Thus, all animals were fed normal chow up to the appropriate age and then the experimental animals switched to feeding on E64d doped chow. At all times and for both formulations, the mice were fed ad libitum. There was no difference in the amount of E64d doped and normal chow consumed.

Brain Aβ Analysis

The brain Aβ analysis method was that previously described for guinea pigs and transgenic AD mice, see e.g., Hook (2007) Biol. Chem. 388:979-983. Animals were sacrificed and brain extracts were prepared as previously described, see e.g., Hook (2008) J. Biol. Chem. 283:7745-7753. Briefly, brain extracts were homogenized (1:3 weight/volume of buffer) in buffer of 5 M guanidine HCl in 50 mM Tris-HCl, pH 7.6, 150 mM NaCl, plus protease inhibitors (Sigma). Homogenates were diluted to 0.5 M guanidine and centrifuged (200,000 g for 20 min), and supernatant and pellet fractions were collected. Protein content was determined by the Bradford method. Enzyme-linked immunosorbent assays (ELISAs) measured Aβ peptides by methods previously described, see e.g., Hook (2007) Biol. Chem. 388:247-252. The pellet from the brain extract procedure was sonicated in 6 M guanidine and centrifuged at 200,000 g for 20 min at 4° C., and the supernatant was diluted to 0.5 M guanidine. The two supernatants were combined, and Aβ40 and Aβ42 were determined using ELISA kits specific for each peptide (IBL, JP27718 and JP27711).

Cerebrospinal Fluid (CSF) Aβ

The CSF Aβ in guinea pigs was measured as follows: CSF was collected from the guinea pig brains and protease inhibitors were added and Aβ40 and Aβ42 were determined using ELISA kits specific for each peptide (IBL, JP27718 and JP27711).

Plasma Aβ

The plasma Aβ in guinea pigs was measured as follows: Plasma samples were collected from the guinea pigs following sacrifice, protease inhibitors were added and Aβ40 and Aβ42 were determined using ELISA kits specific for each peptide (IBL, JP27718 and JP27711).

Brain Cathepsin B Analysis

The brain cathepsin B activity in guinea pigs was measured as follows: Cathepsin B activity was determined using a fluorometric assay kit from Abcam, Inc. (catalog ab65300; Cambridge, Mass.) as described by the manufacturer.

Brain BACE1 Analysis

The brain BACE1 activity in guinea pigs was measured by Beta secretase activity was determined using a fluorometric assay kit from Abcam (ab65357) as described by the manufacturer.

Spatial Memory Deficit

The memory deficit in transgenic $APP_{in}$ mice (APPlon mice) was measured using the Morris water maze test. Briefly, the spatial memory capability of each animal was assessed by the Morris water maze test as described e.g., by S. Mueller-Steiner (2006) Neuron 51:703-714; using catalog part no. 700-0718-4W, of SD Instruments, San Diego, Calif. The Morris water maze test evaluates memory in a swimming test. Mice were individually trained in a 1.2 meter open field water maze in a pool filled with water to a depth of 30 cm and maintained at 25° C. An escape platform (10 cm square) was placed 1 cm below the surface of the water. All animals underwent nonspatial pretraining for 3 consecutive days, which prepared the animals for the final behavioral test to determine the retention of memory to find the platform. Two days following the nonspatial pretraining, the hidden platform was placed in the center of one quadrant of the pool, the animal was released facing the pool wall in a random fashion, the time was recorded (latency period), and the distance traveled to reach the platform was measured using video recording (Smart Video Tracking System; SD Instruments).

Animal treatment: Animal studies were conducted according to regulations by the NIH and as approved by the IACUC at the Medical University of South Carolina and Ralph H. Johnson VA Medical Center.

Figure 6A:
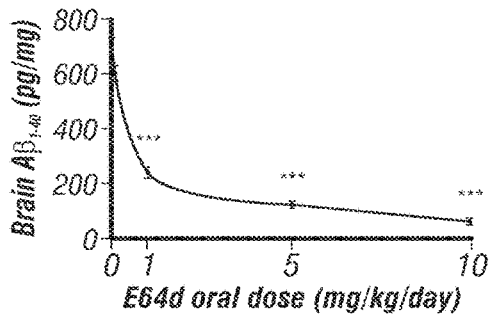
FIG. 6A, FIG. 6B, FIG. 6C, FIG. 6D, FIG. 6E, and FIG. 6F graphically illustrate data showing that once-a-day oral administration of AB-007 (E64d, loxistatin) to guinea pigs results in a dose response reduction.
Figure 6B:
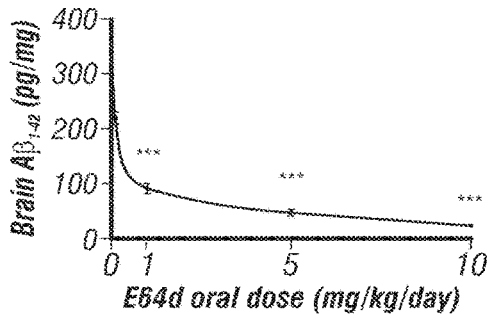
Figure 6C:
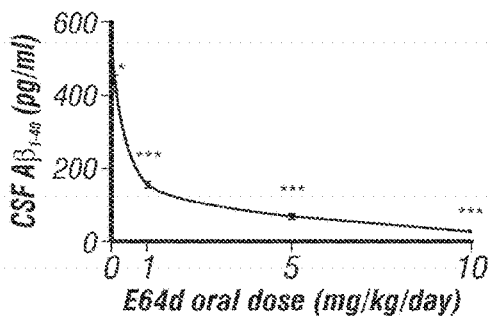
Figure 6D:
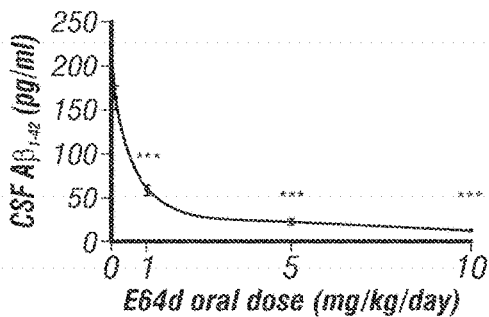
Figure 6E:
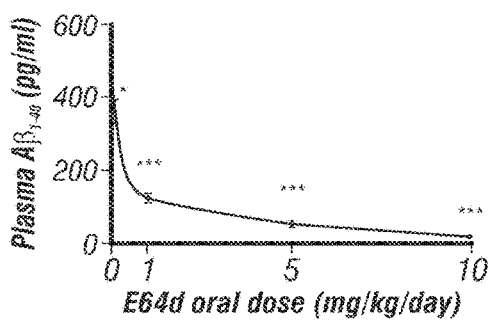
Figure 6F:
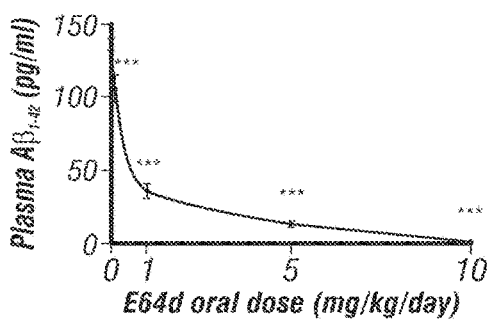

FIG. 6 graphically illustrates data showing that once-a-day for one week oral administration of E64d to guinea pigs results in a dose response reduction in FIG. 6(A) brain Aβ(40), FIG. 6 (B) brain Aβ(42), FIG. 6 (C) CSF Aβ, FIG. 6 (D) CSF Aβ(42), FIG. 6 (E) plasma Aβ(40) and FIG. 6 (F) plasma Aβ(42). Similar biphasic reductions in Aβ occurred for both peptide forms and in all compartments. Stars represent means that are statistically different from the no E64d dose group (student's t test * p=0.02, *** p<0.001).

Figure 7A:
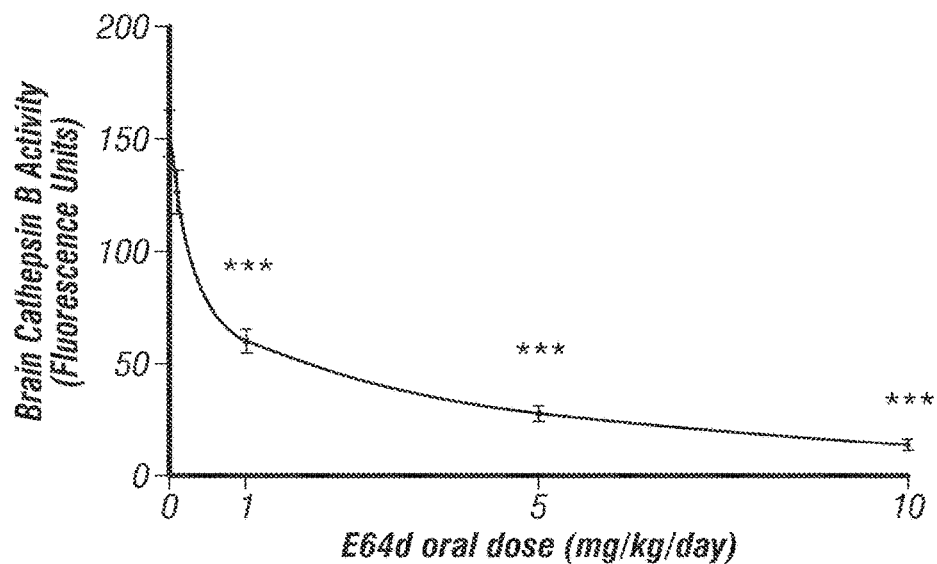
FIG. 7A and FIG. 7B graphically illustrate data showing.
Figure 7B:
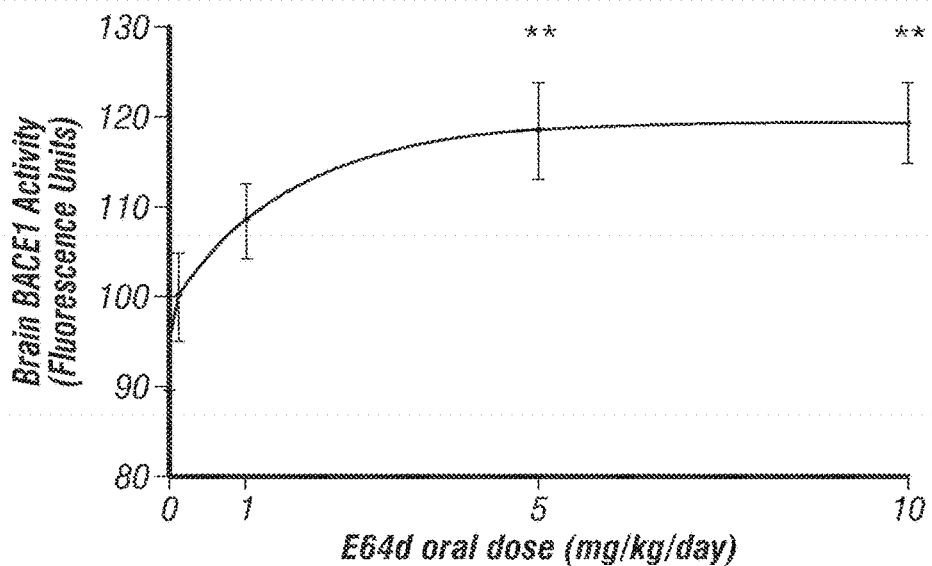

FIG. 7A (upper graph) graphically illustrates data showing that once-a-day for one week oral administration of AB-007 (E64d, loxistatin) to guinea pigs results in a dose response reduction brain cathepsin B activity, which is similar to the biphasic lowering of Aβ, e.g., as demonstrated in FIG. 6. In contrast, as illustrated in FIG. 7(B) (lower graph), that same treatment results in an increase in brain BACE1 activity. Stars represent means that are statistically different from the no E64d dose group (student's t test  p<0.006, * p<0.001).

FIG. 8 graphically illustrates data showing paired guinea pig data for brain Aβ(40) or Aβ(42) vs brain cathepsin B or BACE1 activity, respectively for the combined AB-007 (E64d, loxistatin) dose groups. FIG. 8(A) Brain Aβ(40) vs brain cathepsin B activity shows a significant positive correlation (linear regression analysis, r squared 0.98, 95% confidence interval for the slope is 0.21 to 0.22, which is a significant non-zero slope at p<0.0001). This result is consistent with the hypothesis that brain cathepsin B inhibition reduces brain Aβ(40). FIG. 8(B) Brain Aβ(42) vs brain cathepsin B activity also has a significant positive correlation (r squared 0.87, 95% confidence interval for the slope is 0.45 to 0.56, which is a significant non-zero slope at p<0.0001). This data is also consistent with brain cathepsin B inhibition reducing brain Aβ(42). FIG. 8(C): Brain Aβ(40) vs brain BACE1 activity demonstrates a small negative correlation (r squared 0.45, 95% confidence interval for the slope is −0.06 to −0.03, which is a significant non-zero slope at p<0.0001). These data are not consistent with brain BACE1 inhibition decreasing brain Aβ(40). FIG. 8(D) Brain Aβ(42) vs brain BACE1 activity has a negative correlation (r squared 0.36, 95% confidence interval the slope is −0.14 to −0.06, which is a significant non-zero slope at p<0.001). These data are also not consistent with brain BACE1 inhibition causing the decrease in Aβ(42).

Figure 9A:
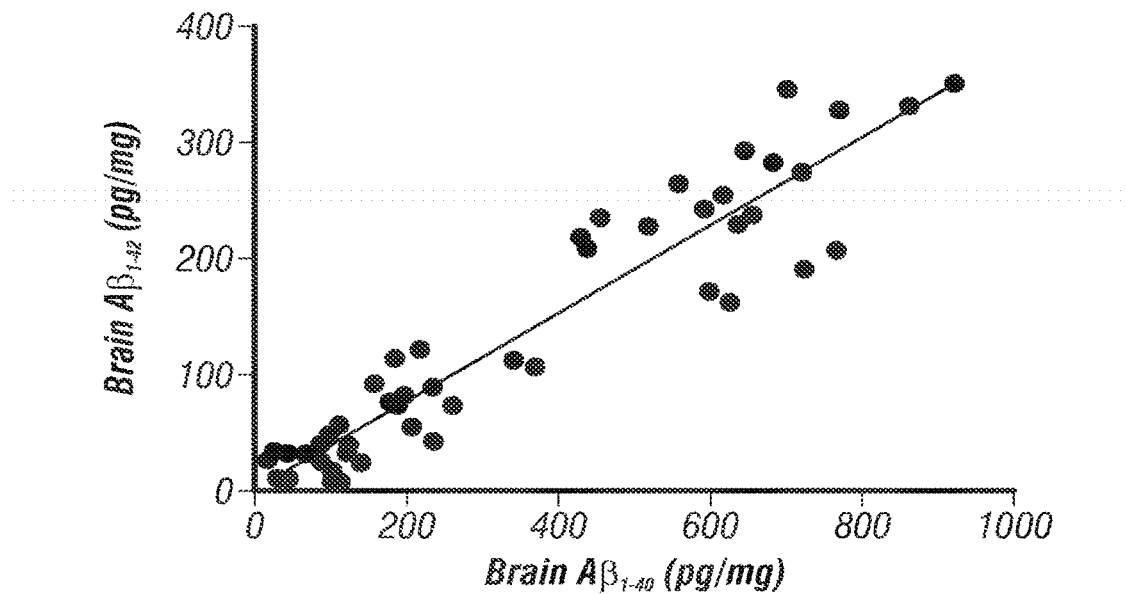
FIG. 9A and FIG. 9B graphically illustrate data showing paired guinea pig data for brain Aβ(40) vs Aβ(42) and brain cathepsin B vs BACE1 activity for all AB-007 (E64d, loxistatin) dose groups combined.
Figure 9B:
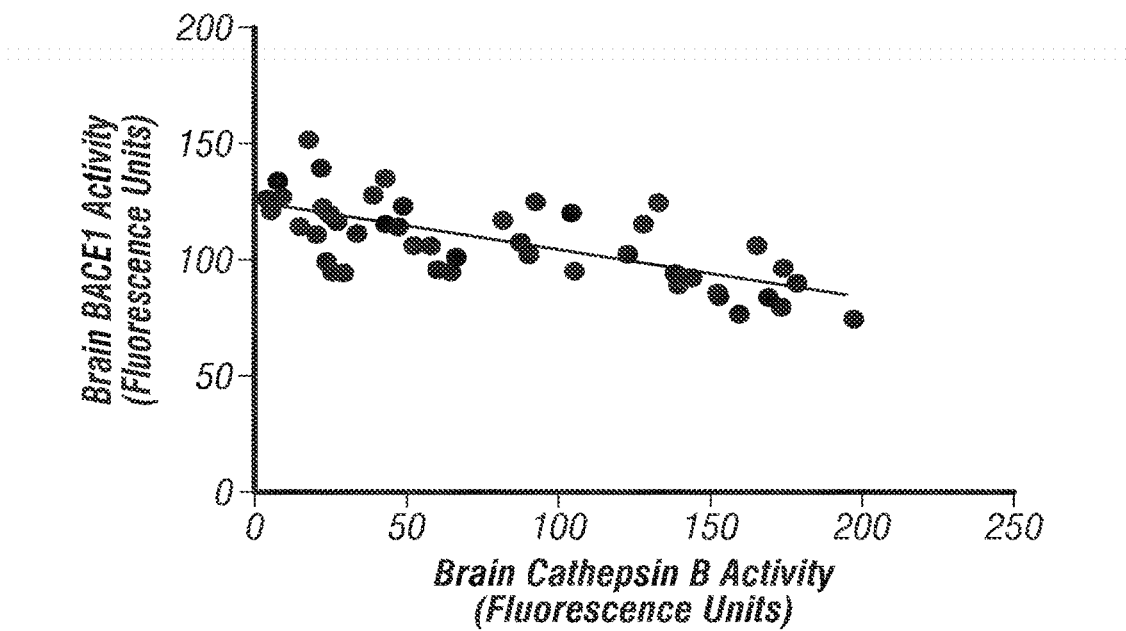

FIG. 9 graphically illustrates data showing paired guinea pig data for brain Aβ(40) vs Aβ(42) and brain cathepsin B vs BACE1 activity for all AB-007 (E64d, loxistatin) dose groups combined. FIG. 9(A) Brain Aβ(40) vs Aβ(42) shows a significant positive correlation (linear regression analysis, r squared 0.89, 95% confidence interval for the slope is 0.34 to 0.42, which is a significant non-zero slope at p<0.0001). This result is consistent with both forms of Aβ being reduced in each animal at a ratio of about 1 to 0.4 Aβ(40) to Aβ(42). FIG. 9(B) Brain cathepsin B vs BACE1 activity shows a slight negative correlation (r squared 0.47, 95% confidence interval for the slope is −0.27 to −0.14, which is a significant non-zero slope at p<0.0001). These data are consistent with brain BACE1 activity compensating for decreased cathepsin B activity.

Figure 10A:
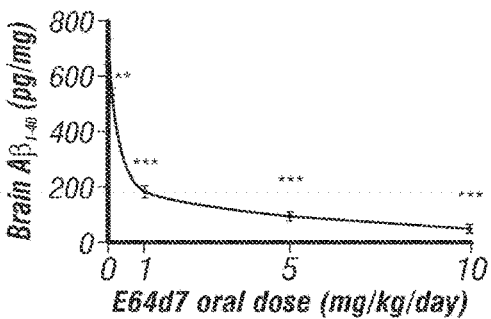
FIG. 10A, FIG. 10B, FIG. 10C, FIG. 10D, FIG. 10E and FIG. 10F graphically illustrate data showing that once-a-day for a week oral administration of the invention's exemplary composition of the invention, the hepta-deuterated "E64d7", to guinea pigs results in a dose response reduction in FIG. 10(A) brain Aβ(40), FIG. 10(B) brain Aβ(42), FIG. 10(C) CSF Aβ, FIG. 10(D) CSF Aβ(42), FIG. 10(E) plasma Aβ(40) and FIG. 10(F) plasma Aβ(42), as discussed in detail in Example 9, below.
Figure 10B:
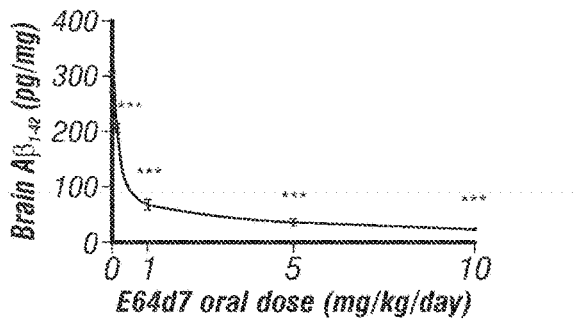
Figure 10C:
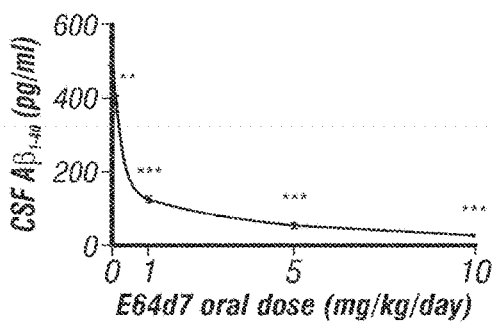
Figure 10D:
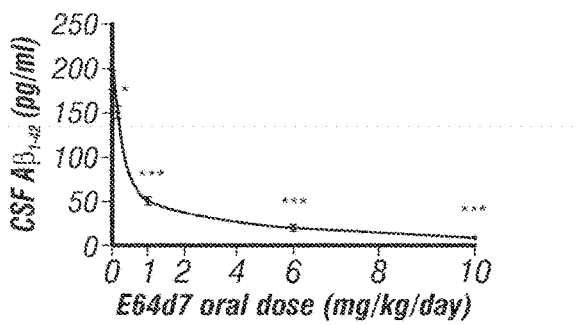
Figure 10E:
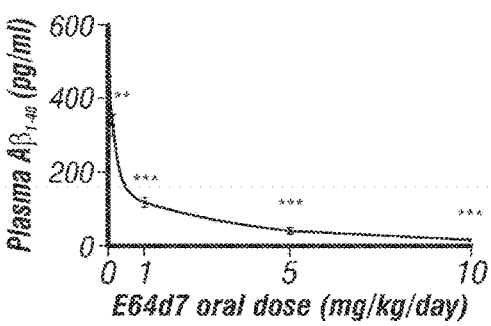
Figure 10F:
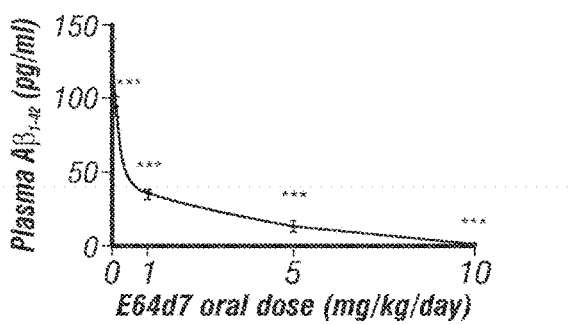

FIG. 10 graphically illustrates data showing that once-a-day for a week oral administration of the invention's exemplary composition of the invention "E64d7" (a hepta-deuterated isoform of E64d, illustrated above) to guinea pigs results in a dose response reduction in FIG. 10(A) brain Aβ(40), FIG. 10(B) brain Aβ(42), FIG. 10(C) CSF Aβ, FIG. 10(D) CSF Aβ(42), FIG. 10(E) plasma Aβ(40) and FIG. 10(F) plasma Aβ(42). Similar biphasic reductions in Aβ occurred for both peptide forms and in all compartments. Stars represent means that are statistically different from the no E64d dose group (student's t test  p<0.008, *p<0.001).

Figure 11A:
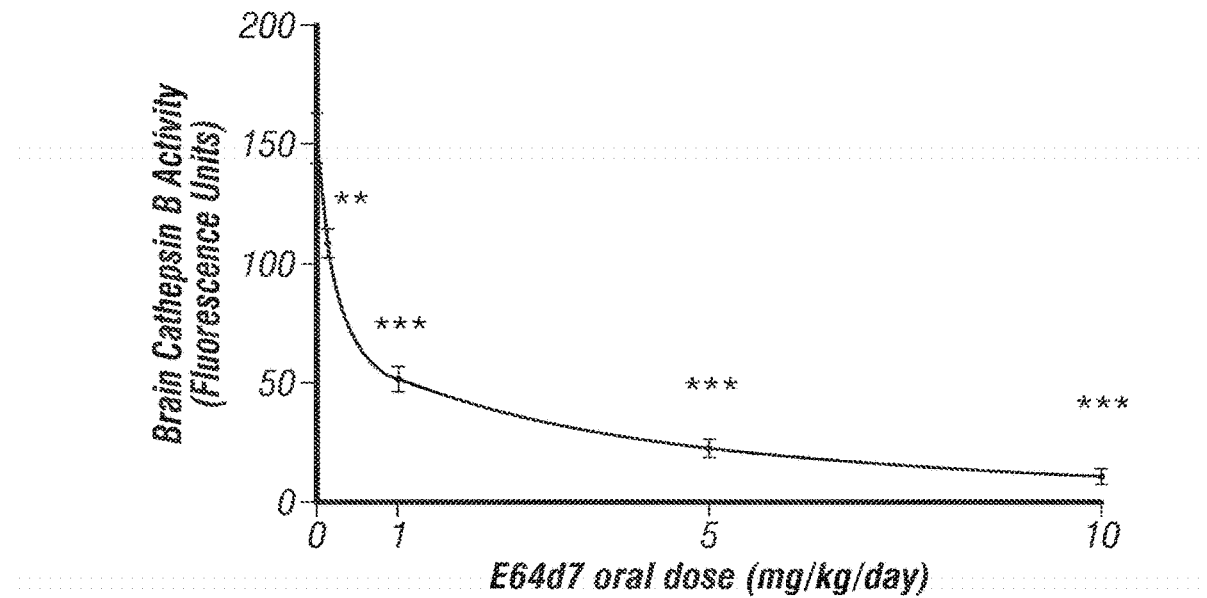
FIGS. 11A and 11B.
Figure 11B:
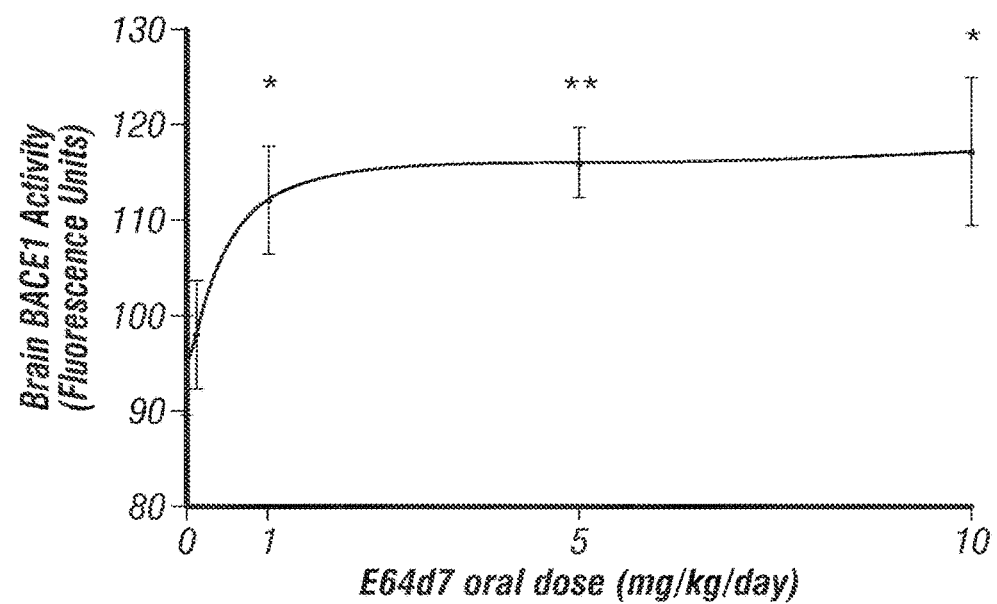
Figure 12A:
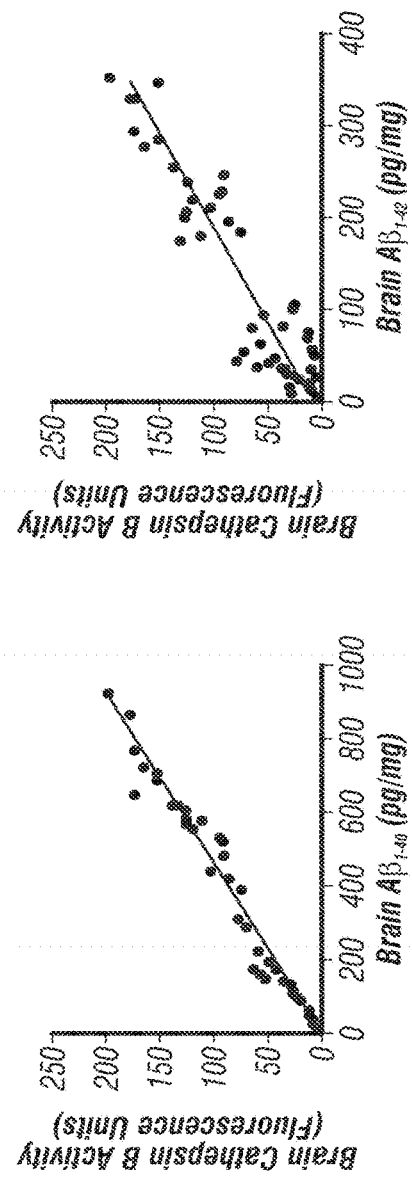
FIG. 12A, FIG. 12B, FIG. 12C and FIG. 12D graphically illustrate data showing paired guinea pig data for brain Aβ(40) or Aβ(42) vs brain cathepsin B or BACE1 activity, respectively for the combined "E64d7" dose groups.
Figure 12B:
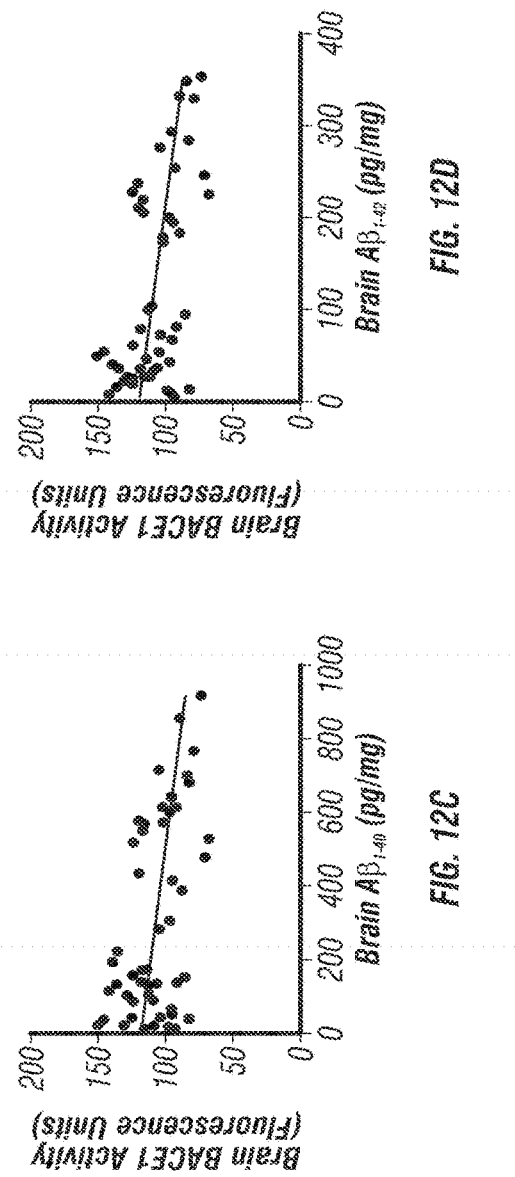
Figure 12C:
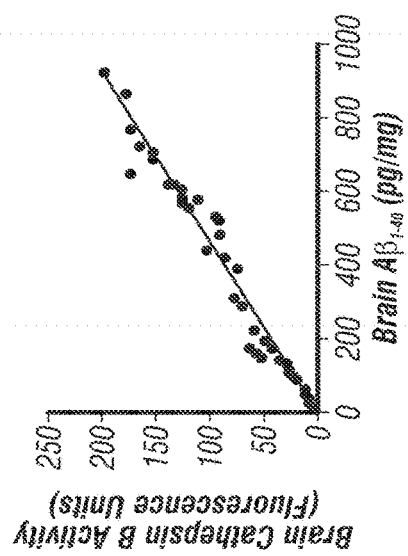
Figure 12D:
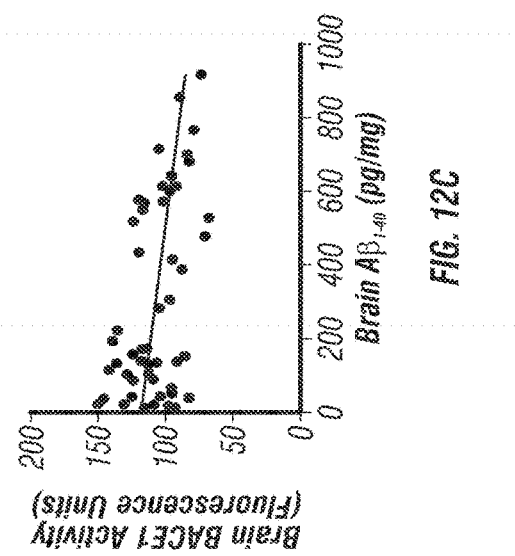

FIG. 11A (upper graph) graphically illustrates data showing that once-a-day oral administration of the exemplary composition of the invention "E64d7" to guinea pigs results in a dose response reduction of brain cathepsin B activity, which is similar to the biphasic lowering of Aβ. In contrast, FIG. 11B (lower graph) graphically illustrates data showing that same treatment results in an increase in brain BACE1 activity. Stars represent means that are statistically different from the no E64d dose group (student's t test * p<0.04, **p<0.005).

FIG. 12 graphically illustrates data showing paired guinea pig data for brain Aβ(40) or Aβ(42) vs brain cathepsin B or BACE1 activity, respectively for the combined "E64d7" dose groups. FIG. 12(A) Brain Aβ(40) vs brain cathepsin B activity shows a significant positive correlation (linear regression analysis, r squared 0.97, 95% confidence interval for the slope is 0.20 to 0.22, which is a significant non-zero slope at p<0.0001). This result is consistent with the hypothesis that brain cathepsin B inhibition reduces brain A3(40). FIG. 12(B) Brain Aβ(42) vs brain cathepsin B activity also has a significant positive correlation (r squared 0.87, 95% confidence interval for the slope is 0.43 to 0.54, which is a significant non-zero slope at p<0.0001). This data is also consistent with brain cathepsin B inhibition reducing brain Aβ(42). FIG. 12(C) Brain Aβ(40) vs brain BACE1 activity demonstrates a small negative correlation (r squared 0.24, 95% confidence interval for the slope is −0.05 to −0.02, which is a significant non-zero slope at p=0.0003). These data are not consistent with brain BACE1 inhibition decreasing brain A3(40). FIG. 12(D) Brain Aβ(42) vs brain BACE1 activity has a negative correlation (r squared 0.28, 95% confidence interval the slope is −0.14 to −0.05, which is a significant non-zero slope at p<0.001). These data are also not consistent with brain BACE1 inhibition causing the decrease in Aβ(42).

Figure 13A:
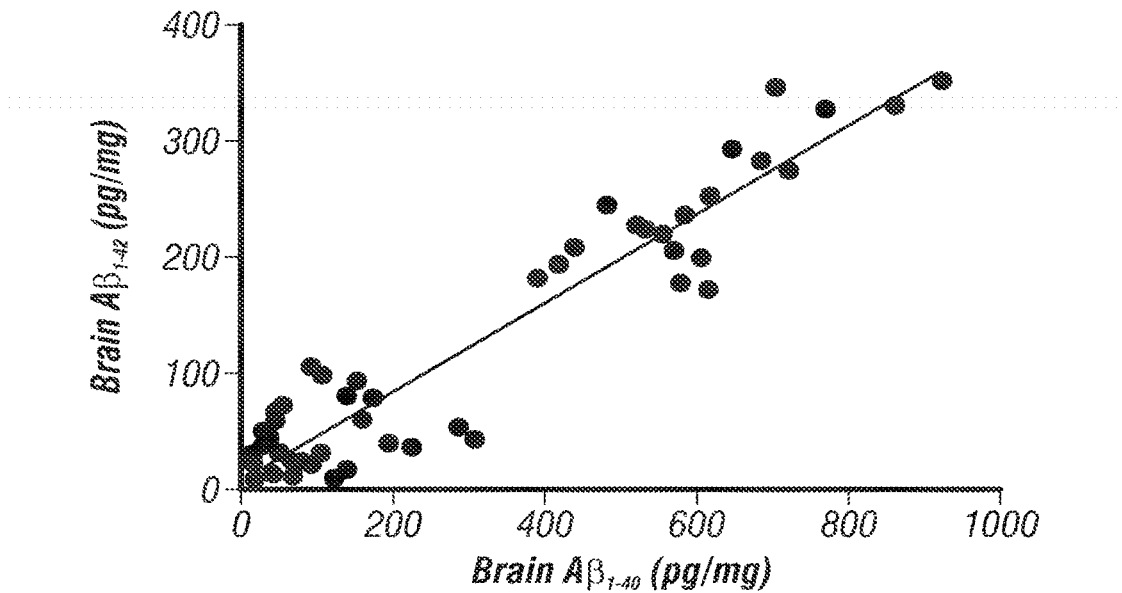
FIG. 13A and FIG. 13B graphically illustrate data showing paired guinea pig data for brain Aβ(40) vs Aβ(42) and brain cathepsin B vs BACE1 activity for all "E64d7" dose groups combined.
Figure 13B:
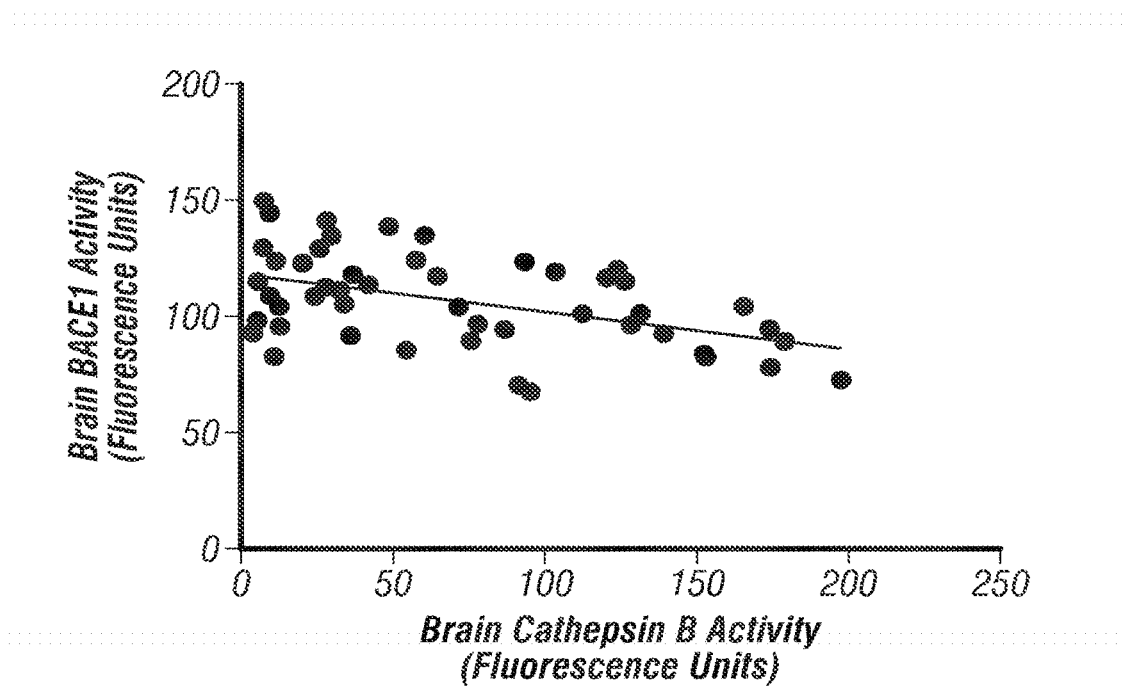

FIG. 13 graphically illustrates data showing paired guinea pig data for brain Aβ(40) vs Aβ(42) and brain cathepsin B vs BACE1 activity for all "E64d7" dose groups combined. FIG. 13(A) Brain Aβ(40) vs Aβ(42) shows a significant positive correlation (linear regression analysis, r squared 0.90, 95% confidence interval for the slope is 0.34 to 0.42, which is a significant non-zero slope at p<0.0001). This result is consistent with both forms of Aβ being reduced in each animal at a ratio of about 1 to 0.4 Aβ(40) to Aβ(42). FIG. 13(B) Brain cathepsin B vs BACE1 activity shows a slight negative correlation (r squared 0.22, 95% confidence interval for the slope is −0.25 to −0.07, which is a significant non-zero slope at p=0.0007). These data are consistent with brain BACE1 activity compensating for decreased cathepsin B activity.

Figure 14A:
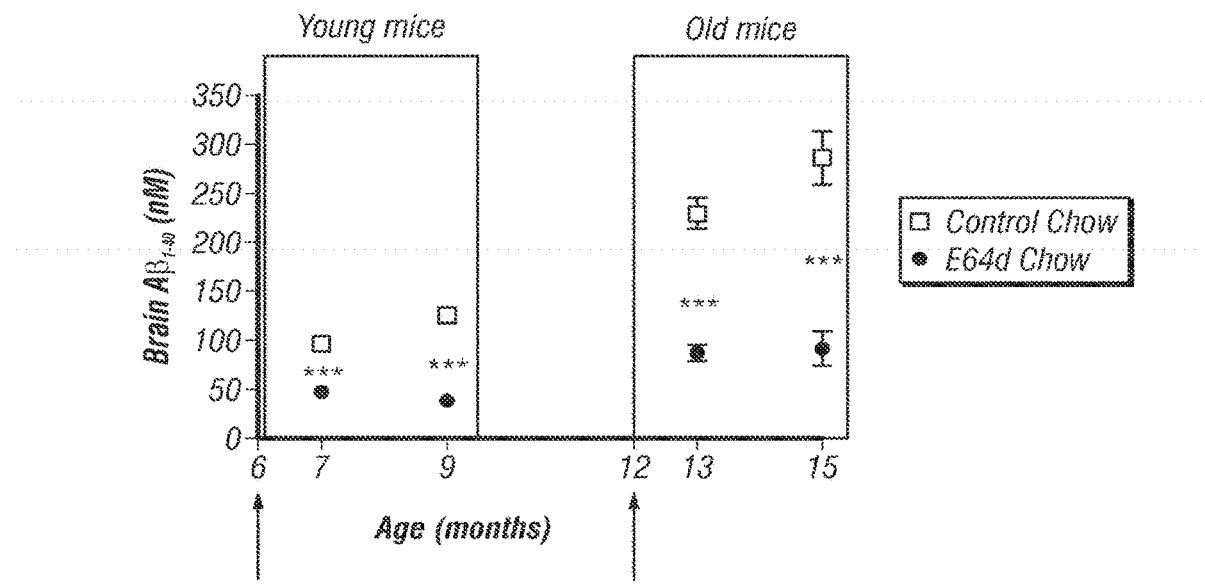
FIG. 14A and FIG. 14B graphically illustrate data showing the brain Aβ(40) and Aβ(42) data from the AB-007 (E64d, loxistatin)-doped mouse chow experiments, results from two experimental groups are shown.
Figure 14B:
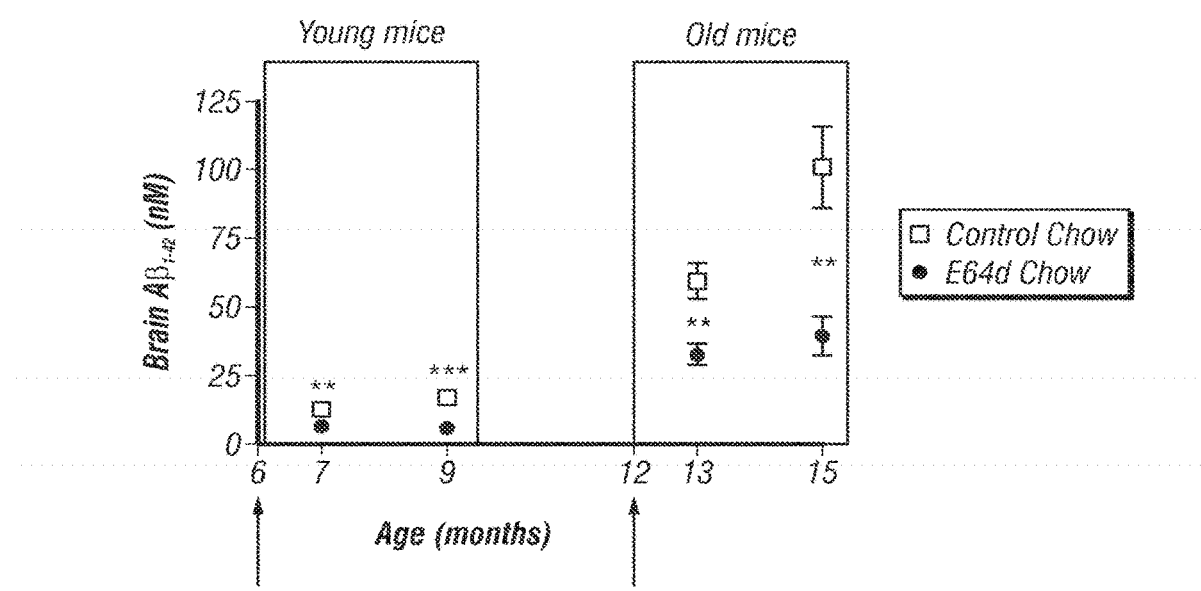

FIG. 14 graphically illustrates data showing the brain Aβ(40) and Aβ(42) data from the AB-007 (E64d, loxistatin)-doped mouse chow experiments. The results from two experimental groups are shown. The group labeled "Young mice" were fed either E64d doped chow beginning at 6 months of age as indicated by the arrow. The "Old mice" group began feeding on E64d doped chow beginning at 12 months of age as indicated by the arrow. Both groups were fed E64d doped chow for either 1 or 3 months after which they were sacrificed. Prior to those ages, experimental and control mice were fed control chow and control mice continued on that diet during the experimental period. FIG. 14(A) Feeding the E64d doped chow for 1 or 3 months caused a significant reduction in brain Aβ(40) in both the young and old mice relative to age-matched controls (* p<0.0001, student's t test). FIG. 14(B) The E64d doped chow fed for 1 or 3 months also caused a significant reduction in brain Aβ(42) in both the young and old mice relative age-matched controls ( p<0.003, *** p<0.0001, student's t test, n=10 animals per group). These data show that oral Aβ-007 (E64d, loxistatin) administration can reduce brain Aβ in an animal model of Alzheimer's disease.

FIG. 15 graphically compares the data shown in FIG. 14, for brain Aβ(40) and Aβ(42) levels in young and old animals feed AB-007 (E64d, loxistatin)-doped doped chow for 1 or 3 months. In all cases, brain Aβ was significantly higher in the old mice treated with either regime. FIG. 15(A) The brain Aβ(40) data from 1 month feeding, FIG. 15(B) the brain Aβ(40) data from 3 month feeding, FIG. 15(C) the brain Aβ(42) data from 1 month feeding, and FIG. 15(D) the brain Aβ(42) data from 3 month feeding are shown (***p<0.0001, student's t test).

Figure 16:
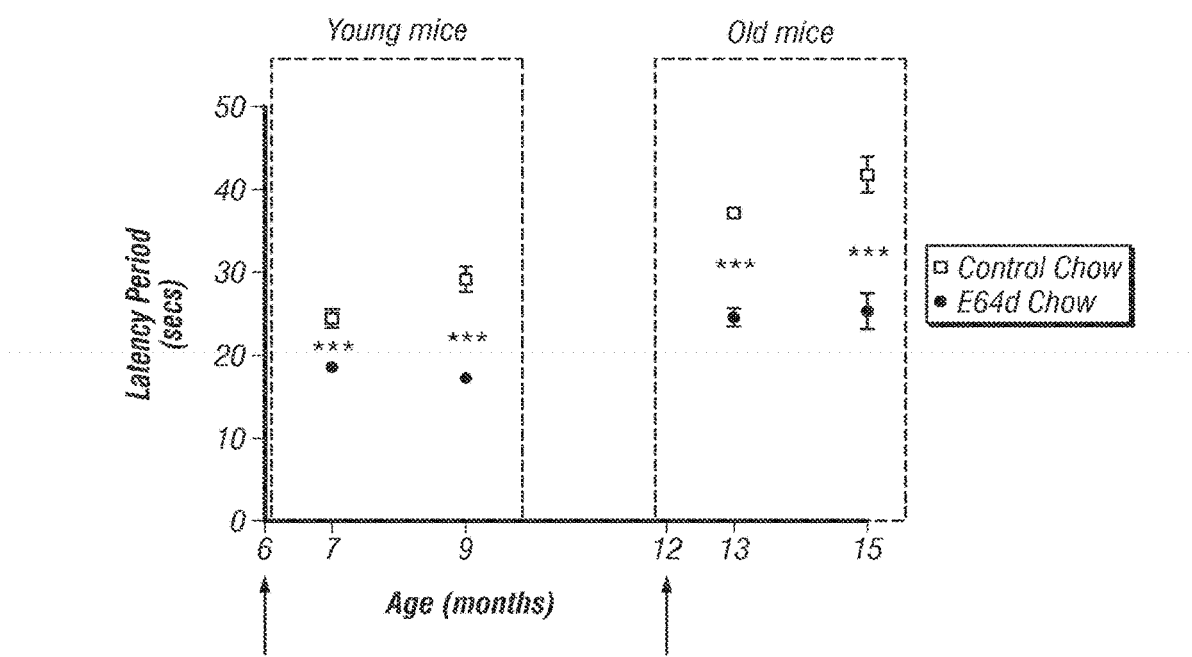
FIG. 16 graphically illustrates data showing the effects of AB-007 (E64d, loxistatin)-doped chow on the spatial memory deficit that develops in transgenic APPlon mice, as discussed in detail in Example 9, below.

FIG. 16 graphically illustrates data showing the effects of AB-007 (E64d, loxistatin)-doped chow on the spatial memory deficit that develops in transgenic APPlon (London APP) mice, see above description, and e.g. Hook, et al. (2008) supra. The Morris water maze test was used to measure the latency period, which is the time it takes an animal to swim to a submerged and not visible platform after having been previously trained as to the location of that platform. The longer the latency period, the poorer the spatial memory. Two groups of animals were evaluated, young and old mice. Young mice began feeding on E64d doped chow at 6 months of age (arrow), which is when only mild memory deficit develops. Old mice began feeding on E64d doped chow at 12 month of age (arrow), which is when severe memory deficit develops. Both experimental and control mice were transgenic APPlon mice. The data show that feeding the mice the E64d-doped chow for either 1 month or 3 months to either age group significantly reduced the mean latency period relative to age-matched controls (***p<0.0001, student's t test, n=10 animals per group). Thus, the treatment improved the memory deficit in animals having either mild or severe spatial memory deficit. The data suggest that oral administration of AB-007 (E64d, loxistatin) is effective for improving the early and late memory deficit that develops in Alzheimer's disease.

FIG. 17 graphically illustrates data showing a paired data analysis from the mouse experiments between brain Aβ(40) or Aβ(42) peptides and latency period for young and old mice either treated or not with AB-007 (E64d, loxistatin). FIG. 17(A) graphically illustrates the effect of feeding young mice either the control or E64d-doped chow for 1 month on brain Aβ(40) peptide and latency period is shown. Both control and E64d E64d-doped chow fed mice exhibited a positive correlation between brain Aβ(40) peptide and latency period (r squared 0.98 and 0.96 for control and treated, respectively). The slope of the linear regression analysis for the control was slightly more positive than the treated and that was statistically different (95% confidence interval for the slope was 0.14 to 0.16 and 0.095 and 0.12 for the control and treated respectively, difference in the slopes p<0.0001).

FIG. 17(B) graphically illustrates the effect of the E64d-doped chow feeding on young animals on brain Aβ(42) peptide vs. latency period is shown. Both control and E64d-fed mice exhibited a positive correlation between brain Aβ(42) peptide and latency period (r squared 0.97 and 0.86 for the control and treated, respectively). The slope of the linear regression analysis for the control and treated animals was not significantly different (95% confidence interval was 0.80 to 1.00 and 0.68 to 1.03 for the control and treated, respectively).

FIG. 17(C) graphically illustrates the effect of the E64d-doped chow feeding on old animals on brain Aβ(40) peptide and latency period is shown. Both control and E64d-fed mice had a positive correlation between on brain Aβ(40) and latency period (r squared 0.90 and 0.98 for control and treated, respectively) (in other words, the more brain Aβ(40) peptide the longer the latency period, where a longer latency period indicates more brain function deficit, i.e., a poorer memory). The slope of the linear analysis for the control was significantly less than that for the E64d treated animals (95% confidence interval was 0.06 to 0.82 and 0.12 to 0.13 for the control and treated, respectively, p<0.0001).

FIG. 17(D) graphically illustrates the effect of the E64d-doped chow feeding on old animals on brain Aβ(42) and latency period is shown. Both control and E64d fed mice had a positive correlation between on brain Aβ(42) peptide and latency period (r squared 0.92 and 0.93 for control and treated, respectively) (in other words, the more brain Aβ(42) peptide the longer the latency period, where a longer latency period indicates more brain function deficit, i.e., a poorer memory). The slope of the linear analysis for the control was significantly less than that for the E64d treated animals (95% confidence interval was 0.06 to 0.11 to 0.15 and 0.25 to 0.33 for the control and treated, respectively, p<0.0001).

SUMMARY Mouse chow data analysis

Percent reduction in Aβ

Aβ40

1 month feeding

| Mouse Age | Mean Control | Mean treated | Difference | % Control |
|---|---|---|---|---|
| Young | 95.2 | 47.7 | 47.5 | 50 |
| Old | 230.0 | 87.1 | 142.9 | 62 |

Aβ40

3 Month Feeding

| Mouse Age | Mean Control | Mean treated | Difference | % Control |
|---|---|---|---|---|
| Young | 126.1 | 38.7 | 87.4 | 69 |
| Old | 286.5 | 91.2 | 195.3 | 68 |

Summary Aβ 40 (1 & 3 month feeding)

| Mouse Age | Mean % Control |
|---|---|
| Young | 60 |
| Old | 65 |
| All Ages | 64 |

Aβ42

1 month feeding

| Mouse Age | Mean Control | Mean treated | Difference | % Control |
|---|---|---|---|---|
| Young | 11.5 | 5.5 | 6 | 52 |
| Old | 58.5 | 31.9 | 26.6 | 45 |

Aβ42

3 month feeding

| Mouse Age | Mean Control | Mean treated | Difference | % Control |
|---|---|---|---|---|
| Young | 16.2 | 4.5 | 11.7 | 72 |
| Old | 99.8 | 61.3 | 38.5 | 39 |

Summary Aβ42 (1 & 3 month feeding)

| Mouse Age | Mean % Control |
|---|---|
| Young | 62 |
| Old | 42 |
| All Ages | 52 |

In summary, these data show that in general brain Aβ(40) and Aβ(42) peptides are highly positively correlated with spatial memory deficit and that treating the animals with E64d results in about the same or slightly less positive correlation in the young animals and a much greater positive correlation in old animals relative to age-matched controls. These data illustrate the efficacy of E64d in improving memory deficit in aged animals; and while the invention is not limited by any particular mechanism of action, these also data illustrate the efficacy of E64d in decreasing levels of brain Aβ(40) and Aβ(42) peptide.

Although the foregoing invention has been described in some detail by way of illustration and example for purposes of clarity of understanding, it will be readily apparent to one of ordinary skill in the art in light of the teachings of this application that certain changes and modifications may be made thereto without departing from the spirit or scope of the appended claims. A number of aspects of the invention have been described. Nevertheless, it will be understood that various modifications may be made without departing from the spirit and scope of the invention. Accordingly, other aspects are within the scope of the following claims.

All publications, databases, patents, and patent applications cited in this specification are herein expressly incorporated by reference as if each was specifically and individually indicated to be incorporated by reference.

What is claimed is:

1. A pharmaceutical composition comprising a compound of Formula I:

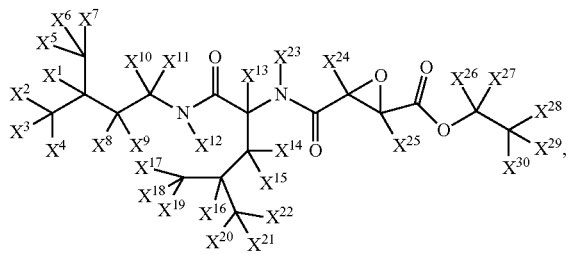

or

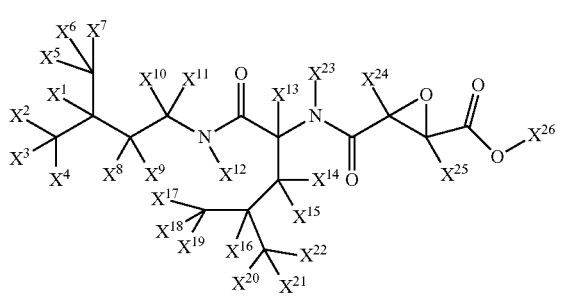

Formula II wherein for both Formula I and Formula II, $X^1$ through $X^{11}$ are -D (deuterium) (positions $X^1$ through $X^{11}$ are deuterated), and $X^{12}$ through $X^{30}$ (Formula I) or $X^{12}$ through $X^{26}$ (Formula II) are H (hydrogen).

2. The pharmaceutical composition of claim 1, wherein for both Formula I and Formula II; $X^1$ through $X^7$ are -D (deuterium) (positions $X^1$ through $X^7$ are deuterated), and $X^8$ through $X^{30}$ (Formula I) or $X^8$ through $X^{26}$ (Formula II) are —H (hydrogen).

3. The pharmaceutical composition of claim 1, wherein the compound of Formula I has a stereospecificity as set forth in Formula III:

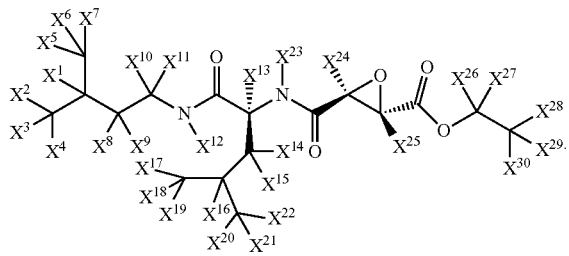

III

4. The pharmaceutical composition of claim 3, wherein the compound is conjugated to a chemical delivery system (CDS), or further comprises a chemical delivery system (CDS) selected from the group comprising a pyridinium a 1,4 dihydrotrigonelline esters, or a dihydroquinoline or a dihydroisoquinoline, and optionally the pyridinium is selected from the group consisting of a 3-methyl-1-propylpyridinium, a 1-butyl-3-methylpyridinium and a 1-butyl-4-methylpyridinium.

5. The pharmaceutical composition of claim 1, wherein the compound is formulated in combination with, or together with, a selegiline, selegiline hydrochloride, or a deprenyl.

6. The pharmaceutical composition of claim 1, formulated in unit dosage form, and optionally a unit dosage is between about 1 mg and about 400 mg; or is between about 1 mg and about 250 mg; or is about 5 mg and about 150 mg; or is between about 1 mg and about 75 mg; or is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, or about 75 mg.

7. The pharmaceutical composition of claim 1, formulated for administration as a liquid dosage form or a solid dosage form, or for parenteral administration or enteral administration.

8. The pharmaceutical composition of claim 1, wherein the compound is formulated for administration as, or in the form of, an injectable sterile formulation, a gel, a lotion, a spray, an aerosol, a powder, a patch, an adhesive tape, a gel, a liquid, an elixir, a syrup, a suspension, a lyophilate, a lozenge, a pill, a geltab, a lozenge, a tablet, a capsule and/or an implant.

9. The pharmaceutical composition of claim 1, wherein the compound is formulated as a chow, or a feed or a feed supplement.

10. The pharmaceutical composition of claim 1, wherein the compound is formulated in combination with or together with a nutritional supplement or a vitamin.

11. The pharmaceutical composition of claim 1, wherein the compound is formulated in combination with or together with a non-steroidal anti-inflammatory drug.

12. The pharmaceutical composition of claim 1, wherein the compound is formulated in combination with or together with an antioxidant.

13. The pharmaceutical composition of claim 1, wherein the compound is formulated for administration as an implantable infusion system, and the compound is administered by an implantable infusion system.

14. The pharmaceutical composition of claim 1, wherein the composition is formulated with microencapsulation to delay disintegration and adsorption in the gastrointestinal tract to provide a sustained action over a longer period.

15. The pharmaceutical composition of claim 1, wherein the composition is formulated with a time delay material, and optionally the time delay material comprises a glyceryl monostearate or a glyceryl distearate.

16. The pharmaceutical composition of claim 1, wherein the composition is formulated with a solid or a liquid carrier.

17. The pharmaceutical composition of claim 1, wherein the composition is formulated as or with: an aqueous or a non-aqueous solvent, an aqueous or a non-aqueous solution, a suspension, an emulsion or a solid, and optionally the non-aqueous solvent comprises a propylene glycol, a polyethylene glycol, a vegetable oil, an injectable organic ester, and optionally the aqueous carrier comprises water, an ethanol, an alcoholic/aqueous solution, a glycerol, a saline or a buffered media.

18. A liposome comprising a pharmaceutical composition of claim 1.

19. An implant, an osmotic pump, an implantable infusion system or an intrathecal catheter, comprising a pharmaceutical composition of claim 1.

20. A blister pack, blister packettes, blister package, lidded blister, blister card, clamshell, tray or shrinkwrap, having packaged therein a pharmaceutical composition of claim 1.

21. A pharmaceutical composition comprising a compound of Formula IV:

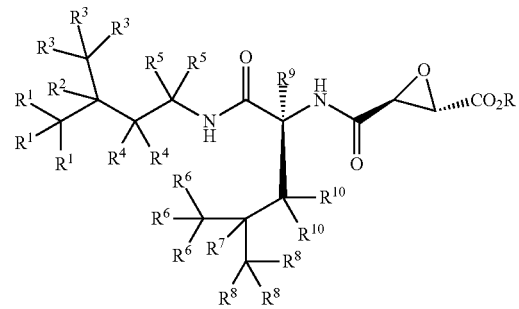

IV wherein $R^1$, $R^2$, R3, R4, and R5 are -D (deuterium), and R6, R7, R8, R9, R10 and R are —H (hydrogen).

22. The pharmaceutical composition of claim 21, wherein the compound of Formula W R1 through R3 are -D (deuterium) and R4 through R10 are —H (hydrogen) and R is ethyl.

23. The pharmaceutical composition of claim 21, wherein the compound of Formula W R1 through R3 are -D (deuterium) and R4 through R10 and R are —H (hydrogen).

* * * * *